(12) United States Patent
Cook et al.

(10) Patent No.: US 6,864,078 B2
(45) Date of Patent: Mar. 8, 2005

(54) 14790, NOVEL PROTEIN KINASE MOLECULE AND USES THEREFOR

(75) Inventors: William James Cook, Hanover, NH (US); Rosana Kapeller-Libermann, Chestnut Hill, MA (US); Helga Rubsamen-Waigmann, Wuppertal (DE); Frank Spaltmann, Cologne (DE)

(73) Assignees: Millennium Pharmaceuticals, Inc., Cambridge, MA (US); Bayer Corporation, Pittsburgh, PA (US)

( * ) Notice: Subject to any disclaimer, the term of this patent is extended or adjusted under 35 U.S.C. 154(b) by 0 days.

(21) Appl. No.: 09/515,806

(22) Filed: Feb. 29, 2000

(65) Prior Publication Data

US 2002/0132321 A1 Sep. 19, 2002

(51) Int. Cl.[7] .............................. C12N 9/12; C12N 5/00; C12N 15/00; C12Q 1/48; C12P 21/06
(52) U.S. Cl. ......................... 435/194; 435/15; 435/325; 435/252.3; 435/320.1; 435/69.1; 435/471; 435/6; 536/23.2
(58) Field of Search ........................... 536/23.2; 435/15, 435/194, 325, 252.3, 320.1, 471, 69.1, 6

(56) References Cited

FOREIGN PATENT DOCUMENTS

| WO | WO 00/58473 A2 | 10/2000 |
|---|---|---|
| WO | WO 00/73469 A2 | 12/2000 |
| WO | WO 01/29564 A1 | 4/2001 |

OTHER PUBLICATIONS

Berlanga et al., EMBL accesion Nos. AJ243533 and AJ243428, 1999.*
Duesterhoeft et al., GenEMBL accesion Nos. AL137627 and AL157497, Feb. 2000.*
Broun et al., Science 282:1315–1317, 1998.*
Van de Loo et al., Proc. Natl. Acad. Sci. 92:6743–6747, 1995.*
Bork, Genome Research, 10:398–400, 2000.*
Berlanga, J.J. et al. (1999) *European Journal of Biochemistry* 265(2):754–762.
Database EM_HUM [Online], Accession No.: AL157497 (ID:HSM802494), XP002187764 Feb. 2000.
Database EM_HUM [Online], Accession No.: AL137627 (ID:HSM802391), XP002187765 Feb. 2000.
Database EM_HUM [Online], Accession No.: AL137676 (ID:HSM802022), XP002187766 Feb. 2000.
Database EM_HUM [Online], Accession No.: AB037759, XP002187767 Mar. 2000.
Birchmeier. C. et al. (1993) "Tyrosine Kinase receptors in the control of epithelial growth and morphogenesis during development" *Bioessays* 15:185–189.
Charbonneau, H. et al. (1992) "1002 Protein Phosphatases?" *Annu. Rev. Cell Biol.* 8:463–93.
D'Urso, G. et al. (1990) "Cell Cycle Control of DNA Replication by a Homologue from Human Cells of the P34$^{cdc2}$ Protein Kinase" *Science* 250:786–791.
Gomez, N. et al. (1991) "Dissection of the Protein Kinase cascade by which nerve growth factor activates MAP kinases" *Nature* 353: 170–173.
Hanks et al. (1988) "The Protein Kinase Family: Conserved Features and Deduced Phylogeny of the Catalytic Domains" *Science* 241:42–52.
Hunter, T. et al. (1992) "The Regulation of Transcription by Phosphorylation" *Cell* 70: 375–387.
Hunter, T. et al. (1994) "Cyclins and Cancer II: Cyclin D and CDK Inhibitors Come of Age" *Cell* 79: 573–582.
Husain–Chishti, A. et al. (1988) "Abolition of actin–bundling by phosphorylation of human erythocyte protein 4.9" *Nature* 334: 718–721.
Maller, J. L. (1991) "Mitotic control" *Curr. Opin. Cell Biol.* 3: 269–275.
Nurse, P. (1990) "Universal control mechanism regulating onset of M–phase" *Nature* 344: 503–508.
Posada, J. et al. (1992) "Molecular signal integration. Interplay between serine, threonine, and tyrosine phosphorylation" *Mol. Biol. Cell* 3: 583–592.
Sturgill, T. W. et al. (1988) "Insulin–stimulated MAP–2 kinase phosphorylates and activates ribosomal protein S6 kinase II" *Nature* 344:715–718.

* cited by examiner

Primary Examiner—Rebecca Prouty
Assistant Examiner—Delia Ramirez
(74) Attorney, Agent, or Firm—Millennium Pharmaceuticals Inc.

(57) ABSTRACT

The invention provides an isolated nucleic acid molecule, designated as a kinase nucleic acid molecule, which encodes a novel protein kinase. The invention also provides antisense nucleic acid molecules, recombinant expression vectors containing kinase nucleic acid molecules, host cells into which the expression vectors have been introduced, and nonhuman transgenic animals in which a kinase gene has been introduced or disrupted. The invention still further provides isolated 14790 proteins, fusion proteins, antigenic peptides and anti-kinase antibodies. Diagnostic, screening, and therapeutic methods utilizing compositions of the invention are also provided.

18 Claims, 53 Drawing Sheets

```
                TCGCCCCACGCGTCCGCACCGCCGCCCAGGCAAGGCCGCCCTGCCTTGGG
                                                          ↑SEQ.ID NO: 1
SEQ.ID NO: 2→ M    A    G    G    R    G    A    P         8
             CGCAGCGCTGCC ATG  GCT  GGG  GGC  CGT  GGG  GCC  CCC       24
SEQ.ID NO: 3 ↑→

G    R    G    R    D    E    P    P    E    S    Y        19
    GGG  CGC  GGC  CGG  GAC  GAG  CCT  CCG  GAG  AGC  TAC        57

P    Q    R    Q    D    H    E    L    Q    A    L        30
         CCG  CAA  CGA  CAG  GAC  CAC  GAG  CTA  CAG  GCC  CTG        90

E    A    I    Y    G    A    D    F    Q    D    L        41
         GAG  GCC  ATC  TAC  GGC  GCG  GAC  TTC  CAA  GAC  CTG       123

R    P    D    A    C    G    P    V    K    E    P        52
         CGG  CCG  GAC  GCT  TGC  GGA  CCG  GTC  AAA  GAG  CCC       156

P    E    I    N    L    V    L    Y    P    Q    G        63
         CCT  GAA  ATC  AAT  TTA  GTT  TTG  TAC  CCT  CAA  GGC       189

L    T    G    E    E    V    Y    V    K    V    D        74
         CTA  ACT  GGT  GAA  GAA  GTA  TAT  GTA  AAA  GTG  GAT       222

L    R    V    K    C    P    P    T    Y    P    D        85
         TTG  AGG  GTT  AAA  TGC  CCA  CCT  ACC  TAT  CCA  GAT       255

V    V    P    E    I    E    L    K    N    A    K        96
         GTA  GTT  CCT  GAA  ATA  GAG  TTA  AAA  AAT  GCC  AAA       288

G    L    S    N    E    S    V    N    L    L    K       107
         GGT  CTA  TCA  AAT  GAA  AGT  GTC  AAT  TTG  TTA  AAA       321

S    R    L    E    E    L    A    K    K    H    C       118
         TCT  CGC  CTA  GAA  GAA  CTG  GCC  AAG  AAA  CAC  TGT       354

G    E    V    M    I    F    E    L    A    Y    H       129
         GGG  GAG  GTG  ATG  ATC  TTT  GAA  CTG  GCT  TAC  CAC       387

V    Q    S    F    L    S    E    H    N    K    P       140
         GTG  CAG  TCA  TTT  CTC  AGC  GAG  CAT  AAC  AAG  CCC       420
```

FIG. 1A

```
  P    P    K    S    F    H    E    E    M    L    E    151
 CCT  CCC  AAG  TCT  TTT  CAT  GAA  GAA  ATG  CTG  GAA       453

R    R    A    Q    E    E    Q    Q    R    L    L    162
 AGG  CGG  GCT  CAG  GAG  GAG  CAG  CAG  AGG  CTG  TTG       486

E    A    K    R    K    E    E    Q    E    Q    R    173
 GAG  GCC  AAG  CGG  AAA  GAA  GAG  CAG  GAG  CAA  CGT       519

E    I    L    H    E    I    Q    R    R    K    E    184
 GAA  ATC  CTG  CAT  GAG  ATT  CAG  AGA  AGG  AAA  GAA       552

E    I    K    E    E    K    K    R    K    E    M    195
 GAG  ATA  AAA  GAA  GAG  AAA  AAA  AGG  AAA  GAA  ATG       585

A    K    Q    E    R    L    E    I    A    S    L    206
 GCT  AAG  CAG  GAA  CGT  TTG  GAA  ATT  GCT  AGT  TTG       618

S    N    Q    D    H    T    S    K    K    D    P    217
 TCA  AAC  CAA  GAT  CAT  ACC  TCT  AAG  AAG  GAC  CCA       651

G    G    H    R    T    A    A    I    L    H    G    228
 GGA  GGA  CAC  AGA  ACG  GCT  GCC  ATT  CTA  CAT  GGA       684

G    S    P    D    F    V    G    N    G    K    H    239
 GGC  TCT  CCT  GAC  TTT  GTA  GGA  AAT  GGT  AAA  CAT       717

R    A    N    S    S    G    R    S    R    R    E    250
 CGG  GCA  AAC  TCC  TCA  GGA  AGG  TCT  AGG  CGA  GAA       750

R    Q    Y    S    V    C    N    S    E    D    S    261
 CGT  CAG  TAT  TCT  GTA  TGT  AAT  AGT  GAA  GAT  TCT       783

P    G    S    C    E    I    L    Y    F    N    M    272
 CCT  GGC  TCT  TGT  GAA  ATT  CTG  TAT  TTC  AAT  ATG       816

G    S    P    D    Q    L    M    V    H    K    G    283
 GGG  AGT  CCT  GAT  CAG  CTC  ATG  GTG  CAC  AAA  GGG       849
```

FIG. 1B

```
K    C    I    G    S    D    E    Q    L    G    K     294
AAA  TGT  ATT  GGC  AGT  GAT  GAA  CAA  CTT  GGA  AAA   882

L    V    Y    N    A    L    E    T    A    T    G     305
TTA  GTC  TAC  AAT  GCT  TTG  GAA  ACA  GCC  ACT  GGT   915

G    F    V    L    L    Y    E    W    V    L    Q     316
GGC  TTT  GTC  TTG  TTG  TAT  GAG  TGG  GTC  CTT  CAG   948

W    Q    K    K    M    G    P    F    L    T    S     327
TGG  CAG  AAA  AAA  ATG  GGT  CCA  TTC  CTT  ACC  AGT   981

Q    E    K    E    K    I    D    K    C    K    K     338
CAA  GAA  AAA  GAG  AAG  ATT  GAT  AAG  TGC  AAA  AAG   1014

Q    I    Q    G    T    E    T    E    F    N    S     349
CAG  ATT  CAA  GGA  ACA  GAA  ACA  GAA  TTC  AAC  TCA   1047

L    V    K    L    S    H    P    N    V    V    R     360
CTG  GTA  AAA  TTG  AGC  CAT  CCA  AAT  GTA  GTA  CGC   1080

Y    L    A    M    N    L    K    E    Q    D    D     371
TAC  CTT  GCA  ATG  AAT  CTC  AAA  GAG  CAA  GAC  GAC   1113

S    I    V    V    D    I    L    V    E    H    I     382
TCC  ATC  GTG  GTG  GAC  ATT  TTA  GTG  GAG  CAC  ATT   1146

S    G    V    S    L    A    A    H    L    S    H     393
AGT  GGG  GTC  TCT  CTT  GCT  GCA  CAC  CTG  AGC  CAC   1179

S    G    P    I    P    V    H    Q    L    R    R     404
TCA  GGC  CCC  ATC  CCT  GTG  CAT  CAG  CTT  CGC  AGG   1212

Y    T    A    Q    L    L    S    G    L    D    Y     415
TAC  ACA  GCT  CAG  CTC  CTG  TCA  GGC  CTT  GAT  TAT   1245

L    H    S    N    S    V    V    H    K    V    L     426
CTG  CAC  AGC  AAT  TCT  GTG  GTG  CAT  AAG  GTC  CTG   1278
```

*FIG. 1C*

```
S    A    S    N    V    L    V    D    A    E    G         437
AGT  GCA  TCT  AAT  GTC  TTG  GTG  GAT  GCA  GAA  GGC       1311

T    V    K    I    T    D    Y    S    I    S    K         448
ACC  GTC  AAG  ATT  ACG  GAC  TAT  AGC  ATT  TCT  AAG       1344

R    L    A    D    I    C    K    E    D    V    F         459
CGC  CTC  GCA  GAC  ATT  TGC  AAG  GAG  GAT  GTG  TTT       1377

E    Q    T    R    V    R    F    S    D    N    A         470
GAG  CAA  ACC  CGA  GTT  CGT  TTT  AGT  GAC  AAT  GCT       1410

L    P    Y    K    T    G    K    K    G    D    V         481
CTG  CCT  TAT  AAA  ACG  GGG  AAG  AAA  GGA  GAT  GTT       1443

W    R    L    G    L    L    L    L    S    L    S         492
TGG  CGT  CTT  GGC  CTT  CTG  CTG  CTG  TCC  CTC  AGC       1476

Q    G    Q    E    C    G    E    Y    P    V    T         503
CAA  GGA  CAG  GAA  TGT  GGA  GAG  TAC  CCT  GTG  ACC       1509

I    P    S    D    L    P    A    D    F    Q    D         514
ATC  CCT  AGT  GAC  TTA  CCA  GCT  GAC  TTT  CAA  GAT       1542

F    L    K    K    C    V    C    L    D    D    K         525
TTT  CTA  AAG  AAA  TGT  GTG  TGC  TTG  GAT  GAC  AAG       1575

E    R    W    S    P    Q    Q    L    L    K    H         536
GAA  AGA  TGG  AGT  CCC  CAG  CAG  TTG  TTG  AAA  CAC       1608

S    F    I    N    P    Q    P    K    M    P    L         547
AGC  TTT  ATA  AAT  CCC  CAG  CCA  AAA  ATG  CCT  CTA       1641

V    E    Q    S    P    E    D    S    G    G    Q         558
GTG  GAA  CAA  AGT  CCT  GAA  GAT  TCT  GGA  GGA  CAA       1674

D    Y    V    E    T    V    I    P    S    N    R         569
GAT  TAT  GTT  GAG  ACT  GTT  ATT  CCT  AGC  AAC  CGG       1707

L    P    S    A    A    F    F    S    E    T    Q         580
CTA  CCC  AGT  GCT  GCC  TTC  TTT  AGT  GAG  ACA  CAG       1740
```

FIG. 1D

```
R   Q   F   S   R   Y   F   I   E   F   E    591
AGA CAG TTT TCC CGA TAC TTC ATT GAG TTT GAA  1773

E   L   Q   L   L   G   K   G   A   F   G    602
GAA TTA CAA CTT CTT GGT AAA GGA GCT TTT GGA  1806

A   V   I   K   V   Q   N   K   L   D   G    613
GCT GTC ATC AAG GTG CAG AAC AAG TTG GAC GGC  1839

C   C   Y   A   V   K   R   I   P   I   N    624
TGC TGC TAC GCA GTG AAG CGC ATC CCC ATC AAC  1872

P   A   S   R   Q   F   R   R   I   K   G    635
CCG GCC AGC CGG CAG TTC CGC AGG ATC AAG GGC  1905

E   V   T   L   L   S   R   L   H   H   E    646
GAA GTG ACA CTG CTG TCA CGG CTG CAC CAT GAG  1938

N   I   V   R   Y   Y   N   A   W   I   E    657
AAC ATT GTG CGC TAC TAC AAC GCC TGG ATC GAG  1971

R   H   E   R   P   A   G   P   G   T   P    668
CGG CAC GAG CGG CCG GCG GGA CCG GGG ACG CCG  2004

P   P   D   S   G   P   L   A   K   D   D    679
CCC CCG GAC TCC GGG CCC CTG GCC AAG GAT GAC  2037

R   A   A   R   G   Q   P   A   S   D   T    690
CGA GCT GCA CGC GGG CAG CCG GCG AGC GAC ACA  2070

D   G   L   D   S   V   E   A   A   A   P    701
GAC GGC CTG GAC AGC GTA GAG GCC GCC GCG CCG  2103

P   P   I   L   S   S   S   V   E   W   S    712
CCA CCC ATC CTC AGC AGC TCG GTG GAG TGG AGC  2136

T   S   G   E   R   S   A   S   A   R   F    723
ACT TCG GGC GAG CGC TCG GCC AGT GCC CGT TTC  2169
```

*FIG. 1E*

```
P   A   T   G   P   G   S   S   D   D   E    734
CCC GCC ACC GGC CCG GGC TCC AGC GAT GAC GAG  2202

D   D   D   E   D   E   H   G   G   V   F    745
GAC GAC GAC GAG GAC GAG CAC GGT GGC GTC TTC  2235

S   Q   S   F   L   P   A   S   D   S   E    756
TCC CAG TCC TTC CTG CCT GCT TCA GAT TCT GAA  2268

S   D   I   I   F   D   N   E   D   E   N    767
AGT GAT ATT ATC TTT GAC AAT GAA GAT GAG AAC  2301

S   K   S   Q   N   Q   D   E   D   C   N    778
AGT AAA AGT CAG AAT CAG GAT GAA GAT TCC AAT  2334

E   K   N   G   C   H   E   S   E   P   S    789
GAA AAG AAT GGC TGC CAT GAA AGT GAG CCA TCA  2367

V   T   T   E   A   V   H   Y   L   Y   I    800
GTG ACG ACT GAG GCT GTG CAC TAC CTA TAC ATC  2400

Q   M   E   Y   C   E   K   S   T   L   R    811
CAG ATG GAG TAC TGT GAG AAG AGC ACT TTA CGA  2433

D   T   I   D   Q   G   L   Y   R   D   T    822
GAC ACC ATT GAC CAG GGA CTG TAT CGA GAC ACC  2466

V   R   L   W   R   L   F   R   E   I   L    833
GTC AGA CTC TGG AGG CTT TTT CGA GAG ATT CTG  2499

D   G   L   A   Y   I   H   E   K   G   M    844
GAT GGA TTA GCT TAT ATC CAT GAG AAA GGA ATG  2532

I   H   R   D   L   K   P   V   N   I   F    855
ATT CAC CGG GAT TTG AAG CCT GTC AAC ATT TTT  2565

L   D   S   D   D   H   V   K   I   G   D    866
TTG GAT TCT GAT GAC CAT GTG AAA ATA GGT GAT  2598
```

*FIG. 1F*

```
  F   G   L   A   T   D   H   L   A   F   S    877
 TTT GGT TTG GCG ACA GAC CAT CTA GCC TTT TCT   2631

A   D   S   K   Q   D   D   Q   T   G   D    888
 GCT GAC AGC AAA CAA GAC GAT CAG ACA GGA GAC   2664

L   I   K   S   D   P   S   G   H   L   T    899
 TTG ATT AAG TCA GAC CCT TCA GGT CAC TTA ACT   2697

G   M   V   G   T   A   L   Y   V   S   P    910
 GGG ATG GTT GGC ACT GCT CTC TAT GTA AGC CCA   2730

E   V   Q   G   S   T   K   S   A   Y   N    921
 GAG GTC CAA GGA AGC ACC AAA TCT GCA TAC AAC   2763

Q   K   V   D   L   F   S   L   G   I   I    932
 CAG AAA GTG GAT CTC TTC AGC CTG GGA ATT ATC   2796

F   F   E   M   S   Y   H   P   M   V   T    943
 TTC TTT GAG ATG TCC TAT CAC CCC ATG GTC ACG   2829

A   S   E   R   I   F   V   L   N   Q   L    954
 GCT TCA GAA AGG ATC TTT GTT CTC AAC CAA CTC   2862

R   D   P   T   S   P   K   F   P   E   D    965
 AGA GAT CCC ACT TCG CCT AAG TTT CCA GAA GAC   2895

F   D   D   G   E   H   A   K   Q   K   S    976
 TTT GAC GAT GGA GAG CAT GCA AAG CAG AAA TCA   2928

V   I   S   W   L   L   N   H   D   P   A    987
 GTC ATC TCC TGG CTG TTG AAC CAC GAT CCA GCA   2961

K   R   P   T   A   T   E   L   L   K   S    998
 AAA CGG CCC ACA GCC ACA GAA CTG CTC AAG AGT   2994

E   L   L   P   P   P   Q   M   E   E   S   1009
 GAG CTG CTG CCC CCA CCC CAG ATG GAG GAG TCA   3027

E   L   H   E   V   L   H   H   T   L   T   1020
 GAG CTG CAT GAA GTG CTG CAC CAC ACG CTG ACC   3060
```

FIG. 1G

```
  N   V   D   G   K   A   Y   R   T   M   M     1031
AAC GTG GAT GGG AAG GCC TAC CGC ACC ATG ATG     3093

A   Q   I   F   S   Q   R   I   S   P   A     1042
GCC CAG ATC TTC TCG CAG CGC ATC TCC CCT GCC     3126

I   D   Y   T   Y   D   S   D   I   L   K     1053
ATC GAT TAC ACC TAT GAC AGC GAC ATA CTG AAG     3159

G   N   F   S   I   R   T   A   K   M   Q     1064
GGC AAC TTC TCA ATC CGT ACA GCC AAG ATG CAG     3192

Q   H   V   C   E   T   I   I   R   I   F     1075
CAG CAT GTG TGT GAA ACC ATC ATC CGC ATC TTT     3225

K   R   H   G   A   V   Q   L   C   T   P     1086
AAA AGA CAT GGA GCT GTT CAG TTG TGT ACT CCA     3258

L   L   L   P   R   N   R   Q   I   Y   E     1097
CTA CTG CTT CCC CGA AAC AGA CAA ATA TAT GAG     3291

H   N   E   A   A   L   F   M   D   H   S     1108
CAC AAC GAA GCT GCC CTA TTC ATG GAC CAC AGC     3324

G   M   L   V   M   L   P   F   D   L   R     1119
GGG ATG CTG GTG ATG CTT CCT TTT GAC CTG CGG     3357

I   P   F   A   R   Y   V   A   R   N   N     1130
ATC CCT TTT GCA AGA TAT GTG GCA AGA AAT AAT     3390

I   L   N   L   K   R   Y   C   I   E   R     1141
ATA TTG AAT TTA AAA CGA TAC TGC ATA GAA CGT     3423

V   F   R   P   R   K   L   D   R   F   H     1152
GTG TTC AGG CCG CGC AAG TTA GAT CGA TTT CAT     3456

P   K   E   L   L   E   C   A   F   D   I     1163
CCC AAA GAA CTT CTG GAG TGT GCA TTT GAT ATT     3489
```

*FIG. 1H*

```
  V   T   S   T   T   N   S   F   L   P   T   1174
 GTC ACT TCT ACC ACC AAC AGC TTT CTG CCC ACT  3522

A   E   I   I   Y   T   I   Y   E   I   I   1185
 GCT GAA ATT ATC TAC ACT ATC TAT GAA ATC ATC  3555

Q   E   F   P   A   L   Q   E   R   N   Y   1196
 CAA GAG TTT CCA GCA CTT CAG GAA AGA AAT TAC  3588

S   I   Y   L   N   H   T   M   L   L   K   1207
 AGT ATT TAT TTG AAC CAT ACC ATG TTA TTG AAA  3621

A   I   L   L   H   C   G   I   P   E   D   1218
 GCA ATA CTC TTA CAC TGT GGG ATC CCA GAA GAT  3654

K   L   S   Q   V   Y   I   I   L   Y   D   1229
 AAA CTC AGT CAA GTC TAC ATT ATT CTG TAT GAT  3687

A   V   T   E   K   L   T   R   R   E   V   1240
 GCT GTG ACA GAG AAG CTG ACG AGG AGA GAA GTG  3720

E   A   K   F   C   N   L   S   L   S   S   1251
 GAA GCT AAA TTT TGT AAT CTG TCT TTG TCT TCT  3753

N   S   L   C   R   L   Y   K   F   I   E   1262
 AAT AGT CTG TGT CGA CTC TAC AAG TTT ATT GAA  3786

Q   K   G   D   L   Q   D   L   M   P   T   1273
 CAG AAG GGA GAT TTG CAA GAT CTT ATG CCA ACA  3819

I   N   S   L   I   K   Q   K   T   G   I   1284
 ATA AAT TCA TTA ATA AAA CAG AAA ACA GGT ATT  3852

A   Q   L   V   K   Y   G   L   K   D   L   1295
 GCA CAG TTG GTG AAG TAT GGC TTA AAA GAC CTA  3885

E   E   V   V   G   L   L   K   K   L   G   1306
 GAG GAG GTT GTT GGA CTG TTG AAG AAA CTC GGC  3918
```

*FIG. 1I*

```
    I   K   L   Q   V   L   I   N   L   G   L    1317
   ATC AAG TTA CAG GTC TTG ATC AAT TTG GGC TTG   3951

V   Y   K   V   Q   Q   H   N   G   I   I    1328
   GTT TAC AAG GTG CAG CAG CAC AAT GGA ATC ATC   3984

F   Q   F   V   A   F   I   K   R   R   Q    1339
   TTC CAG TTT GTG GCT TTC ATC AAA CGA AGG CAA   4017

R   A   V   P   E   I   L   A   A   G   G    1350
   AGG GCT GTA CCT GAA ATC CTC GCA GCT GGA GGC   4050

R   Y   D   L   L   I   P   Q   F   R   G    1361
   AGA TAT GAC CTG CTG ATT CCC CAG TTT AGA GGG   4083

P   Q   A   L   G   P   V   P   T   A   I    1372
   CCA CAA GCT CTG GGG CCA GTT CCC ACT GCC ATT   4116

G   V   S   I   A   I   D   K   I   S   A    1383
   GGG GTC AGC ATA GCT ATA GAC AAG ATA TCT GCT   4149

A   V   L   N   M   E   E   S   V   T   I    1394
   GCT GTC CTC AAC ATG GAG GAA TCT GTT ACA ATA   4182

S   S   C   D   L   L   V   V   S   V   G    1405
   AGC TCT TGT GAC CTC CTG GTT GTA AGT GTT GGT   4215

Q   M   S   M   S   R   A   I   N   L   T    1416
   CAG ATG TCT ATG TCC AGG GCC ATC AAC CTA ACC   4248

Q   K   L   W   T   A   G   I   T   A   E    1427
   CAG AAA CTC TGG ACA GCA GGC ATC ACA GCA GAA   4281

I   M   Y   D   W   S   Q   S   Q   E   E    1438
   ATC ATG TAC GAC TGG TCA CAG TCC CAA GAG GAA   4314

L   Q   E   Y   C   R   H   H   E   I   T    1449
   TTA CAA GAG TAC TGC AGA CAT CAT GAA ATC ACC   4347

Y   V   A   L   V   S   D   K   E   G   S    1460
   TAT GTG GCC CTT GTC TCG GAT AAA GAA GGA AGC   4380
```

*FIG. 1J*

```
  H   V   K   V   K   S   F   E   K   E   R    1471
CAT GTC AAG GTT AAG TCT TTC GAG AAG GAA AGG    4413

Q   T   E   K   R   V   L   E   T   E   L    1482
CAG ACA GAG AAG CGT GTG CTG GAG ACT GAA CTT    4446

V   D   H   V   L   Q   K   L   R   T   K    1493
GTG GAC CAT GTA CTG CAG AAA CTG AGG ACT AAA    4479

V   T   D   E   R   N   G   R   E   A   S    1504
GTC ACT GAT GAA AGG AAT GGC AGA GAA GCT TCC    4512

D   N   L   A   V   Q   N   L   K   G   S    1515
GAT AAT CTT GCA GTG CAA AAT CTG AAG GGG TCA    4545

F   S   N   A   S   G   L   F   E   I   H    1526
TTT TCT AAT GCT TCA GGT TTG TTT GAA ATC CAT    4578

G   A   T   V   V   P   I   V   S   V   L    1537
GGA GCA ACA GTG GTT CCC ATT GTG AGT GTG CTA    4611

A   P   E   K   L   S   A   S   T   R   R    1548
GCC CCG GAG AAG CTG TCA GCC AGC ACT AGG AGG    4644

R   Y   E   T   Q   V   Q   T   R   L   Q    1559
CGC TAT GAA ACT CAG GTA CAA ACT CGA CTT CAG    4677

T   S   L   A   N   L   H   Q   K   S   S    1570
ACC TCC CTT GCC AAC TTA CAT CAG AAA AGC AGT    4710

E   I   E   I   L   A   V   D   L   P   K    1581
GAA ATT GAA ATT CTG GCT GTG GAT CTA CCC AAA    4743

E   T   I   L   Q   F   L   S   L   E   W    1592
GAA ACA ATA TTA CAG TTT TTA TCA TTA GAG TGG    4776

D   A   D   E   Q   A   F   N   T   T   V    1603
GAT GCT GAT GAA CAG GCA TTT AAC ACA ACT GTG    4809
```

FIG. 1K

```
K    Q    L    L    S    R    L    P    K    Q    R    1614
AAG  CAG  CTG  CTG  TCA  CGC  CTG  CCA  AAG  CAA  AGA  4842

Y    L    K    L    V    C    D    E    I    Y    N    1625
TAC  CTC  AAA  TTA  GTC  TGT  GAT  GAA  ATT  TAT  AAC  4875

I    K    V    E    K    K    V    S    V    L    F    1636
ATC  AAA  GTA  GAA  AAA  AAG  GTG  TCT  GTG  CTA  TTT  4908

L    Y    S    Y    R    D    D    Y    Y    R    I    1647
CTG  TAC  AGC  TAT  AGA  GAT  GAC  TAC  TAC  AGA  ATC  4941

L    F    *    1650
TTA  TTT  TAA  4950 — SEQ.ID NO: 3
```

CCCTAAAGAACTGTCGTTAACCTCATTCAAACAGACAGAGGCTTATACTG
GAATAATGGAATGTTGTACATTCATCATAATTTAAAATTAAATTCTAAGA
AGAGGCTGGGTGCAGTGGCTCACACCTTTAATCCCAGCACTTTGGGAAGC
CAAGGCAGGAAGACTGCTTGAAACCAGGAGTTTGAGACCAGCCTGAGCAA
CAAAGCAAGACCCCATCTCTATAAAAACTAAAAAAATTAGTTGGGCATGG
TGGCACATGCCTGTAGTCCCAGCTACTCCAGAGGCTGAGATGGATCATCT
GAGCCTCAGGAGGTTGAGGCTGCAGTGAGCTGTGACTGCGCCACTGCACT
CCAGTCTGGGACAACAGAGCAAGACCCTGTCTTAAAAAAAAAAGAAAAA
AAAATTTTTTTCTAAGAAGCTGTCCTACAAAGTTGAGCTTTGTTAGTTT
TTCATGTGTAATATATTATAAATTTATCTTTTGGGATATAATAAATGCTT
TCATATACCTGCA

FIG. 1L

```
6065914_eIF2kinase_man      ------------------------
14790                       MAGGRGAPGRGRDEPPESYPQRQDH
6066585_eIF2kinase_mouse    MAGGRGASGRGRAEPQESYSQRQDH 6065914_eIF2kinase_man      ------------------------
14790                       ELQALEAIYGADFQDLRPDACGPVK
6066585_eIF2kinase_mouse    ELQALEAIYGSDFQDLRPDARGRVR 6065914_eIF2kinase_man      -------------------------
14790                       EPPEINLVLYPQGLTGEEVYVKVDL
6066585_eIF2kinase_mouse    EPPEINLVLYPQGLAGEEVYVQVEL
```

FIG. 2A

```
6065914_eIF2kinase_man     --------------------------
14790                      RVKCPPTYPDVVPEIELKNAKGLSN
6066585_eIF2kinase_mouse   QVKCPPTYPDVVPEIELKNAKGLSN 6065914_eIF2kinase_man     --------------------------
14790                      ESVNLLKSRLEELAKKHCGEVMIFE
6066585_eIF2kinase_mouse   ESVNLLKSHLEELAKKQCGEVMIFE 6065914_eIF2kinase_man     --------------------------
14790                      LAYHVQSFLSEHNKPPPKSFHEEML
6066585_eIF2kinase_mouse   LAHHVQSFLSEHNKPPPKSFHEEML 6065914_eIF2kinase_man     --------------------------
14790                      ERRAQEEQQRLLEAKRKEEQEQREI
6066585_eIF2kinase_mouse   ERQAQEKQQRLLEARRKEEQEQREI 6065914_eIF2kinase_man     --------------------------
14790                      LHEIQRRKEEIKEEKKRKEMAKQER
6066585_eIF2kinase_mouse   LHEIQRRKEEIKEEKKRKEMAKQER 6065914_eIF2kinase_man     --------------------------
14790                      LEIASLSNQDHTSKKDPGGHRTAAI
6066585_eIF2kinase_mouse   LEITSLTNQDYASKRDPAGHRAAAI 6065914_eIF2kinase_man     --------------------------
14790                      LHGGSPDFVGNGKHRANSSGRSRRE
6066585_eIF2kinase_mouse   LHGGSPDFVGNGKARTYSSGRSRRE 6065914_eIF2kinase_man     --------------------------
14790                      RQYSVCNSEDSPGSCEILYFNMGSP
6066585_eIF2kinase_mouse   RQYSVCSGEPSPGSCDILHFSVGSP 6065914_eIF2kinase_man     --------------------------
14790                      DQLMVHKGKCIGSDEQLGKLVYNAL
6066585_eIF2kinase_mouse   DQLMVHKGRCVGSDEQLGKVVYNAL 6065914_eIF2kinase_man     --------------------------
14790                      ETATGGFVLLYEWVLQWQKKMGPFL
6066585_eIF2kinase_mouse   ETATGSFVLLHEWVLQWQK-MGPCL
```

*FIG. 2B*

6065914_eIF2kinase_man      --------------------------
14790                       TSQEKEKIDKCKKQIQGTETEFNSL
6066585_eIF2kinase_mouse    TSQEKEKIDKCKRQIQGAETEFSSL 6065914_eIF2kinase_man      --------------------------
14790                       VKLSHPNVVRYLAMNLKEQDDSIVV
6066585_eIF2kinase_mouse    VKLSHPNIVRYFAMNSREEEDSIVI 6065914_eIF2kinase_man      --------------------------
14790                       DILVEHISGVSLAAHLSHSGPIPVH
6066585_eIF2kinase_mouse    DILAEHVSGISLATHLSHSGPVPAH 6065914_eIF2kinase_man      --------------------------
14790                       QLRRYTAQLLSGLDYLHSNSVVHKV
6066585_eIF2kinase_mouse    QLRKYTAQLLAGLDYLHSNSVVHKV 6065914_eIF2kinase_man      --------------------------
14790                       LSASNVLVDAEGTVKITDYSISKRL
6066585_eIF2kinase_mouse    LSASSVLVDAEGTVKITDYSISKRL 6065914_eIF2kinase_man      --------------------------
14790                       ADICKEDVFEQTRVRFSDNALPYKT
6066585_eIF2kinase_mouse    ADICKEDVFEQARVRFSDSALPYKT 6065914_eIF2kinase_man      --------------------------
14790                       GKKGDVWRLGLLLLSLSQGQECGEY
6066585_eIF2kinase_mouse    GKKGDVWRLGLLLLSLSQGQECGEY 6065914_eIF2kinase_man      --------------------------
14790                       PVTIPSDLPADFQDFLKKCVCLDDK
6066585_eIF2kinase_mouse    PVTIPSDLPADFQDFLKKCVCLDDK 6065914_eIF2kinase_man      --------------------------
14790                       ERWSPQQLLKHSFINPQPKMPLVEQ
6066585_eIF2kinase_mouse    ERWSPQQLLKHSFINPQPKLPLVEQ 6065914_eIF2kinase_man      --------------------------
14790                       SPEDSGGQDYVETVIPSNRLPSAAF

*FIG. 2C*

```
6066585_eIF2kinase_mouse      SPEDSGGQDYIETVIPSNQLPSAAF

6065914_eIF2kinase_man        ------------------------
14790                         FSETQRQFSRYFIEFEELQLLGKGA
6066585_eIF2kinase_mouse      FSETQKQFSRYFIEFEELQLLGKGA 6065914_eIF2kinase_man        ------------------------
14790                         FGAVIKVQNKLDGCCYAVKRIPINP
6066585_eIF2kinase_mouse      FGAVIKVQNKLDGCCYAVKRIPINP 6065914_eIF2kinase_man        ------------------------
14790                         ASRQFRRIKGEVTLLSRLHHENIVR
6066585_eIF2kinase_mouse      ASRHFRRIKGEVTLLSRLHHENIVR 6065914_eIF2kinase_man        ------------------------
14790                         YYNAWIERHERPAGPGTPPPDSGPL
6066585_eIF2kinase_mouse      YYNAWIERHERPAVPGTPPPDCTPQ 6065914_eIF2kinase_man        ------------------------
14790                         AKDDRAARGQPASDTDGLDSVEAAA
6066585_eIF2kinase_mouse      AQDSPATCGKTSGDTEELGSVEAAA 6065914_eIF2kinase_man        ------------------------
14790                         PPPILSSSVEWSTSGERSASARFPA
6066585_eIF2kinase_mouse      PPPILSSSVEWSTSAERSTSTRFPV 6065914_eIF2kinase_man        ------------------------
14790                         TGPGSSDDEDDDEDEHGGVFSQSFL
6066585_eIF2kinase_mouse      TGQDSSSDEED-EDERDGVFSQSFL 6065914_eIF2kinase_man        ------------------------
14790                         PASDSESDIIFDNEDENSKSQNQDE
6066585_eIF2kinase_mouse      PASDSDSDIIFDNEDENSKSQNQDE 6065914_eIF2kinase_man        ------------------------
14790                         DCNEKNGCHESEPSVTTEAVHYLYI
```

*FIG. 2D*

```
6066585_eIF2kinase_mouse    DCNQKDGSHEIEPSVTAEAVHYLYI

6065914_eIF2kinase_man      ---------------------------
14790                       QMEYCEKSTLRDTIDQGLYRDTVRL
6066585_eIF2kinase_mouse    QMEYCEKSTLRDTIDQGLFRDTSRL 6065914_eIF2kinase_man      ---------------------------
14790                       WRLFREILDGLAYIHEKGMIHRDLK
6066585_eIF2kinase_mouse    WRLFREILDGLAYIHEKGMIHRDLK 6065914_eIF2kinase_man      ---------------------------
14790                       PVNIFLDSDDHVKIGDFGLATDHLA
6066585_eIF2kinase_mouse    PVNIFLDSDDHVKIGDFGLATDHLA 6065914_eIF2kinase_man      ---------------------------
14790                       FSADSKQDDQTGD-LIKSDPSGHLT
6066585_eIF2kinase_mouse    FTAEGKQDDQAGDGVIKSDPSGHLT 6065914_eIF2kinase_man      ---------------------------
14790                       GMVGTALYVSPEVQGSTKSAYNQKV
6066585_eIF2kinase_mouse    GMVGTALYVSPEVQGSTKSAYNQKV 6065914_eIF2kinase_man      ---------------------------
14790                       DLFSLGIIFFEMSYHPMVTASERIF
6066585_eIF2kinase_mouse    DLFSLGIIFFEMSYHPMVTASERIF 6065914_eIF2kinase_man      ---------------------------
14790                       VLNQLRDPTSPKFPEDFDDGEHAKQ
6066585_eIF2kinase_mouse    VLNQLRDPTSPKFPDDFDDGEHTKQ 6065914_eIF2kinase_man      ---------------------------
14790                       KSVISWLLNHDPAKRPTATELLKSE
6066585_eIF2kinase_mouse    KSVISWLLNHDPAKRPTAMELLKSE
```

*FIG. 2E*

```
6065914_eIF2kinase_man      ------------------------
14790                       LLPPPQMEESELHEVLHHTLTNVDG
6066585_eIF2kinase_mouse    LLPPPQMEESELHEVLHHTLANIDG 6065914_eIF2kinase_man      ------------------------
14790                       KAYRTMMAQIFSQRISPAIDYTYDS
6066585_eIF2kinase_mouse    KAYRTMMSQIFCQHISPAIDYTYDS 6065914_eIF2kinase_man      ------------------------
14790                       DILKGNFSIRTAKMQQHVCETIIRI
6066585_eIF2kinase_mouse    DILKGNFLIRTAKIQQLVCETIVRV 6065914_eIF2kinase_man      -------------------------
14790                       FKRHGAVQLCTPLLLPRNRQIYEHN
6066585_eIF2kinase_mouse    FKRHGAVQLCTPLLLPRNRQIYEHN 6065914_eIF2kinase_man      --ALFMDHSGMLVMLPFDLRIPFAR
14790                       EAALFMDHSGMLVMLPFDLRIPFAR
6066585_eIF2kinase_mouse    EAALFMDHSGMLVMLPFDLRVPFAR
                              *******************:****

6065914_eIF2kinase_man      YVARNNILILKRYCIERVFRPRKLD
14790                       YVARNNILNLKRYCIERVFRPRKLD
6066585_eIF2kinase_mouse    YVARNNILNLKRYCIERVFRPRKLD
                            *******  ****************

6065914_eIF2kinase_man      RFHPKELLECAFDIVTSTTNSFLPT
14790                       RFHPKELLECAFDIVTSTTNSFLPT
6066585_eIF2kinase_mouse    RFHPKELLECAFDIVTSTTNSSLPT
                            ********************* ***

6065914_eIF2kinase_man      AEIIYTIYEIIQEFPALQERNYSIY
14790                       AEIIYTIYEIIQEFPALQERNYSIY
6066585_eIF2kinase_mouse    AETIYTIYEIIQEFPALQERNYSIY
                            ** **********************
```

*FIG. 2F*

```
6065914_eIF2kinase_man      LNHTMLLKAILLHCGIPEDKLSQVY
14790                       LNHTMLLKAILLHCGIPEDKLSQVY
6066585_eIF2kinase_mouse    LNHTMLLKAILLHCGIPEDKLSQVY
                            *************************

6065914_eIF2kinase_man      IILYDAVTEKLTRREVEAKFCNLSL
14790                       IILYDAVTEKLTRREVEAKFCNLSL
6066585_eIF2kinase_mouse    VILYDAVTEKLTRREVEAKFCNLSL
                            :************************

6065914_eIF2kinase_man      SSNSLCRLYKFIEQKGDLQDLMPTI
14790                       SSNSLCRLYKFIEQKGDLQDLMPTI
6066585_eIF2kinase_mouse    SSNSLCRLYKFIEQKGDLQDLTPTI
                            ********************* ***

6065914_eIF2kinase_man      NSLIKQKTGIAQLVKYGLKDLEEVV
14790                       NSLIKQKTGIAQLVKYGLKDLEEVV
6066585_eIF2kinase_mouse    NSLIKQKTGVAQLVKYSLKDLEDVV
                            :********:******.*****:**

6065914_eIF2kinase_man      GLLKKLGIKLQVLINLGLVYKVQQH
14790                       GLLKKLGIKLQVLINLGLVYKVQQH
6066585_eIF2kinase_mouse    GLLKKLGVKLQVSINLGLVYKVQQH
                            *******:**** ********.***

6065914_eIF2kinase_man      NGIIFQFVAFIKRRQRAVPEILAAG
14790                       NGIIFQFVAFIKRRQRAVPEILAAG
6066585_eIF2kinase_mouse    TGIIFQFLAFSKRRQRVVPEILAAG
                            .******:** ****.*********

6065914_eIF2kinase_man      GRYDLLIPQFRGPQALGPVPTAIGV
14790                       GRYDLLIPQFRGPQALGPVPTAIGV
6066585_eIF2kinase_mouse    GRYDLLIPKFRGPQTVGPVPTAVGV
                            ********:*****:.******:**

6065914_eIF2kinase_man      SIAIDKISAAVLNMEESVTISSCDL
14790                       SIAIDKISAAVLNMEESVTISSCDL
6066585_eIF2kinase_mouse    SIAIDKIFAVVLNMEEPVTVSSCDL
                            ******* *.******.**.*****
```

FIG. 2G

| | |
|---|---|
| 6065914_eIF2kinase_man | LVVSVGQMSMSRAINLTQKLWTAGI |
| 14790 | LVVSVGQMSMSRAINLTQKLWTAGI |
| 6066585_eIF2kinase_mouse | LVVSVGQMSMSRAINLTQKLWTAGI |
| | ************************* |

| | |
|---|---|
| 6065914_eIF2kinase_man | TAEIMYDWSQSQEELQEYCRHHEIT |
| 14790 | TAEIMYDWSQSQEELQEYCRHHEIT |
| 6066585_eIF2kinase_mouse | TAEIMYDWSQSQEELQEYCRHHEIT |
| | ************************* |

| | |
|---|---|
| 6065914_eIF2kinase_man | YVALVSDKEGSHVKVKSFEKERQTE |
| 14790 | YVALVSDKEGSHVKVKSFEKERQTE |
| 6066585_eIF2kinase_mouse | YVALVSDKEGSHVKVKSFEKERQTE |
| | ************************* |

| | |
|---|---|
| 6065914_eIF2kinase_man | KRVLETELVDHVLQKLRTKVTDERN |
| 14790 | KRVLETELVDHVLQKLRTKVTDERN |
| 6066585_eIF2kinase_mouse | KRVLESDLVDHVMQKLRTKVGDERN |
| | ***:.*:*** ** |

| | |
|---|---|
| 6065914_eIF2kinase_man | GREASDNLAVQNLKGSFSNASGLFE |
| 14790 | GREASDNLAVQNLKGSFSNASGLFE |
| 6066585_eIF2kinase_mouse | FRDASDNLAVQTLKGSFSNASGLFE |
| | *:****.********** |

| | |
|---|---|
| 6065914_eIF2kinase_man | IHGATVVPIVSVLAPEKLSASTRRR |
| 14790 | IHGATVVPIVSVLAPEKLSASTRRR |
| 6066585_eIF2kinase_mouse | IHGTTVVPNVIVLAPEKLSASTRRR |
| | *:** * ************** |

| | |
|---|---|
| 6065914_eIF2kinase_man | YETQVQTRLQTSLANLHQKSSEIEI |
| 14790 | YETQVQTRLQTSLANLHQKSSEIEI |
| 6066585_eIF2kinase_mouse | HEIQVQTRLQTTLANLHQKSSEIEI |
| | :* *****:*********** |

FIG. 2H

```
6065914_eIF2kinase_man      LAVDLPKETILQFLSLEWDADEQAF
14790                       LAVDLPKETILQFLSLEWDADEQAF
6066585_eIF2kinase_mouse    LAVDLPKETILQFLSLEWDADEQAF
                            ***:****  * *************

6065914_eIF2kinase_man      NTTVKQLLSRLPKQRYLKLVCDEIY
14790                       NTTVKQLLSRLPKQRYLKLVCDEIY
6066585_eIF2kinase_mouse    NTTVKQLLSRLPKQRYLKLVCDEIY
                            *************************

6065914_eIF2kinase_man      NIKVEKKVSVLFLYSYRDDYYRILF

14790                       NIKVEKKVSVLFLYSYRDDYYRILF
                                                    ↑SEQ. ID NO: 4
6066585_eIF2kinase_mouse    NIKVEKKVSVLFLYSYRDDYYRILF
                                                    ↑SEQ. ID NO: 5
                            *************************
```

FIG. 2I

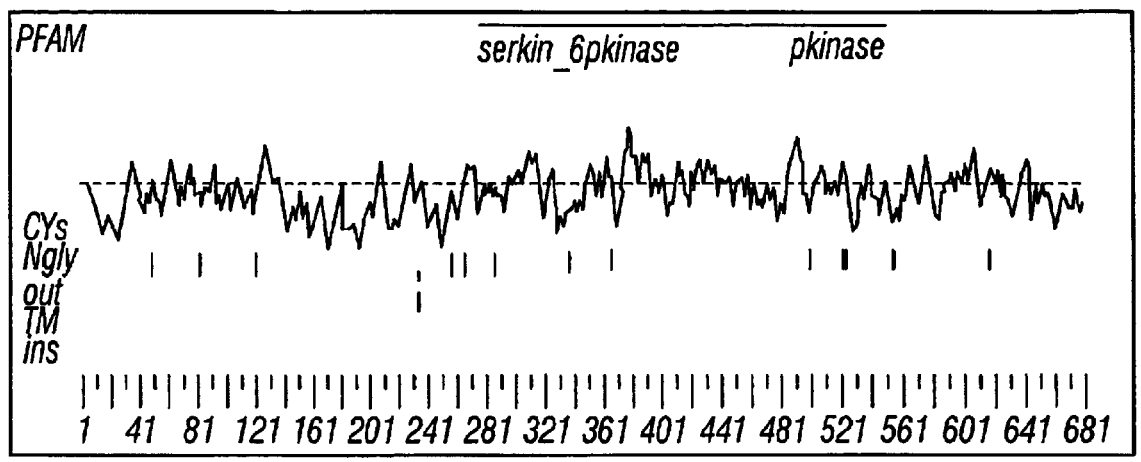

Analysis of 14790 (1649 aa)

>14790
MAGGRGAPGRGRDEPPESYPQRQDHELQALEAIYGADFQDLRPDACGPV
KEPPEINLVLYPQGLTGEEVYVKVDLRVKCPPTYPDVVPEIELKNAKGL
SNESVNLLKSRLEELAKKHCGEVMIFELAYHVQSFLSEHNKPPPKSFHE
EMLERRAQEEQQRLLEAKRKEEQEQREILHEIQRRKEEIKEEKKRKEMA
KQERLEIASLSNQDHTSKKDPGGHRTAAILHGGSPDFVGNGKHRANSSG
RSRREROYSVCNSEDSPGSCEILYFNMGSPDQLMVHKGKCIGSDEQLGK
LVYNALETATGGFVLLYEWVLQWQKKMGPFLTSQEKEKIDKCKKQIQGT
ETEFNSLVKLSHPNVVRYLAMNLKEQDDSIVVDILVEHISGVSLAAHLS
HSGPIPVHQLRRYTAQLLSGLDYLHSNSVVHKVLSASNVLVDAEGTVKI
TDYSISKRLADICKEDVFEQTRVRFSDNALPYKTGKKGDVWRLGLLLLS
LSQGQECGEY

FIG. 7A

Score = 49 (22.3 bits), Expect 34., Sum P(2) = 1.0
Identities = 12/39 (30%), Positives = 24/39 (61%)

Query: 507 DLPADFQDFLKKCVCLD-DKERWSPQQLLKHS-FI 539
            ++   + +D LKKC+   D +K R +  +++L+H   F+
Sbjct: 385 EVSQEAKDLLKKCLQKDPEKRRPTFEEILQHPWFL 419

Query: 540 NPQP 543
            P
Sbjct: 420 MRNP 423   SEQ.ID NO: 27

Score = 40 (19.1 bits), Expect = 0.0010, Sum P(3)
= 0.0010 Identities = 8/11 (72%), Positives = 9/11
(81%)

Query: 596 LGKGAFGAVIK 606
            LG G+FGAV K
Sbjct:   2 LGTGSFGAVYK  12   SEQ.ID NO: 28

---

View Prodom 150228

>150228 p99.2 (1) O74297_NEUCR //CPC3 PROTEIN
Length = 108

Score = 90 (36.7 bits), Expect = 0.0039, P =
0.0039 Identities = 32/105 (30%), Positives =
43/105 (40%)

Query: 1105 MDHSGMLVMLPFDLRIPFARYVAR--NNILN 1133
             +D +G ++ LPFDL +   AR +AR  N+ +
Sbjct:    3 LDQNGTVLQLPFDLMMGHARSLARITNSPVV   33

Query: 1134 LKRYCIERVFRPRKLDRFHPKELLECAFDIVT 1165
              K Y     +FR R     P   E   FDIVT
Sbjct:   35 QKSYSFGNIFRDRH-GGGQPDVYGEVDFDIVP   65

Query: 1166 STTNSF-LPXXXXXXXXXXXXQEFPALQERNY 1196

FIG. 7A1

```
                    S  L                 FP +
Sbjct:   66 SDALDLALKEAEVIKVLDEIATAFPTVSSTPI   97

Query: 1197 SIYLNHTMLL   1206
            L H+  LL
Sbjct:   97 CFQLGHSDLL   106    SEQ.ID NO: 29
```

View Prodom 13771

>137719 p99.2(1) O74297_NUCR //CPC3 PROTEIN Length = 304

Score = 87 (35.7 bits), Expect 0.61, Sum P(2) = (0.45)Identities=41/146 (26%), Positives = 64/156 (41%)

```
Query:   19 YPQRQDHELQALEAIYGADFQDLRPDACGPVKEPP   53
            Y + Q+ E+  L+AIYG DF            K P
Sbjct:   44 YQEVQESEVMVLQAIYGEDFTQHEAAHGAWQKSEP   78

Query:   54 EINLVLYPQGLTGEEVYVKVDLRVKCPPTYPDVVP   88
            ++  + P   + +E+   V L V      TYP  P
Sbjct:   79 RFDIKIKPS--SDQEL--SVTLGVVMVATYPKTPP   109

Query:   89 EIELKNAKGLSNESVNLLKSRLEELAKK---HCGE   120
            + +K+    L ES    +  E K        +
Sbjct:  110 LLTIKDDHSL-RESTKFKIQKFVETQPKIYAQAEQ   143

Query:  121 VMIFELAYHVQSFLSE--HNK------PP---PKS  144
            MI ++    ++  L E    K       P    ++
Sbjct:  144 EMIDQIVEGIRDILEEAAQKKVQGLEIPSLEEERA  178

Query:  145 FHEEMLERRAQEEQQR   160
            HE  L R AQ E++R
Sbjct:  179 AHEAELARLAQSEKER   194   SEQ.ID NO: 30
```

Score = 49 (22.3 bits), Expect =0.61, Sum P(2) = 0.45 Identities = 13/48 (27%), Positives = 27/48 (56%)

FIG. 7A2

```
Query:  1458 EGSHVKVKSFEKERQTEKRVLETELVDHVL 1487
             E    ++   EKER+  K++ E++   +  VL
Sbjct:   181 EAELARLAQSEKEREERKKLEESKEEERVL 210

Query:  1488 QK-LRTKVTDERNGREAS    1504
             +   L+ ++   +RN   + S
Sbjct:   211 EDMLQEELKRQRNKAKES    228  SEQ.ID NO: 31
```

Score = 49 (22.3 bits), Expect =0.61, Sum P(2) = 0.45 Identities = 13/48 (27%), Positives = 27/48 (56%)

```
Query:   238 KHRANSSGRSRRERQYSVCNSEDSPGSC-EIL 268
             +++A S + R  Q   S +      PG   E L
Sbjct:   222 RNKAKESRKKNRSHQLSPDRAPQDPGETDETL 253

Query:   269 YFNMGSPDQLMVHKGKCIGSDEQLGKLVY 297
             F+    P ++     G +       +GK V+
Sbjct:   254 MFDQ--PCKITDGSGNALFFQTVIGKTVF 280
                                      SEQ.ID NO: 32
```

Score = 47 (21.6 bits), Expect = 0.96, Sum P(2) = 0.62 Identities = 19/83 (22%), Positives = 33/83 (39%)

```
Query:   750 LPASDSESDIIFDNEDENSKSQ-NQDEDCNEKNGC 783
             L  S  E  ++ D   E K Q N+ ++   +KN
Sbjct:   200 LEESKEEERVLEDMLQEELKQRQRNYAKESRKKNR 234

Query:   784 HESEPSVTTEAVHYLYIQMEYCEKSTLRDTIDQGL 818
             H+  P   +            + + +    + D     L
Sbjct:   235 HQLSPDRAPQDPGETDETLMFDQPCKITDGSGNAL 269

Query:   819 YRDTVRLWRLFRE 831
             +   TV     +FRE
Sbjct:   270 FFQTVIGKTVFRE 282   SEQ.ID NO: 33
```

FIG. 7A3

```
SPEDSGGQDYVETVIPSNRLPSAAFFSETQRQFSRYFIEFEELQLLGKGA
FGAVIKVQNKLDGCCYAVKRIPINPASRQFRRIKGEVTLLSRLHHENIVR
YYNAWIERHERPAGPGTPPPDSGPLAKDDRAARGQPASDTDGLDSVEAAA
PPPILSSSVEWSTSGERSASARFPATGPGSSDDEDDDEDEHGGVFSQSFL
PASDSESDIIFDNEDENSKSQNQDEDCNEKNGCHESEPSVTTEAVHYLYI
QMEYCEKSTLRDTIDQGLYRDTVRLWRLFREILDGLAYIHEKGMIHRDLK
PVNIFLDSDDHVKIGDFGLATDHLAFSADSKQDDQTGDLIKSDPSGHLTG
MVGTALYVSPEVQGSTKSAYNQKVDLFSLGIIFFEMSYHPMVTASERIFV
LNQLRDPTSPKFPEDFDDGEHAKQKSVISWLLNHDPAKRPTATELLKSEL
LPPPQMEESELHEVLHHTLTNVDGKAYRTMMAQIFSQRISPAIDYTYDSD
ILKGNFSIRTAKMQQHVCETIIRIFKRHGAVQLCTPLLLPRNRQIYEHNE
AALFMDHSGMLVMLPFDLRIPFARYVARNNILNLKRYCIERVFRPRKLDR
FHPKELLECAFDIVTSTTNSFLPTAEIIYTIYEIIQEFPALQERNYSIYL
NHTMLLKAILLHCGIPEDKLSQVYIILYDAVTEKLTRREVEAKFCNLSLS
SNSLCRLYKFIEQKGDLQDLMPTINSLIKQKTGIAQLVKYGLKDLEEVVG
LLKKLGIKLQVLINLGLVYKVQQHNGIIFQFVAFIKRRQRAVPEILAAGG
RYDLLIPQFRGPQALGPVPTAIGVSIAIDKISAAVLNMEESVTISSCDLL
VVSVGQMSMSRAINLTQKLWTAGITAEIMYDWSQSQEELQEYCRHHEITY
VALVSDKEGSHVKVKSFEKERQTEKRVLETELVDHVLQKLRTKVTDERNG
REASDNLAVQNLKGSFSNASGLFEIHGATVVPIVSVLAPEKLSASTRRRY
ETQVQTRLQTSLANLHQKSSEIEILAVDLPKETILQFLSLEWDADEQAFN
TTVKQLLSRLPKQRYLKLVCDEIYNIKVEKKVSVLFLYSYRDDYYRILF
```

---

PSORT Prediction of Protein Localization

MITDISC:  discrimination of mitochondrial
targeting seq
    R content:        3      Hyd Moment(75): 7.37
    Hyd Moment(95): 6.02   G content:      5
    D/E content:    2      S/7 content:    0

Gavel: prediction of cleavage sites for
mitochondrial preseq
    R-2 motif at 20  GRG:RD MUCDISC:  discrimination of nuclear localization
signals
    pat4:   KKRK (5) at   190

*FIG. 7B*

```
pat4:       RPRK (4) at 1144
pat7:       none
bipartite:  RRAQEEQQRLLEAKRKE at 152
bipartite:  KRIPINPASRQFRRIKG at 619
content of basic residues: 12:11
NLS Score:  1.08
```

ER Membrane Retention Signals:

XXRR-like motif in the N-terminus: AGGR

None

Final Results (k = 9/23):

```
56.5 %: nuclear
30.4 %: cytoplasmic
 4.3 %: vacuolar
 4.3 %: mitochondrial
 4.3 %: vesicles of secretory system
``` prediction for 14790 is nuc (k=23)

| Start | End | Feature | Seq |
|---|---|---|---|
| 144 | 204 | coiled coil | FHEEMLERRA...AKQERLEIAS |

Signal Peptide Predictions for 14790

| Method | Predict | Score | Mat@ |
|---|---|---|---|
| SignalP (eukaryote) | NO | | |

Note: amino-terminal 70aa used for signal peptide prediction

Transmembrane Segments Predicted by MEMSAT

| Start | End | Orient | Score |
|---|---|---|---|
| 1522 | 1538 | ins-->out | 0.8 |

*FIG. 7C*

>14790
MAGGRGAPGRGRDEPPESYPQRQDHELQALEAIYGADFQDLRPDACGPVK
EPPEINLVLYPQGLTGEEVYVKVDLRVKCPPTYPDVVPEIELKNAKGLSN
ESVNLLKSRLEELAKKHCGEVMIFELAYHVQSFLSEHNKPPPKSFHEEML
ERRAQEEQQRLLEAKRKEEQEQREILHEIQRRKEEIKEEKKRKEMAKQER
LEIASLSNQDHTSKKDPGGHRTAAILHGGSPDFVGNGKHRANSSGRSRRE
RQYSVCNSEDSPGSCEILYFNMGSPDQLMVHKGKCIGSDEQLGKLVYNAL
ETATGGFVLLYEWVLQWQKKMGPFLTSQEKEKIDKCKKQIQGTETEFNSL
VKLSHPNVVRYLAMNLKEQDDSIVVDILVEHISGVSLAAHLSHSGPIPVH
QLRRYTAQLLSGLDYLHSNSVVHKVLSASNVLVDAEGTVKITDYSISKRL
ADICKEDVFEQTRVRFSDNALPYKTGKKGDVWRLGLLLLSLSQGQECGEY
PVTIPSDLPADFQDFLKKCVCLDDKERWSPQQLLKHSFINPQPKMPLVEQ
SPEDSGGQDYVETVIPSNRLPSAAFFSETQRQFSRYFIEFEELQLLGKGA
FGAVIKVQNKLDGCCYAVKRIPINPASRQFRRIKGEVTLLSRLHHENIVR
YYNAWIERHERPAGPGTPPPDSGPLAKDDRAARGQPASDTGLDSVEAAA
PPPILSSSVEWSTSGERSASARFPATGPGSSDDEDDDEDEHGGVFSQSFL
PASDSESDIIFDNEDENSKSQNQDEDCNEKNGCHESEPSVTTEAVHYLYI
QMEYCEKSTLRDTIDQGLYRDTVRLWRLFREILDGLAYIHEKGMIHRDLK
PVNIFLDSDDHVKIGDFGLATDHLAFSADSKQDDQTGDLIKSDPSGHLTG
MVGTALYVSPEVQGSTKSAYNQKVDLFSLGIIFFEMSYHPMVTASERIFV
LNQLRDPTSPKFPEDFDDGEHAKQKSVISWLLNHDPAKRPTATELLKSEL
LPPPQMEESELHEVLHHTLTNVDGKAYRTMMAQIFSQRISPAIDYTYDSD
ILKGNFSIRTAKMQQHVCETIIRIFKRHGAVQLCTPLLLPRNRQIYEHNE
AALFMDHSGMLVMLPFDLRIPFARYVARNNILNLKRYCIERVFRPRKLDR
FHPKELLECAFDIVTSTTNSFLPTAEIIYTIYEIIQEFPALQERNYSIYL
NHTMLLKAILLHCGIPEDKLSQVYIILYDAVTEKLTRREVEAKFCNLSLS
SNSLCRLYKFIEQKGDLQDLMPTINSLIKQKTGIAQLVKYGLKDLEEVVG
LLKKLGIKLQVLINLGLVYKVQQHNGIIFQFVAFIKRRQRAVPEILAAGG
RYDLLIPQFRGPQALGPVPTAIGVSIAIDKISAAVLNMEESVTISSCDLL
VVSVGQMSMSRAINLTQKLWTAGITAEIMYDWSQSQEELQEYCRHHEITY
VALVSDKEGSHVKVKSFEKERQTEKRVLETELVDHVLQKLRTKVTDERNG
REASDNLAVQNLKGSFSNASGLFEIHGATVVPIVSVLAPEKLSASTRRRY
ETQVQTRLQTSLANLHQKSSEIEILAVDLPKETILQFLSLEWDADEQAFN
TTVKQLLSRLPKQRYLKLVCDEIYNIKVEKKVSVLFLYSYRDDYYRILF

FIG. 7D

Prosite Pattern Matches for 14790

Prosite version:   Release 12.2 of February 1995

>PS00021|PDOC00001|ASN_GLYCOSYLATION N-glycosylation site.

| | | | |
|---|---|---|---|
| Query: | 100 | NESV | 103 |
| Query: | 242 | NSSG | 245 |
| Query: | 1055 | NFSI | 1058 |
| Query: | 1195 | NYSI | 1198 |
| Query: | 1201 | NHTM | 1204 |
| Query: | 1246 | NLSL | 1249 |
| Query: | 1414 | NLTQ | 1417 |
| Query: | 1518 | NASG | 1521 |
| Query: | 1600 | NTTV | 1603 |

>PS00004|PDOC00004|CAMP_PHOSPHO_SITE cAMP- and cGMP-dependent protein kinase phosphorylation site.

| | | | |
|---|---|---|---|
| Query: | 403 | RRYT | 406 |
| Query: | 988 | KRPT | 991 |
| Query: | 1630 | KKVS | 1633 |

>PS00005|PDOC00005|PKC_PHOSPHO_SITE protein kinase C phosphorylation site.

| | | | |
|---|---|---|---|
| Query: | 212 | TSK | 214 |
| Query: | 244 | SGR | 246 |
| Query: | 247 | SRR | 249 |
| Query: | 438 | TVK | 440 |
| Query: | 447 | SKR | 449 |
| Query: | 475 | TGK | 477 |
| Query: | 567 | SNR | 569 |
| Query: | 579 | TQR | 581 |
| Query: | 720 | SAR | 722 |
| Query: | 809 | TLR | 811 |
| Query: | 822 | TVR | 824 |
| Query: | 915 | STK | 917 |
| Query: | 945 | SER | 947 |
| Query: | 959 | SPK | 961 |

*FIG. 7E*

```
Query:   1036   SQR    1038
Query:   1057   SIR    1059
Query:   1060   TAK    1062
Query:   1232   TEK    1234
Query:   1236   TRR    1238
Query:   1416   TQK    1418
Query:   1455   SDK    1457
Query:   1473   TEK    1475
Query:   1545   STR    1547
Query:   1602   TVK    1604
Query:   1639   SYR    1641
```

>PS00006|PDOC00006|CK2_PHOSPHO_SITE Casein kinase II phosphorylation site.

```
Query:     65   TGEE    68
Query:     82   TYPD    85
Query:    108   SRLE   111
Query:    144   SFHE   147
Query:    207   SNQD   210
Query:    213   SKKD   216
Query:    247   SRRE   250
Query:    326   TSQE   329
Query:    343   TETE   346
Query:    411   SGLD   414
Query:    551   SPED   554
Query:    688   SDTD   691
Query:    707   SSVE   710
Query:    713   TSGE   716
Query:    730   SSDD   733
Query:    753   SDSE   756
Query:    809   TLRD   812
Query:    880   SKQD   883
Query:    943   TASE   946
Query:    991   TATE   994
Query:   1020   TNVD  1023
Query:   1180   TIYE  1183
Query:   1236   TRRE  1239
```

*FIG. 7F*

```
Query:  1395  SSCD    1398
Query:  1435  SQEE    1438
Query:  1455  SDKE    1458
Query:  1570  SEIE    1573
Query:  1639  SYRD    1642
```

>PS00007|PDOC00007|TYR_PHOSPHO_SITE Tyrosine kinase phosphorylation site.

```
Query:  246   RSRRERQY   253
Query:  811   RDTIDQGLY  819
Query:  830   REILDGLAY  838
Query:  1444  RHHEITY    1450
Query:  1617  KLVCDEIY   1624
```

>PS00008|PDOC00008|MYRISTYL N-myristoylation site.

```
Query:  218   GGHRTA  223
Query:  384   GVSLAA  389
Query:  494   CQECGE  499
Query:  599   GAFGAV  604
Query:  613   GCCYAV  618
Query:  684   GQPASD  689

Query:  742   GGVFSQ  747
Query:  782   GCHESE  787
Query:  900   GMVGTA  905
Query:  914   GSTKSA  919
Query:  1373  GVSIAI  1378
Query:  1514  GSFSNA  1519
```

>PS00009|PDOC00009|AMIDATION Amidation site.

```
Query:  475   TGKK   478
```

>PS00107|PDOC00100|PROTEIN_KINASE_ATP Protein kinases ATP-binding region signature.

*FIG. 7G*

Query: 596   LGKGAFGAV   604

>PS00108|PDOC00100|PROTEIN_KINASE_ST
Serine/Threonine protein kinases active-site signature.

Query: 844   MIHRDLKPVNIFL   856

>PS00116|PDOC00107|DNA_POLYMERASE_B DNA polymerase family B signature.

Query: 687   ASDTDGLDS   695

---

Protein Family / Domain Matches, HMMer version 2

Searching for complete domains in PFAM
Hmmpfam   search a single seq against HMM database
HMMER: 2.1.1 (Dec 1998)
Copyright (C) 1992-1998 Washington University School of Medicine
HMMER is freely distributed under the GNU General Public License (GPL).
--------------------------------
HMM file:        /prod/ddm/seqanal/PFAM/pfam4.4/Pfam
Sequence file: /prod/ddm/wspace/orfanal/oa-script.16895.seq
--------------------------------

Query: 14790

Scores for sequence family classification (score includes all domains):
Model             Description
--------          -----------
pkinase           Eukaryotic protein kinase domain
Ribosomal L23     Ribosomal protein L23
mRNA_cap_enzyme   mRNA capping enzyme

*FIG. 7H*

```
                  Score      E-value    N
                  -----      -------    ---
pkinase           282.0      7.8e-81    4
Ribosomal_L23       5.0          3.9    1
mRNA_cap_enzyme  -181.3          9.6    1

Parsed for domains:
Model            Domain   seq-f  seq-t   hmm-f  hmm-t
--------         ------   -----  -----   -----  -----
pkinase          1/4        332    443 ..    30   134..
pkinase          2/4        501    539 ..   237   278.]
pkinase          3/4        590    662 ..     1    66 [.
pkinase          4/4        797   1001 ..    65   278.]
Ribosomal_L23    1/1       1223   1244 ..     1    23 [.
mRNA_cap_enzyme  1/1       1004   1309 ..     1   504 []

Score      E-value
                  -----      -------
pkinase            69.4      3.7e-18
pkinase            22.8      3.2e-05
pkinase            51.2      4.2e-13
pkinase           138.7      1.1e-37
Ribosomal_L23       5.0          3.9
mRNA_cap_enzyme  -181.3          9.6
```

Alignments of top-scoring domains:
Pkinase: domain 1 of 4, from 332 to 443: score 69.4, E = 3.7e-18

```
              *->ilk..kesls..lrEiqilkrlsHpNIvrllg
                 ++++ k++++++ +E    l +lsHpN+vr+l
   14790 332  KIDkcKKQIQgtETEFNSLVKLSHPNVVRYLA 363 vfed...tddhlylvmEymegGdLfdylrrngpls
              +      +++++ + + E+  g +L+ +l+   gp++
   14790 364  MNLKeqdDISVVDILVEHISGVSLAAHLSHSGPIP 398 ekeakkialQilrGleYLHsngivHRDLKpeNILl
              +++++++ Q+l+Gl+YLHsn++vH   L ++N+L+
```

FIG. 7I

```
14790  399  VHQLRRYTAQLLSGLDYLHSNSVVHKVLSASNVLV  433 dengtvKiaD<-*  SEQ. ID NO: 8
            d +gtvKi+D
14790  434  DAEGTVKITD         443 pkinase:  domain 2 of 4, from 501 to 539: score
22.8, E = 3.2e-5

*->rlplpsncSeelkdLlkkcLnkDPskRpGsat
               +  +ps ++ +++d+lkkc ++D ++R+    +
14790  501     PVTIPSDLPADFQDFLKKCVCLDDKERW---S   529 akeilnhpwf<-*  SEQ. ID NO: 9
            +++l+h ++
14790  530  PQQLLKHSFI  539 pkinase:  domain 3 of 4, from 590 to 662: score
51.2, E = 4.2e-13

*->yelleklGeGsfGkVykakhk.tgkivAvKil
               +e l+ lG+G+fG V k+++k +g+ +AvK +
14790  590     FEELQLLGKGAFGAVIKVQNKlDGCCYAVKRI   621 kkesls......lrEiqilkrlsHpNIvrllgvfe
            +       s++ ++    E+ +l rl+H+NIvr++ ++
14790  622  PINPASrqfrriKGEVTLLSRLHHENIVRYYNAWI  656
```

FIG. 7J

```
                dtddhl<-* SEQ. ID NO: 10
                ++++++
14790  657      ERHERP           662 pkinase:  domain 4 of 4, from 797 to 1001: score
138.7, E = 1.1e=37

*<-hlylvmEymegGdLfdylrrngplsekeakki
                   +ly+ mEy+e+  L+d + +   + +    + ++
14790  797      YLYIQMEYCEKSTLRDTIDQGLYRDTVRLWRL    828 alQilrGleYLHsngivHRDLKpeNILldengtvK
                +++il Gl+Y+H++g +HRDLKp NI+ld++ +vK
14790  829      FREILDGLAYIHEKGMIHRDLKPVNIFLDSDDHVK   863 iaDFGLArll..................ekl
                i+DFGLA++    + +++++++++   +++++++l
14790  864      IGDFGLATDHlafsadskqddqtgdliksdpsGHL   898 ttfvGTpwYmmAPEvileg...rgysskvDvWSlG
                t+ vGT   Y+  +PEv  +g++++ Y   kvD  SlG
14790  899      TGMVGTALYV-SPEV--QGstkSAYNQKVDLFSLG   930 viLyElltggplfpgadlpaftggdevdqliifvl
                +i++E+
14790  931      IIFFEMS------------------------      937 klPfsdelpktridpleelfrikkr....rlplps
                   P              e++f +++ ++++ +++p+
```

*FIG. 7K*

```
14790  938  YHPMV--------TASERIFVLNQLrdptSPKFPE  964 ncSee....lkdLlkkcLnkDPskRpGsatakeil
              +  +  ++  +  k++++++Ln DP+kRp    ta+e+l
14790  965  DFDDGehakQKSVISWLLNHDPAKRP---TATELL  996 nhpwf<-* SEQ. ID NO: 11
              ++   +
14790  997  KSELL          1001
```

Ribosomal_L23: domain 1 of 1, from 1223 to 1244:
score 5.0, E = 3.9

```
              *->tdiikyPviTeKlamnlleepNk<-*
                              ↑SEQ. ID NO: 12
              ++ii  y  +TeKl+++++e   ++
14790  1223     VYIILYDAVTEKLTRREVEA-KF     1244
```

RNA_cap_enzyme: domain 1 of 1, from 1004 to 1309:
score -181.3, E = 9.6

```
              *->nqtteRvyelhkiElfsvpelnGKKiglgi
                    q++e              +  e+       l
14790  1004     PQMEES----------ELHEV-----LHH  1017 kLpktdteslrtmVakllglamktktfPddeGs
              L+++d++   rtm a+            + P   +
14790  1018  TLTNVDGKAYRTMMAQIFS----QRISPAIDYT  1046 qPVsferkdleesLkekdyfvceKTDGircshg
              +    + + ++             vce    ir+
14790  1047  YDSDILKGNFSIRTAKMQQHVCETI--IRI---  1074

FNRTGFLIAaLlFlvehpgleeaiSHiLSgef.
                           +  +h  +             +++
14790  1075  -------------FKRHGAVQL--------CTp  1086

.lidReknyYKQDYIDllpkrlfPrekdktkak
               l+  R    +Y       ++ ++ lf
14790  1087  lLLPRNRQIY-----EHNEAALFMD--------  1106
```

*FIG. 7L*

```
              elptyhrgtllDGElvidinriaveqkTlrYvv
                + + l++ l  d       ++    rYv
14790  1107   ------HSGMLVM-LPFD----LRIPF-ARYVA  1127

FDalaisGqtviqrd.lskrLgdefikavkKpf
               ++   ++ +   i+r    +  L+    f
14790  1128   RNNILNLKRYCIERVfRPRKLDR-F------HP  1153 defkkvmpdakilnqqkYNFpfkiglkhmslsy
              +e+     d+++++        f++  +   ++y
14790  1154   KELLECAFDIVTSTT----NSFLPTAEIIYTIY  1182 gqlkllkaeskmviskadampkllHinDGlIft
              ++    +   a                  +
14790  1183   EIIQEFPA----------------L--------  1191 cvrdtpyieGeiLVEPGNSYlDfnLlKWKPkee
                 ++++i+              +  LlK
14790  1192   QE-RNYSIYL---------NHTMLLKA-----  1208 nTvDFelilefeevndPeldekdgfslyLdYda
                +l   +                +e++
14790  1209   -----ILLHCG-------IPEDK----------  1219 mpGELfkfslgVWqgGfnkrFevihtdqiffrv
                 + ++++         +    ++++++      v
14790  1220   ------LSQVYIILY-DAVTEKLTRRE-----V  1240 afqklgRlkhefaelsVsdkdwyklkaleqpld
              ++          f  +ls+s       +l
14790  1241   EAK-------FCNLSLSSNSLCRLY-------  1258

GrIVEcrladieilIFQegrWeylrfRdDKqqa
              +++E  ++  +              + ++  +   q+
14790  1259   -KFIEQKGDLQD--------LMPTINSLIKQK  1281 lKtgGYsgNhistvekvllsikDgvsiEeLlkl
                tg              +++v    kD  +Ee+   l
14790  1282   --TG--------IAQLVKYGLKD---LEEVVGL  1301
```

*FIG. 7M*

```
                    fpGmyFAGAktlikr<-*  SEQ. ID NO: 13
                       k +ik
14790  1302   LK-------KLGIKL      1309
```

//
Searching for complete domains in SMART
hrmpfam - search a single seq against HMM database
HMMER 2.1.1 (Dec 1998)
Copyright (c) 1992-1998 Washington University
School of Medicine
HMMER is freely distributed under the GNU General
Public License (GPL).
----------
HMM file: /ddm/robison/smart/smart/smart.all.hmms
Sequence file: /prod/ddm/wspace/orfanal/oa-
script.16895.seq
----------
Query: 14790

Scores for sequence family classification (score
includes all domains):

| Model | Description | Score | E-value | N |
|-------|-------------|-------|---------|---|
| serkin_6 |  | 184.2 | 2.2e-51 | 2 |
| tyrkin_6 |  | -40.3 | 2e-09 | 1 |

Parsed for domains:

| Model | Domain | seq-f | seq-t | hmm-f | hmm-t |  |
|-------|--------|-------|-------|-------|-------|--|
| serkin_6 | 1/2 | 286 | 539.. | 1 | 231 | [] |
| serkin_6 | 2/2 | 590 | 1001.. | 1 | 231 | [] |
| tyrkin_6 | 1/1 | 590 | 1001.. | 1 | 280 | [] |

| Model | score | E-value |
|-------|-------|---------|
| serkin_6 | 17.2 | 2.2e-11 |
| serkin_6 | 166.8 | 3.5e-46 |
| tyrkin_6 | -40.3 | 2e-09 |

FIG. 7N

Alignments of top-scoring domains:

serkin_6: domain 1 of 2, from 286 to 539: score 17.2, E = 2.2e-11

```
                *->YellkklGkGaFGkVylardkktgrlvAiKvi
                   ++lGk      Vy a ++ tg  v      +
      14790 286    IGSDEQLGK----LVYNALETATGGFV---LL    310 k........................erilr
                   +    +  +++ ++  +++++++ ++ +++ + ++
      14790 311    YewvlqwqkkmgpfltsqekekidkckkqiQGTET  345

EikiLkk.dHPNIVkLydvfed.....dklylVmE
                   E + L k  HPN+V+++ +      +++++ + +   E
      14790 346    EFNSLVKlSHPNVVRYLAMNLKeqddsIVVDILVE  380 yceGdlGdLfdlkkrgrrglrkvlsE.earfyfr
                   +++G   +L  +l +  g+        ++ ++ r+y++
      14790 381    HISG--VSLAAHLSHSGP------IPVhQLRRYTA  407

QilsaLeYLHsqgIiHRDLKPeNiLLds..hvKla
                   Q+ls+L+YLHs+ ++H   L  +N+L+d +++vK++
      14790 408    QLLSGLDYLHSNSVVHKVLSASNVLVDAegTVKIT  442

DFGlArql..........ttfvGTpeYmAPEvl..
                   D  ++++l +   +++    + t v          +++
      14790 443    DYSISKRLadickedvfeQTRV---------RFsd  468

.....gYgkpavDiWSlGcilyElltGkpPFpqld
                        +   +  +  gk + D+W lG +l  l   G+
      14790 469    nalpyKTGK-KGDVWRLGLLLLSLSQGQE-----C  497 lifkkig....SpeakdLikklLvkdPekRlta.e
                   + +    +++   +  ++ d++kk+ +  d ++R++ ++
      14790 498    GEYPVTIpsdlPADFQDFLKKCVCLDDKERWSPqQ  532 aLedeldikaHPFF<-*   SEQ. ID NO: 14
                   +L+        H  f+
      14790 533    LLK------HSFI       539
```

FIG. 70 serkin_6:  domain 2 of 2, from 590 to 1001: score 166.8, E = 3.5e-46

```
                *->YellkklGkGaFGkVylardkktgrlvAiKvi
                   +e l++lGkGaFG V ++++k +g   +A+K+i
14790    590       FEELQLLGKGAFGAVIKVQNKLDGCCYAVKRI    621 k...............................
                + ++ +++ ++ +++ +  ++ ++++  +   +
14790    622    Pinpasrqfrrikgevtllsrlhhenivryynawi   656

...................................
                ++++++ +++++++++++   ++++    ++++ ++++
14790    657    erherpagpgtpppdsgplakddraargqpasdtd   691

...................................
                + ++ +     +++    +++ + +++++++ + + +
14790    692    gldsveaaapppilsssvewstsgersasarfpat   726

...................................
                + ++ +     +++    +++ + +++++++ + + +
14790    727    gpgssddedddedehggvfsqsflpasdsesdiiF   761 rilrEikiLkk...dHPNIVkLydvfed......d
                + + E +   +++++d+    ++++  + +++   +
14790    762    DNEDENSKSQNqdeDCNEKNGCHESEPSvtteavH   796 klylVmEyceGdlGdLfdllkkrgrrglrkvlsE.
                +ly+ mEyce       +L+d +++ +        +
14790    797    HLYIQMEYCEK--STLRDTIDQGLY------RDTv   823 earfyfrQilsaLeYLHsqgIiHRDLKPeNiLLds
                + +++fr+il++L+Y+H++g iHRDLKP Ni+Lds
14790    824    RLWRLFREILDGLAYIHEKGMIHRDLKPVNIFLDS   858

..hvKlaDFGlArql....................
                ++hvK++DFGlA+      + ++++++++++  +++
14790    859    ddHVKIGDFGLATDHlafsadskqddqtgdliksd   893

.....ttfvGTpeYmAPEvl.....gYgkpavDiW
```

FIG. 7P

```
              ++++  t +vGT    Y++PEv  +++++gY+   +vD
14790  894  psghlTGMVGTALYVSPEVQgstksAYNQ-KVDLF    927

SlGcilyElltGkpPFp..qldlifkkig......
            SlG+i++E+ +   p      ++   ++++++++++++
14790  928  SLGIIFFEMSY-HPMVTasERIFVLNQLRdptspk     961

.........SpeakdLikklLvkdPekRlta.eaL
            +++ ++++       k+ i+ 1L+ dP+kR+ta+e+L
14790  962  fpedfddgeHAKQKSVISWLLNHDPAKRPTAtELL      996 edeldikaHPff<-*  SEQ. ID NO: 15
             +         + +
14790  997  K-------SELL            1001 tyrkin_6: domain 1 of 1, from 590 to 1001: score -
40.3, E = 2e-09

*->ltlgkklGeGaGFeVykGtlk...ieVAVKtL
               + ++ LG GaFG V k + k ++   AVK +
14790  590       FEELQLLGKGAFGAVIKVQNKldgCCYAVKRI   621 keda....keeFlrEakiMkklGgkHpNiVkLlGv
             +  +++ + +   E   ++++l  +H+NiV+ + +
14790  622  PINPasrqFRRIKGEVTLLSRL--HHENIVRYYNA    654 cteegrrFmevePlmivmEymegGdLldyLrknrp
            +e
14790  655  WIE------------------------RHERP     662 k..................................
             +++++++++++   ++++    ++++  +++++  ++  +
14790  663  Agpgtpppdsgplakddraargqpasdtgldsve    697

...................................
             +++ ++++ + +  +++++++ + + + +++++++
14790  698  aaapppilsssvewstsgersasarfpatgpgssd   732

```
14790  733  dedddedehggvfsqsflpasdsesdiifdneden        767

..................................
            +++++++++ +++++ +++++ +++   +     +
14790  768  sksqnqdedcnekngchesepsvtteavhylyiqm        802

...lslsdLlsfAlQIAkGMe
             +  ++++ +++ +++    + L        I +G +
14790  803  eycekstlrdtidqglyRDTVRLWRLFREILDGLA        837

YLesknfvHRDLAARNcLvgenkvvKIsDFGLsRd
            Y+++k+ +HRDL    N+ ++++ +vKI+DFGL+ d
14790  838  YIHEKGMIHRDLKPVNIFLDSDDHVKIGDFGLATD        872 lyddDkkG.....eskdyYrkkggkggktllPir.
             +    ++ +++++  +d +++   +++   +++
14790  873  HLAF-SADskqddQTGDLIKSDPSGHLTGMVGTAl        906

WmAPEsl..kdgkFtskSDVWSFGVlLWEiftlGe
             +PE+  ++ ++  ++ k D +S G+   +E+
14790  907  YVSPEVQgsTKSAYNQKVDLFSLGIIFFEM-----        936 qPYpgeiqqfmsnee...vleylkkGyRlpkPend
             Y +     ++++e+   vl++l++    ++ Pe+
14790  937  -SYHPM----VTASErifVLNQLRDPTSPKFPED-        965 lpiSs.vtCPdelYdlMlqCWaedPedRPtFsel.
              ++ +  +++     +++++    ++dP++RPt +el
14790  966  ----FdDGEHAKQKSVISWLLNHDPAKRPTATELl        996

.verl<-* SEQ. ID NO: 16
             + e+l
14790  997  kSELL        1001
```

*FIG. 7R*

ProDom Matches

| ProdomId | Start | End | Description | Score |
|---|---|---|---|---|
| View Prodom 40346 | 18 | 323 | p99.2 (2)001712(1)// INITIATION FACTOR KINASE EUKARYOCTIC-2 ALPHA EIF-2ALPHA | 295 |
| View Prodom 137719 | 19 | 1504 | p99.2(1)074297_NEUCR// CPC3 PROTEIN | 87 |
| View Prodom I | 341 | 1017 | p99.2(2773)CC2(14) KKIT (14) KPC(13)//KINASE PROTEIN TRANSFERASE ATP-BINDING SERIN/THREOINE-PROTEIN PHOSPHORYLATION RECEPTOR TYROSINE-PROTEIN PRECURSOR TRANSMEMBRANE | 107 |
| View Prodom 150228 | 1105 | 1206 | p99.2(1)074297_NEUCR// CPC3 PROTEIN | 90 |
| View Prodom 2305 | 1106 | 1230 | p99.2(23)SYH(12)// SYNTHETASE AMINOACYL-TRNA HISTIDYL-TRNA PROTEIN LIGASE ATP-BINDING BIOSYNTHESIS HISTIDINE-- TRNA HISRS KINASE | 137 |
| View Prodom 42726 | 1274 | 1648 | p99.2(2)0017121(1) 061651 (1)//INITIATION FACTOR KINASE EUKARYOTIC EIF-2 ALPHA EIF-2ALPHA | 221 |

*FIG. 7S*

```
View Prodom 40346
>40346 p99.2(2) O01712(1) O61651(1) //INITIATION
FACTOR KINASE EUKARYOTIC EIF-2 ALPHA EIF-2ALPHA
Length = 296

Score = 295(108.9 bits), Expect = 1.7e-28, Sum
P(2) = 1.7e-28 Identities = 58/144 (40%),
Positives = 95/144 (65%)

Query:   18 SYPQRQDHELQALEAIYGADFQDLRPDACGPVKEP      52
            S+ +RQ  EL+ +++I+G D +DLRP A    + +P
Sbjct:    9 SFRERQAQELEVIKSIFGCDVEDLRPQANPSLWKP      43

Query:   53 PEINLVLYP--QGLTGEEVYVKVDLRVKCPPTYPD      85
            +I + L P     G E YV   L V CP   YP
Sbjct:   44 TDIRIQLTPLRDSSNGLETYVCTKLHVTCPSKYPK      78

Query:   86 VVPEIELKNAKGLSNESVNLLKSRLEELAKKHCGE     120
            + P+I L+ +KG+S++ +   L+++L+   +++  GE
Sbjct:   79 LPPKISLEESKGMSDQLLEALRNQLQAQSQELRGE     113
```

FIG. 7T

```
Query: 121  VMIFELAYHVQSFLSEHNKPPPKSFHEEMLERRAQ  154
             VMI+ELA  VQ+FL EHNKPP  SF+++ML+ + +
Sbjct: 114  VMIYELAQTVQAFLLEHNKPPKGSFYDQMLDKQK   148

Query: 155  EEQQ  159
             +Q+
Sbjct: 149  RDQE  152  SEQ. ID NO: 17
```

Score = 63 (27.2 bits), Expect = 1.7e-28, Sum P(2) = 1.7e = 28 Identities = 15/59 (25%), Positives = 30/59 (50%)

```
Query: 266  EILYFN-MGSPDQLMVHKGKCIGSDEQLGKLVYNA  299
             E LYF+ MG       + +G C+G   ++ G + Y
Sbjct: 230  ETLYFHKMGR----QIQRGCCVGHSQR-GCIAYTG  259

Query: 300  LETATGGFVLLYEWVLQWQKKMGP      323
             ++    G  + + EW +++ +    P
Sbjct: 260  IDMHCGQLLYITEW?IKYSQLEQP      283
                                    †SEQ. ID NO: 18
```

View Prodom 42726

>42726 p99.2(2) O01712(1) O61651(1) //INITIATION FACTOR KINASE EUKARYOTIC EIF-2 ALPHA EIF-2ALPHA Length =469

Score = 221 (82.9 bits), Expect = 7.5e-15, P = 7.5e-15 Identities = 92/341 (26%), Positives 160/341 (45%)

fig 7i

```
Query: 1274  INSLIKQKTGIAQLVKYGLKDLEEXXXXXXXXX  1306
              + SL++ K   A L  +  L++LE
Sbjct:   70  LKSLMRGKGEAASLARGALRELETVVGLAYSLG   102

Query: 1307  XXXXXXXNLGLVYKVQQ--HNGIIFQFVAFIKR  1337
                     GL    +   + GI++Q A +K
Sbjct:  103  VKCPIHIWAGLPISFDRASNGGIVWQMTADLKP   135
```

FIG. 7U

```
Query:  1338  RQRAVPEILAAGGRYDLLIPQF-RGPQALGPVP  1369
                 +      P +LA G RYD ++ +F +   Q    P
Sbjct:   136  NRSGHPSVLAIGERYDSMLHEFQKQAQKFNPAM   168

Query:  1370  TAIGV------SIAIDKISAAVLNMEESVTISS  1396
              A GV           + ++DK+ AAV  +E +      +
Sbjct:   169  PARGVLSGAGLTFSLDKLVAAV-GVEYAKDCRA   200

Query:  1397  CDLLVVSVGQMSMSRAINLTQKL-WTAGITAEI  1428
              D+  +     G        + +      +L W+ GI   I
Sbjct:   201  IDVGICVCGTRPPLKDVTYIMRLLWSVGIRCGI  233

Query:  1429  MYDWSQSQEELQEYCRHHEITYVALVSDKEGSH  1461
                 +   S+    +E Q+    R   +  +V LV++   GS
Sbjct:   234  VEAASELGDEAQDLARLGAL-HVILVAEN-GS-  263

Query:  1462  VKVKSFEKERQTEKRVLETELVDHVLQKLRTKV  1494
              ++V+SFE+ER    E+  +    TELV+ +  +  LR+
Sbjct:   264  LRVRSFERERFQERHLTRTELVEFIQKMLRS--  294

Query:  1495  TDERNGREASDNLAVQNLKGSFSNAS-------  1520
              D  NG       DN  +   +  GS   N S
Sbjct:   295  -DGLNGTTV-DNFSHLSALGSGDNRSSGGKERE  325

Query:  1521  ----GLF-EIGHATV------VPIVSV--LAPE  1540
                  GL      AT+         +P + V   L  +
Sbjct:   326  RGENGLSTSASNATIKNNYSQLPNLQVTFLTHD  358

Query:  1541  KLSASTRRRYETQVQTRLQTSLANLHQKSSEIE  1573
              K +A+ +RR E QV  ++ ++L+   +K + +
Sbjct:   359  KPTANYKRRLENQVAQQMSSTLSQFLKKETFV-  390

Query:  1574  ILAVDLPKETI    1584
              +L V+LP      +
Sbjct:   391  VLVVELPPAVV    401   SEQ. ID NO: 19

Score = 150 (57.9 bits), Except = 4.2e-07, P =
4.2e-07  Identities = 66/300 (22%), Positives =
137/300 (45%)
```

FIG. 7V

```
Query:  1368  VPTAIGVSIAIDKISAAVLNMEESVTISSCDLL  1400
              V  +  G++ ++DK+ AAV  +E +    + D+
Sbjct:   173  VLSGAGLTFSLDKLVAAV-GVEYAKDCRAIDVG   204

Query:  1401  VVSVGQMSMSRAINLTQKL-WTAGITAEIMYDW  1432
              +  G     + +      +L W+ GI    I+
Sbjct:   205  ICVCGTRPPLKDVTYIMRLLWSVGIRCGIVEAA   237

Query:  1433  SQSQEELQEYCRHHEITYVALVSDKEGSHVKVK  1465
              S+  +E Q+  R    + +V LV++     V+
Sbjct:   238  SELGDEAQDLARLGAL-HVILVAENGSLRVRSF   269

Query:  1466  SFEK--ERQTEKRVLETELVDHVLQK--LRTKV  1494
               E+   ER   +  L  E +   +L+   L
Sbjct:   270  ERERFQERHLTRTEL-VEFIQKMLRSDGLNGTT   301

Query:  1495  TDERNGREA---SDNLAV------QNLKGSFSN  1518
              D  +    A      DN +         + G ++
Sbjct:   302  VDNFSHLSALGSGDNRSSGGKERERGENGLSTS   334

Query:  1519  ASGLFEIHGATVVPIVSV--LAPEKLSASTRRR  1549
              AS       +  + +P  + V  L  +K +A+ +RR
Sbjct:   335  ASNATIKNNYSQLPNLQVTFLTHDKPTANYKRR   367

Query:  1550  YETQVQTRLQTSLANLHQKSSEIEILAVDLPKE  1582
              E QV   ++  ++L+    +K  +   +L V+LP
Sbjct:   368  LENQVAQQMSSTLSQFLKKETFV-VLVVELPPA   399

Query:  1583  TILQFLSL--EWDADEQAFNTTVKQLLSRLPK-  1612
              +     +     +    +  ++   +   ++  R  K
Sbjct:   400  VVNAIVGAINPREIRKRETEPEINYVIERFSKY   432

Query:  1613  QRYLKLVCDEIYNIKVEKKVSVLFLYSYRDDYY  1645
              +RY+   +  +E+ +     + K  ++ LYS  D YY
Sbjct:   433  KRYISEINEEVVDYLSDAKTPIVALYSISDSYY   465

Query:  1646  RIL    1648
              R++
Sbjct:   466  RVI    468  SEQ. ID NO: 20
```

*FIG. 7W*

View Prodom 2305

>2305 p99.2 (23) SYH(12) // SYNTHETASE AMINOACYL-TRNA HISTIDYL-TRNA PROTEIN LIGASE ATP-BINDING BIOSYNTHESIS HISTIDINE--TRNA HISRS KINASE Length = 145

Score = 137 (53.3 bits), Expect = 3.9e-08, P = 3.9e-08 Identities = 41/131 (31%), Positives = 62/131 (47%)

```
Query: 1106  DHSGMLVMLPFDLRIPFARYVARNNI----LNL    1134
             D  G L+ L +DL +PFARYVA N +    L L
Sbjct:   18  DQGGELLSLRYDLTVPFARYVAMNLLKVTNLPL    50

Query: 1135  KRYCIERVFRPRK--LDRFHPKELLECAFDIVT    1165
             KRY I +V+R +   + R   +E  +C FDI+
Sbjct:   51  KRYHIAKVYRRDRPAMTRGRYREFYQCDFDII-    82

Query: 1166  STTNSFLPXXXXXXXXXXXXQEFPALQERNYSI    1198
             ++   P              +    + N+ I
Sbjct:   83  GEYDTMAPDAEILKILTEILSQLGIRELGNFKI    115

Query: 1199  YLNHTMLLKAILLHCGIPEDKLSQVYIILYDA    1230
             +NH  +L  ++L     P K  Q Y+  Y A
Sbjct:  116  KINHRGILDSLLQ----PWPKTLQEYLTQYKA    143
                                         ↑SEQ. ID NO: 21
```

View Prodom 1

>1 p99.2 (2773) CC2(14) KKIT(14) KPC1(13) //KINASE PROTEIN TRANSFERASE ATP-BINDING SERINE/THERONINE-PROTEIN PHOSPHORYLATION RECEPTOR TYROSINE-PROTEIN PRECURSOR TRANSMEMBRANE Length = 431

Score = 107 (42.7 bits), Expect = 0.0032, Sum P(2) = 0.0032 Identities = 36/106 (33%), Positives = 50/106 (47%)

FIG. 7X

```
Query:  848 DLKPVNIFLDSDDH------VK-IGDFGLATDHLA 875
             DLKP NI LD + H        +K I DFGLA +
Sbjct:  220 DLKPENILLDEESHENTPNMIKLIADFGLAKE--I 253

Query:  876 FSADSKQDDQTGDLIKSDPSGHLTGMVGTALYVS- 909
             +S+ S  ++ +             + M GT YVS
Sbjct:  254 YSSSSTYEEMSSSQAVFGSHQTTSTMCGTPYYVSM 288

Query:  910 ----PEVQGSTKSA-----YNQKVDLFSLGIIFFE 935
                 PE      SA      Y+ K D++S G+I +E
Sbjct:  289 KSMAPEYMAPESSATNYQKYSTKSDVWSFGVILYE 323

Query:  936 M 936
             M
Sbjct:  323 M 323 SEQ.ID NO: 22
```

Score = 105 (42.0 bits), Expect = 3.5e-05 Sum
P(3)=3.5e-05 Identities = 35/102 (34%), Positives
= 48/102 (47%)

```
Query:  824 RLWRLFREILDGLAYIHEK-----GMIHR----DL 849
             +L    +I  GL Y+H K      G+IHR    DL
Sbjct:  187 QLMHYVHQIAKGLEYLHSKNQKHQGIIHRAKKVDL 221

Query:  850 KPVNIFLDSDDH------VK-IGDFGLATDHLAFS 877
             KP NI LD + H       +K I DFGLA +  +S
Sbjct:  222 KPENILLDEESHENTPNMIKLIADFGLAKE--IYS 254

Query:  878 ADSKQDDQTGDLIKSDPSGHLTGMVGTALYVS 909
             + S  ++ +             + M GT YVS
Sbjct:  255 SSSTYEEMSSSQAVFGSHQTTSTMCGTPYYVS 286
                                         ↕SEQ.ID NO: 23
```

Score = 74 (31.1 bits), Expect = 0.91, Sum P(2) =
0.60 Identities = 30/127 (23%), Positives = 60/127
(47%)

```
Query:  341 QGTETEFNSLVKLSHPNVVRYLAMNLKEQDDSIVV 375
             +G+  E+  +     +  ++ L++    +  +++
Sbjct:  134 EGSLVEYMEYMSGGSEDYMKKLSLETVMKIAMMIL 168
```

FIG. 7Y

```
Query: 376  DIL-VEHISGVSLAAHLSHSGPIPVHQLRRYTAQL 409
             + + H+S  S  +   LSHS      QL Y Q+
Sbjct: 169  QFMQIMHMSSESES--LSHS------QLMHYVHQI 195

Query: 410  LSGLDYLHSNS-----VVHKV----LSASNVLVDA 435
            GL+YLHS +        ++H+     L  N+L+D
Sbjct: 196  AKGLEYLHSKNQKHQGIIHRAKKVDLKPENILLDE 230

Query: 436  EG------TVK-ITDYSISKRL 450
             E        +K  I D+ ++K +
Sbjct: 231  ESHENTPNMIKLIADFGLAKEI 252
                              ↑SEQ.ID NO: 24
```

Score = 65 (27.9 bits), Expect = 3.5e-05, Sum P(3) = 3.5e-05 Identities = 29/124 (23%), Positives = 50/124 (40%)

```
Query: 907  YVSPEVQGSTKSAYNQKVDLFSLGIIFFEM-SYHP 940
            Y++PE   +     Y+ K D++S G+I +EM   P
Sbjct: 294  YMAPESSATNYQKYSTKSDVWSFGVILYEMLTGKP 328

Query: 941  MVTASERIFVLNQLRDPTSPKFPEDFDDGEHAKQK 975
                  E    +++      S K  E    + G        +
Sbjct: 329  PFFPGES--EVSEEEPYQSMKNMEVLEMGPEETIQ 361

Query: 976  SVISWLLNHDPAKRPT-------------ATELLKS 998
            V+S ++     +  P                A +LLK
Sbjct: 362  KVMSKIVEKKGERMPQPSSSNCPEVSQEAKDLLKK 396

Query: 999  ELLPPPQMEESELHEVLHH 1017
             L   P+       E+L H
Sbjct: 397  CLQKDPEKRRPTFEEILQH 415 SEQ.ID NO: 25
```

Score = 55 (24.4 bits), Expect 3.5e-05, Sum P(3) = 3.5e-05 Identities = 12/23 (52%), Positives 18/23 (78%)

```
Query: 589  EFEELQ-LLGKGAFGAVIKVQNK 610
            ++E L+ LLGKG+FG V K ++K
Sbjct: 33   QYELLKKLLGKGSFGKVYKAKHK 55
                              ↑SEQ.ID NO: 26
```

FIG. 7Z

: # 14790, NOVEL PROTEIN KINASE MOLECULE AND USES THEREFOR

BACKGROUND OF THE INVENTION

Phosphate tightly associated with protein has been known since the late nineteenth century. Since then, a variety of covalent linkages of phosphate to proteins have been found. The most common involve esterification of phosphate to serine, threonine, and tyrosine with smaller amounts being linked to lysine, arginine, histidine, aspartic acid, glutamic acid, and cysteine. The occurrence of phosphorylated proteins indicates the existence of one or more protein kinases capable of phosphorylating amino acid residues on proteins, and also of protein phosphatases capable of hydrolyzing phosphorylated amino acid residues on proteins.

Kinases play a critical role in the mechanism of intracellular signal transduction. They act on the hydroxyamino acids of target proteins to catalyze the transfer of a high energy phosphate group from adenosine triphosphate (ATP). This process is known as protein phosphorylation. Along with phosphatases, which remove phosphates from phosphorylated proteins, kinases participate in reversible protein phosphorylation. Reversible phosphorylation acts as the main strategy for regulating protein activity in eukaryotic cells.

Protein kinases play critical roles in the regulation of biochemical and morphological changes associated with cell proliferation, differentiation, growth and division (D'Urso, G. et al. (1990) *Science* 250: 786–791; Birchmeier. C. et al. (1993) *Bioessays* 15: 185–189). They serve as growth factor receptors and signal transducers and have been implicated in cellular transformation and malignancy (Hunter, T. et al. (1992) *Cell* 70: 375–387; Posada, J. et al. (1992) *Mol. Biol. Cell* 3: 583–592; Hunter, T. et al. (1994) *Cell* 79: 573–582). For example, protein kinases have been shown to participate in the transmission of signals from growth-factor receptors (Sturgill, T. W. et al. (1988) *Nature* 344: 715–718; Gomez, N. et al. (1991) *Nature* 353: 170–173), cell cycle progression and control of entry of cells into mitosis (Nurse, P. (1990) *Nature* 344: 503–508; Maller, J. L. (1991) *Curr. Opin. Cell Biol.* 3: 269–275) and regulation of actin bundling (Husain-Chishti, A. et al. (1988) *Nature* 334: 718–721).

Kinases vary widely in their selectivity and specificity of target proteins. They still may, however, comprise the largest known enzyme superfamily. Protein kinases can be divided into two main groups based on either amino acid sequence similarity or specificity for either serine/threonine or tyrosine residues. Serine/threonine specific kinases are often referred to as STKs while tyrosine specific kinases are referred to as PTKs. A small number of dual-specificity kinases are structurally like the serine/threonine-specific group. Within the broad classification, kinases can be further sub-divided into families whose members share a higher degree of catalytic domain amino acid sequence identity and also have similar biochemical properties. Most protein kinase family members also share structural features outside the kinase domain that reflect their particular cellular roles. These include regulatory domains that control kinase activity or interaction with other proteins (Hanks, S. K. et al. (1988) *Science* 241: 42–52).

Almost all kinases contain a catalytic domain composed of 250–300 conserved amino acids. This catalytic domain may be viewed as composed of 11 subdomains. Some of these subdomains apparently contain distinct amino acid motifs which confer specificity as a STK or PTK or both. Kinases may also contain additional amino acid sequences, usually between 5 and 100 residues, flanking or occurring within the catalytic domain. These residues apparently act to regulate kinase activity and to determine substrate specificity. (Reviewed in Hardie, G. and Hanks, S. (1995) The Protein Kinase Facts Book, Vol I:7–20 Academic Press, San Diego, Calif.).

Approximately one third of the known oncogenes encode PTKs. PTKs may occur as either transmembrane or soluble proteins. Transmembrane PTKs act as receptors for many growth factors. Interaction of a growth factor to its cognate receptor initiates the phosphorylation of specific tyrosine residues in the receptor itself as well as in certain second messenger proteins. Growth factors found to associate with such PTK receptors include epidermal growth factor, platelet-derived growth factor, fibroblast growth factor, hepatocyte growth factor, insulin and insulin-like growth factors, nerve growth factor, vascular endothelial growth factor, and macrophage colony stimulating factor.

Soluble PTKs often interact with the cytosolic domains of plasma membrane receptors. Receptors that signal through such PTKs include cytokine, hormone, and antigen-specific lymphocytic receptors. Many PTKs were identified as oncogene products by the observation that PTK activation was no longer subject to normal cellular controls. Also, increased tyrosine phosphorylation activity is often observed in cellular transformation, or oncogenesis, (Carbonneau, H. and Tonks, N. K. (1992) Annu. Rev. Cell Biol. 8:463–93.) PTK regulation may therefore be an important strategy in controlling some types of cancer.

One example of regulation of a cellular function by reversible protein phosphorylation is in the case of eukaryotic initiation factor-2 (eIF-2). When phosphorylated by an eIF-2 kinase at the alpha subunit, eIF-2 is inhibited from continuing to participate in the initiation of protein translation, which leads to termination of protein synthesis. Thus inhibitors of eIF-2 phosphorylation are expected to be anti-proliferative in nature. This regulation of eIF-2 apparently plays a role in eukaryotic cells under viral infection, nutritional deprivation, and heat shock conditions. Phosphorylation of eIF-2 apparently also plays a role in programmed cell death.

Phosphorylation of eIF-2 may be controlled by regulating the eIF-2 kinase, which is activated by double-stranded RNA (dsI). Double stranded RNA is induced by interferon and represents an interferon mediated response to viral infection. Thus inhibitors of eIF-2 phosphorylation are expected to also be anti-viral in nature.

SUMMARY OF THE INVENTION

The present invention is based, at least in part, on the discovery of novel kinases referred to herein as 14790 proteins with similarities to known eIF-2 kinases, as well as nucleic acid molecules encoding the kinase. The kinase nucleic acid and protein molecules of the present invention are useful as modulating agents in regulating a variety of cellular processes, e.g., regulation of cell cycle, including cell proliferation, differentiation, growth and division. In particular, the kinase and its related nucleic acids will be advantageous in the regulation of any cellular function uncontrolled proliferation and differentiation, such as in cases of cancer. Other situations where the kinases of the invention are of particular advantage are in cases of autoimmune disorders or undesired inflammation.

Additionally, the kinases of the present invention, similar to known eIF-2 kinases, may play a role in cellular metabolism in response to conditions such as viral infection, nutritional deprivation, and heat shock conditions. As such, inhibitory modulators of the kinases are expected to be of benefit as anti-viral agents. A kinase of the invention has been observed to be up-regulated in HBV infected liver cells. Thus modulators of the kinases of the invention may be used in cases of HBV infection.

The kinases of the invention are also expected to play a role in cardiac cellular processes, either independent of, or in connection with, programmed cell death (apoptosis).

Thus, in one aspect, this invention provides isolated nucleic acid molecules encoding 14790 proteins or biologically active portions thereof, as well as nucleic acid fragments suitable as primers or hybridization probes for the detection of kinase-encoding nucleic acids.

In one embodiment, a kinase encoding a nucleic acid molecule of the invention is at 75%, 77%, 80%, 82%, 85%, 87%, 90%, 92%, 95%, 97%, 98%, 99% or greater homology to nucleotide sequence (e.g., to the entire length of the nucleotide sequence) including SEQ ID NO:1 or a complement thereof. In a preferred embodiment, the isolated nucleic acid molecule includes the nucleotide sequence shown SEQ ID NO:1 or a coding region of SEQ ID NO:1, or a complement thereof. In another embodiment, the nucleic acid molecule includes the 5' UTR and the coding region of SEQ ID NO:1. In yet another embodiment, the nucleic acid molecule includes the coding region of SEQ ID NO:1 and the 3' UTR of SEQ ID NO:1. In another preferred embodiment, the nucleic acid molecule has the nucleotide sequence shown in SEQ ID NO:1 or the coding region of SEQ ID NO:1. In another preferred embodiment, the nucleic acid molecule comprises a fragment of at least 4400 nucleotides of the nucleotide sequence of SEQ ID NO:1 or the coding region of SEQ ID NO:1, or a complement thereof.

In another embodiment, a kinase nucleic acid molecule includes a nucleotide sequence encoding a protein having an amino acid sequence sufficiently homologous to the amino acid sequence of SEQ ID NO:2. In a preferred embodiment, a kinase nucleic acid molecule includes a nucleotide sequence encoding a protein having an amino acid sequence at least 91%, 92%, 93%, 94%, 95%, 96%, 97%, 98%, 99% or more homologous to an amino acid sequence including SEQ ID NO:2 (e.g., the entire amino acid sequence of SEQ ID NO:2).

In another preferred embodiment, an isolated nucleic acid molecule encodes the amino acid sequence of a human kinase, preferably with similarities to known eIF-2 kinases. In yet another preferred embodiment, the nucleic acid molecule includes a nucleotide sequence encoding a protein which includes the amino acid sequence of SEQ ID NO:2. In yet another preferred embodiment, the nucleic acid molecule includes a nucleotide sequence encoding a protein having the amino acid sequence of SEQ ID NO: 2.

Another embodiment of the invention features nucleic acid molecules, preferably kinase nucleic acid molecules, which specifically detect kinase nucleic acid molecules relative to other nucleic acid molecules. In one embodiment, the nucleic acid molecules of the invention may be used to detect and/or differentiate between different eIF-2 kinase encoding nucleic acids. For example, in one embodiment, such a nucleic acid molecule is at least 50, 100, 150, 200, 250, 300, 350, 400, 450, 500, 550, 600, 650, 700, 750, 800, 850, 900, 1000, 1500, 2000, 2500, 3000, 3500, 4000, 4500, 5000, or 5500 nucleotides in length and hybridizes under stringent conditions to a nucleic acid molecule comprising the nucleotide sequence shown in SEQ ID NO:1 or a complement thereof.

In other preferred embodiments, the nucleic acid molecule encodes a naturally occurring allelic variant of a polypeptide which includes the amino acid sequence of SEQ ID NO:2, wherein the nucleic acid molecule hybridizes to a nucleic acid molecule which includes SEQ ID NO:1 or the coding region of SEQ ID NO:1 under stringent conditions.

Another embodiment of the invention provides an isolated nucleic acid molecule which is antisense to the nucleic acid molecule of the invention, e.g., the coding strand of a nucleic acid molecule of the invention.

Another aspect of the invention provides a vector comprising the nucleic acid molecule. In certain embodiments, the vector is a recombinant expression vector. In another embodiment, the invention provides a host cell containing a vector of the invention. The invention also provides a method for producing a kinase, preferably a protein, by culturing in a suitable medium, a host cell, e.g., a mammalian host cell such as a non-human mammalian cell, of the invention containing a recombinant expression vector, such that the protein is produced.

Another aspect of this invention features isolated or recombinant proteins and polypeptides. In one preferred embodiment, the isolated protein, preferably a 14790 protein includes at least one N-glycosylation site; at least one cGMP-dependent protein kinase phosphorylation site; at least one protein kinase C phosphorylation site; at least one casein kinase II phosphorylation site; at least one tyrosine kinase phosphorylation site; at least one N-myristoylation site; at least one amidation site; at least one protein kinase ATP-binding region signature; and at least one Ser/Thr protein kinase active-site signature; and at least one DNA polymerase family B signature.

In another embodiment, the isolated protein, preferably a 14790 protein, includes an amino acid sequence which is of at least 51%, 55%, 60%, 65%, 70%, 75%, 80%, 81%, 85%, 90%, 95%, 99% or greater homology to an amino acid sequence including SEQ ID NO:2. Preferably, the proteins are kinases.

In yet another embodiment, the isolated protein, preferably a 14790 protein, is expressed and/or functions in cells of the hepatic system. Preferably, such proteins act as kinases.

In an even further embodiment, the isolated protein, preferably a 14790 protein, plays a role in signalling pathways associated with cellular growth, e.g., signalling pathways associated with cell cycle regulation and act as kinases.

In another embodiment, the isolated protein, preferably a 14790 protein, includes at least one N-glycosylation site; at least one cGMP-dependent protein kinase phosphorylation site; at least one protein kinase C phosphorylation site; at least one casein kinase II phosphorylation site; at least one tyrosine kinase phosphorylation site; at least one N-myristoylation site; at least one amidation site; at least one protein kinase ATP-binding region signature; and at least one Ser/Thr protein kinase active-site signature; and at least one DNA polymerase family B signature and is able to phosphorylate the core protein of Hepatitis B Virus (HBV).

In another embodiment, the isolated protein, preferably a 14790 protein, is encoded by a nucleic acid molecule having a nucleotide sequence which hybridizes under stringent hybridization conditions to a nucleic acid molecule comprising the nucleotide sequence of SEQ ID NO:1. Preferably, the proteins are kinases.

In another embodiment, the isolated protein, preferably a 14790 protein, has an amino acid sequence homologous to the amino acid sequence of SEQ ID NO:2. In a preferred embodiment, the protein, preferably a 14790 protein, has an amino acid sequence at least about 50%, 55%, 59%, 60%, 65%, 70%, 75%, 80%, 81%, 85%, 90%, 95%, 98% or greater homology to an amino acid sequence including SEQ ID NO:2 (e.g., the entire amino acid sequence of SEQ ID NO:2). In another embodiment, the invention features fragments of the proteins having the amino acid sequence of SEQ ID NO:2, wherein the fragment comprises at least 15, 17, 19 or 21 amino acids (e.g., contiguous amino acids) of the amino acid sequence of SEQ ID NO:2. In another embodiment, the protein, preferably a 14790 protein, has the amino acid sequence of SEQ ID NO:2.

Another embodiment of the invention features an isolated protein, preferably a 14790 protein, which is encoded by a nucleic acid molecule having a nucleotide sequence at least about 50%, 54%, 55%, 60%, 62%, 65%, 70%, 75%, 78%, 80%, 85%, 86%, 90%, 95%, 97%, 98% or greater homology to a nucleotide sequence (e.g., to the entire length of the nucleotide sequence) including SEQ ID NO:1 or the coding region of SEQ ID NO:1 a complement thereof. This invention further features an isolated protein, preferably a 14790 protein, which is encoded by a nucleic acid molecule having a nucleotide sequence which hybridizes under stringent hybridization conditions to a nucleic acid molecule comprising the nucleotide sequence of SEQ ID NO:1 or a complement thereof.

The proteins of the present invention or biologically active portions thereof, can be operatively linked to a non-14790 polypeptide (e.g., heterologous amino acid sequences) to form fusion proteins. The invention further features antibodies, such as monoclonal or polyclonal antibodies, that specifically bind proteins of the invention, preferably 14790 proteins. In addition, the 14790 proteins or biologically active portions thereof can be incorporated into pharmaceutical compositions, which optionally include pharmaceutically acceptable carriers.

In another aspect, the present invention provides a method for detecting the presence of a kinase nucleic acid molecule, protein or polypeptide in a biological sample by contacting the biological sample with one or more agent(s) capable of detecting a kinase nucleic acid molecule, protein or polypeptide such that the presence of a kinase nucleic acid molecule, protein or polypeptide is detected in the biological sample. Examples of agents for the detection of kinases and nucleic acids that encode them are well known in the art.

In another aspect, the present invention provides a method for detecting the presence of kinase activity in a sample by contacting the biological sample with one or more agent(s) capable of detecting 14790 activity. Such agents are known in the art. Examples of agents useful for the detection of eIF-2 kinase activity or the like include peptides or proteins containing eIF-2 phosphorylation target sequences.

In another aspect, the invention provides a method for modulating 14790 activity in a cell by contacting a cell capable of expressing kinase with an agent that modulates kinase activity. In one embodiment, the modulating agent inhibits kinase activity. In another embodiment, the modulating agent stimulates or increases kinase activity. In one embodiment of an inhibitory modulator, the agent is an antibody that specifically binds to a 14790 protein. In another embodiment, the modulating agent regulates expression of kinase by modulating transcription of a kinase gene or translation of a kinase mRNA. In yet another embodiment, the agent is a nucleic acid molecule having a nucleotide sequence that is antisense to the coding strand of a kinase mRNA or a kinase gene.

In one embodiment, the methods of the present invention are used to treat a subject having a disorder characterized by aberrant 14790 protein activity or nucleic acid expression by administering an agent which is a kinase modulator to the subject. In one embodiment, the kinase modulator is a protein. In another embodiment the kinase related modulator is a kinase nucleic acid molecule. In yet another embodiment, the kinase modulator is a peptide, peptidomimetic, or other small molecule. In a preferred embodiment, the disorder characterized by aberrant 14790 protein or nucleic acid expression is a disorder characterized by enhanced viral replication, e.g. during infection with HBV.

The present invention also provides a diagnostic assay for identifying the presence or absence of a genetic alteration characterized by at least one of (i) aberrant modification or mutation of a gene encoding a 14790 protein; (ii) misregulation of the gene; and (iii) aberrant post-translational modification of a 14790 protein, wherein a wild-type form of the gene encodes a protein with a kinase activity.

In another aspect the invention provides a method for identifying a compound that binds to or modulates the activity of a 14790 protein, by providing an indicator composition comprising a 14790 protein having kinase activity, contacting the indicator composition with a test compound, and determining the effect of the test compound on kinase activity in the indicator composition to identify a compound that modulates the activity of a 14790 protein.

Other features and advantages of the invention will be apparent from the following detailed description and claims.

BRIEF DESCRIPTION OF THE DRAWINGS

FIGS. 1a–k depict the cDNA sequence and predicted amino acid sequence of the human 14790 protein kinase. The nucleotide sequence corresponds to the 5525 nucleic acids of SEQ ID NO:1 which include nucleic acids 63–5012 of coding region of SEQ ID NO:1 (nucleic acids 1–4950of SEQ ID NO:3), the 5' UTR of 62 nucleic acids, and the 3' UTR of 513 nucleic acids. The amino acid sequence corresponds to amino acids 1 to 1649 of SEQ ID NO:2.

FIGS. 2 a–i show a multiple sequence alignment of the amino acid sequence of SEQ ID NO:2 in comparison with known mouse (SEQ ID NO:5) and human (SEQ ID NO:4) kinase.

FIGS. 7a–7a3 comprise various regions of SEQ ID NO:2, as well as comparison sequences, (SEQ ID NOS: 8–33), data generated to show PFAM cites, hydrophobicity/hydrophilicity, and cysteine residues of the amino acid sequence of SEQ ID NO:2, as well as PSORT prediction of protein localization, signal peptide predictions, transmembrane segments predicted by MEMSAT, Prosite pattern matches, protein family/domain matches and ProDom matches of the amino acid sequence of SEQ ID NO:2.

DETAILED DESCRIPTION OF THE INVENTION

Figure 3:
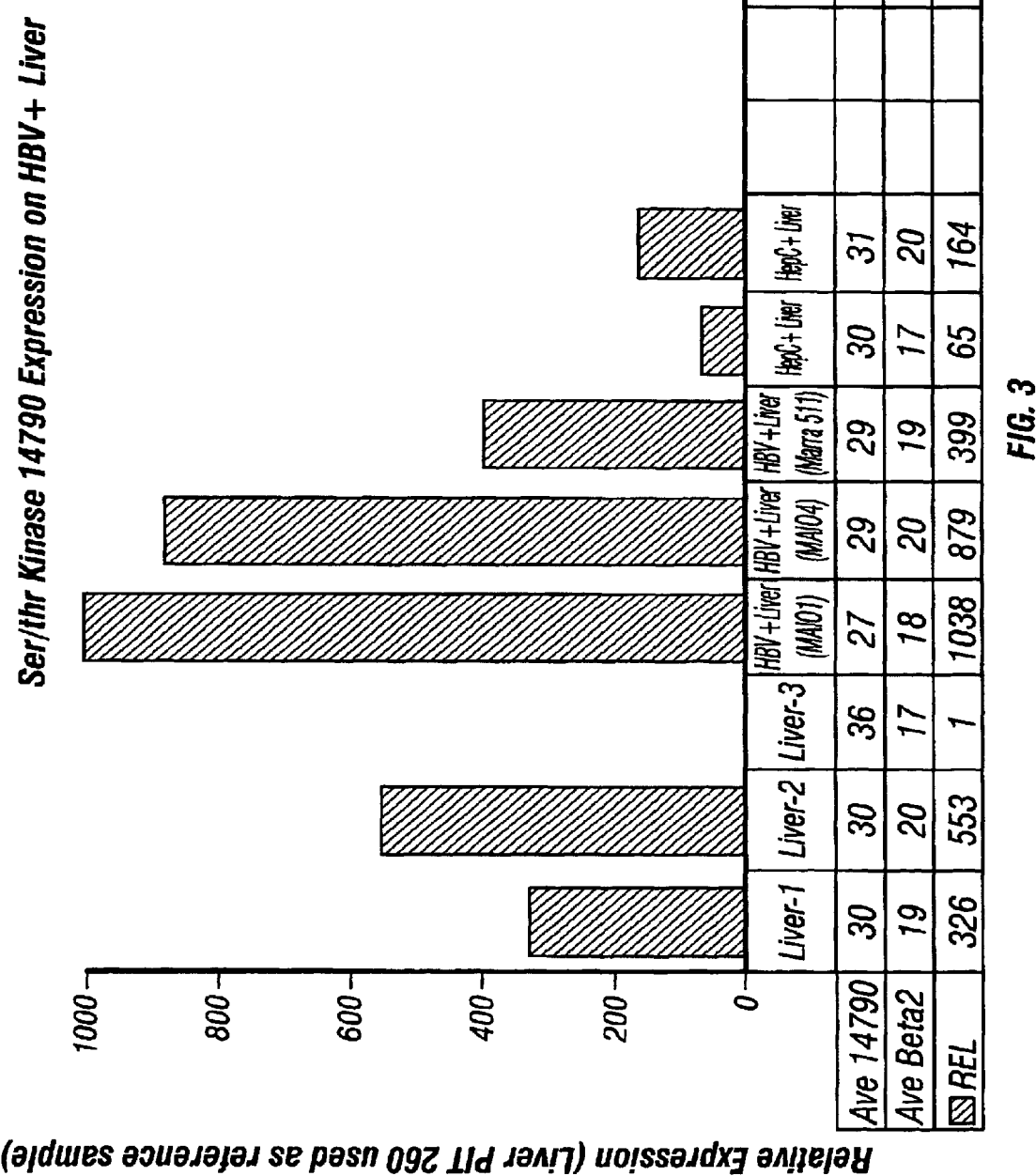
FIG. 3 is a graph of TaqMan RT-PCR data illustrating the relative gene expression on HBV positive liver using liver PTI as a reference sample.
Figure 4:
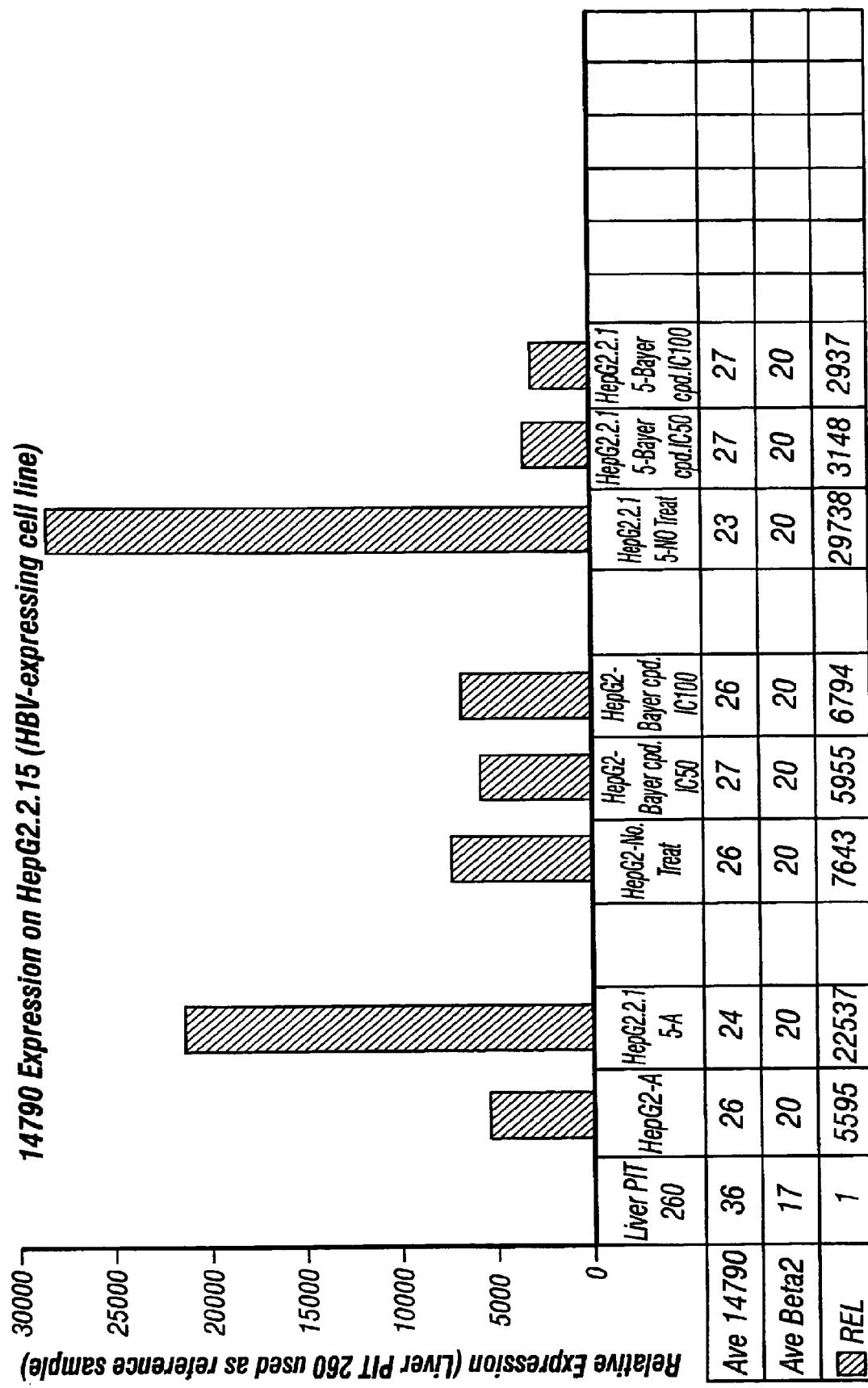
FIG. 4 is a graph of TaqMan RT-PCR data illustrating the relative gene expression on HepG2.2.15 (HBV-expressing line) using liver PTI as a reference sample.
Figure 5:
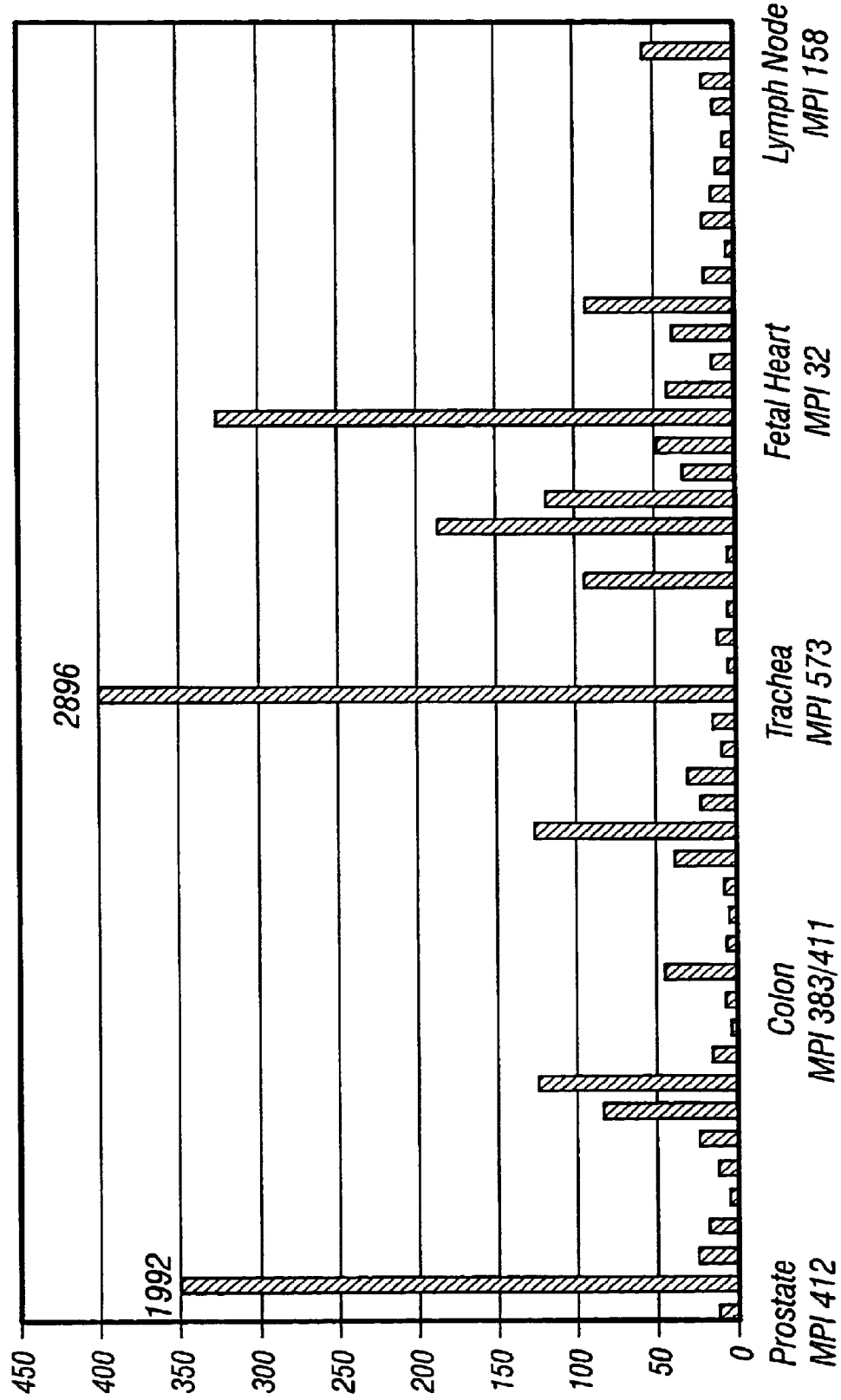
FIG. 5 is a graph of data illustrating the relative gene expression on in normal human tissue using thyroid as a reference.
Figure 6:
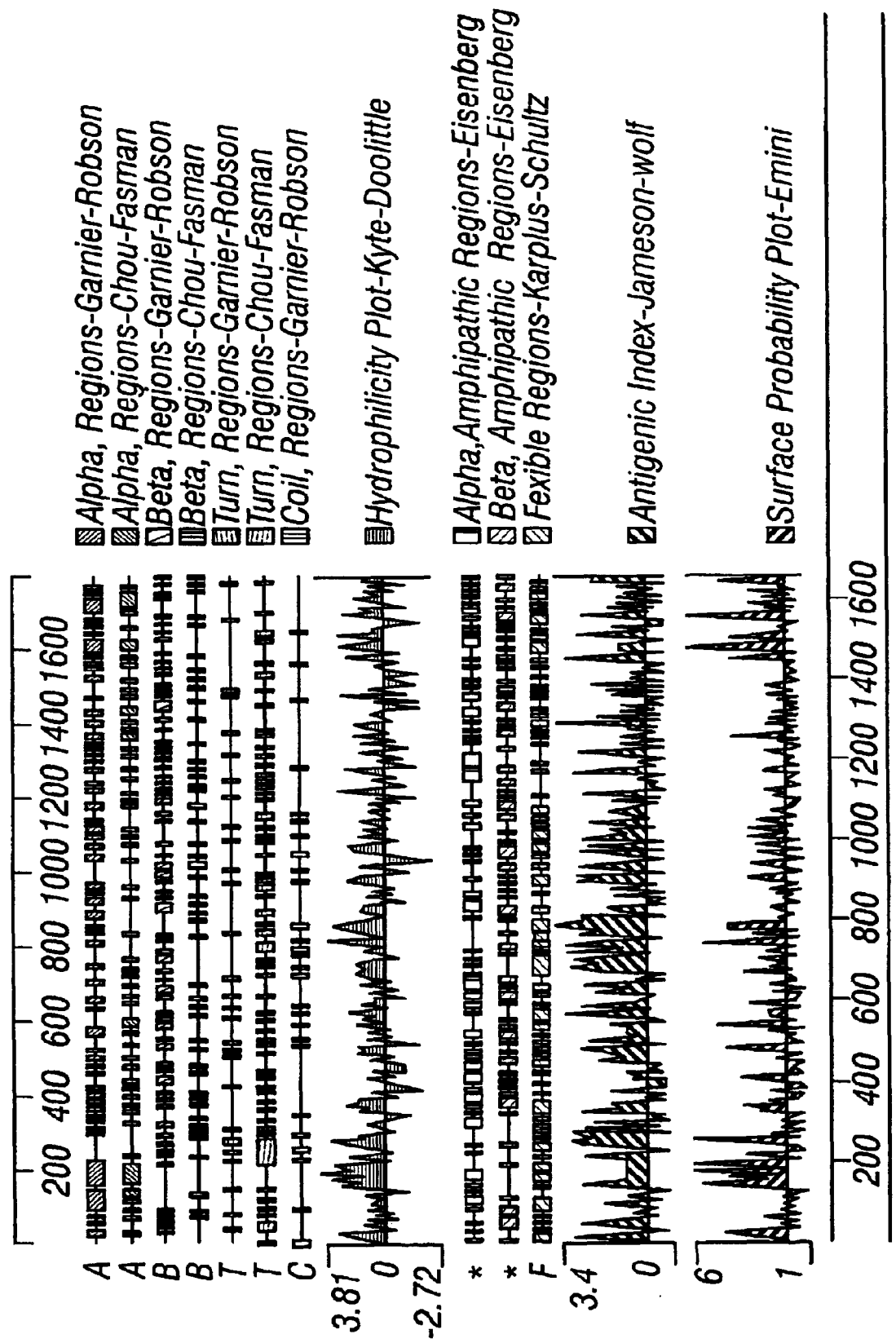
FIG. 6 depicts the structural components of the protein of the amino acid sequence as generated from Protean software.

The present invention is based, at least in part, on the discovery of a novel 14790 molecule, referred to herein as "kinase" or "kinase" nucleic acid and a polypeptide molecule, which play a role in or function in signalling pathways associated with cellular growth. In one embodiment, the molecule modulates the activity of one or more proteins involved in cellular growth or differentiation, e.g., hepatic cell growth or differentiation. In another embodiment, the molecule of the present invention has its mRNA induced in liver cells infected with HBV. In another embodiment, the molecule of the present invention encodes a polypeptide that is able to phosphorylate the core protein of HBV.

In a preferred embodiment, the molecules are protein kinases which are expressed and/or function in cells of the hepatic system, e.g., cells of the liver and the associated blood vessels of the liver.

As used herein, the term "protein kinase" includes a protein or polypeptide which is capable of modulating its own phosphorylation state or the phosphorylation state of another protein or polypeptide. Protein kinases can have a specificity for (i.e., a specificity to phosphorylate) serine/threonine residues, tyrosine residues, or both serine/threonine and tyrosine residues, e.g., the dual specificity kinases. As referred to herein, protein kinases may include a catalytic domain of about 150–400 amino acid residues in length, preferably about 170–300 amino acid residues in length, or more preferably about 190–300 amino acid residues in length, which includes preferably 5–20, more preferably 5–15, or preferably 11 highly conserved motifs or subdomains separated by sequences of amino acids with reduced or minimal conservation. Specificity of a protein kinase for phosphorylation of either tyrosine or serine/threonine can be predicted by the sequence of two of the subdomains (VIb and VIII) in which different residues are conserved in each class (as described in, for example, Hanks et al. (1988) Science 241:42–52) the contents of which are incorporated herein by reference). These subdomains are also described in further detail herein.

Protein kinases play a role in signalling pathways associated with cellular growth. For example, protein kinases are involved in the regulation of signal transmission from cellular receptors, e.g., growth-factor receptors; entry of cells into mitosis; and the regulation of cytoskeleton function, e.g., actin bundling. Thus, the molecules of the present invention may be involved in: 1) the regulation of transmission of signals from cellular receptors, e.g., cardiac cell growth factor receptors; 2) the modulation of the entry of cells, e.g., cardiac precursor cells, into mitosis; 3) the modulation of cellular differentiation; 4) the modulation of cell death; and 5) the regulation of cytoskeleton function, e.g., actin bundling.

Inhibition or over stimulation of the activity of protein kinases involved in signaling pathways associated with cellular growth can lead to perturbed cellular growth, which can in turn lead to cellular growth related disorders. As used herein, a "cellular growth related disorder" includes a disorder, disease, or condition characterized by a deregulation, e.g., an upregulation or a downregulation, of cellular growth. Cellular growth deregulation may be due to a deregulation of cellular proliferation, cell cycle progression, cellular differentiation and/or cellular hypertrophy. Examples of cellular growth related disorders include cardiovascular disorders such as heart failure, hypertension, atrial fibrillation, dilated cardiomyopathy, idiopathic cardiomyopathy, or angina; proliferative disorders or differentiative disorders such as cancer, e.g., melanoma, prostate cancer, cervical cancer, breast cancer, colon cancer, or sarcoma or fibrotic lesions seen in liver fibrosis.

The present invention is based, at least in part, on the discovery of novel molecules, referred to herein as protein and nucleic acid molecules, which comprise a family of molecules having certain conserved structural and functional features. The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics.

One embodiment of the invention features a nucleic acid molecule, preferably a human 14790 molecule, which was identified from a cDNA library. The nucleic acid and protein molecule of the invention is described in further detail in the following subsections.

A. The Kinase Nucleic Acid and Protein Molecules

In one embodiment, the isolated proteins of the present invention, preferably 14790 proteins, are identified based on the presence of at least one "Ser/Thr kinase site" and at least one "ATP-binding region." As used herein, the term "Ser/Thr kinase site" includes an amino acid sequence of about 200–400 amino acid residues in length, preferably 200–300 amino acid residues in length, and more preferably 250–300 amino acid residues in length, which is conserved in kinases which phosphorylate serine and threonine residues and found in the catalytic domain of SerTbr kinases. Preferably, the Ser/Thr kinase site includes the following amino acid consensus sequence $X_9$-g-X-G-$X_4$-V-$X_{12}$-K-X-$_{(10-19)}$-E-$X_{66}$-h-XS-h-r-D-X-K-$X_2$-N-$X_{17}$-K-$X_2$-D-f-g-$X_{21}$-p-$X_{13}$-w-$X_3$-g-$X_{55}$-R-$X_{14}$-h-$X_3$ (SEQ ID NO:6) (where invariant residues are indicated by upper case letters and nearly invariant residues are indicated by lower case letters). The nearly invariant residues are usually found in most Ser/Thr kinase sites, but can be replaced by other amino acids which, preferably, have similar characteristics. For example, a nearly invariant hydrophobic amino acid in the above amino acid consensus sequence would most likely be replaced by another hydrophobic amino acid. Ser/Thr kinase domains are described in, for example, Levin D. E. et al. (1990) Proc. Natl. Acad. Sci. USA 87:8272–76, the contents of which are incorporated herein by reference.

As used herein, the term "ATP-binding region" includes an amino acid sequence of about 5–40, preferably 5–25, and more preferably 5–15 amino acid residues in length, present in enzymes which activate their substrates by phosphorylation, and involved in binding adenosine triphosphate (ATP). ATP-binding regions preferably include the following amino acid consensus sequence: G-X-G-X-X-G-X(15–23)-K (SEQ ID NO:7). ATP-binding regions are described in, for example, Samuel K. P. et al. (1987) FEBS Let. 218(1): 81–86, the contents of which are incorporated herein by reference. Amino acid residues 596–604 of kinase comprise an ATP-binding region.

Isolated proteins of the present invention, preferably 14790 proteins, have an amino acid sequence sufficiently homologous to the amino acid sequence of SEQ ID NO:2 or are encoded by a nucleotide sequence sufficiently homologous to SEQ ID NO:1. As used herein, the term "sufficiently homologous" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%–80%, and even more preferably 90–95% homology across the amino acid sequences of the domains and contain at least one and preferably two structural domains or motifs, are defined herein as sufficiently homologous. Furthermore, amino acid or nucleotide sequences which share at least 30%, 40%, or 50%, preferably 60%, more preferably 70–80%, or 90–95% homology and share a common functional activity are defined herein as sufficiently homologous.

As used interchangeably herein a "kinase activity", "biological activity of kinase" or "functional activity of kinase", refers to an activity exerted by a 14790 protein, polypeptide or nucleic acid molecule on a kinase responsive cell or a 14790 protein substrate, as determined in vivo, or in vitro, according to standard techniques. The biological activity of kinase is described herein.

Accordingly, another embodiment of the invention features isolated 14790 proteins and polypeptides having a kinase activity. Preferred proteins are 14790 proteins having at least one N-glycosylation site; at least one cGMP-dependent protein kinase phosphorylation site; at least one protein kinase C phosphorylation site; at least one casein kinase II phosphorylation site; at least one tyrosine kinase phosphorylation site; at least one N-myristoylation site; at least one amidation site; at least one protein kinase ATP-binding region signature; and at least one Ser/Thr protein kinase active-site signature; and at least one DNA polymerase family B signature and, preferably, a kinase activity. Additional preferred proteins have at least one N-glycosylation site; at least one cGMP-dependent protein kinase phosphorylation site; at least one protein kinase C phosphorylation site; at least one casein kinase II phosphorylation site; at least one tyrosine kinase phosphorylation site; at least one N-myristoylation site; at least one amidation site; at least one protein kinase ATP-binding region signature; and at least one Ser/Thr protein kinase active-site signature; and at least one DNA polymerase family B signature and are, preferably, encoded by a nucleic acid molecule having a nucleotide sequence which hybridizes under stringent hybridization conditions to a nucleic acid molecule comprising the nucleotide sequence of SEQ ID NO:1 or the coding region thereof.

The nucleotide sequence of the isolated human kinase cDNA and the predicted amino acid sequence of the human 14790 polypeptide are shown in FIG. 1 and in SEQ ID NOs:1 and 2, respectively.

The kinase gene, which is approximately 5525 nucleotides in length, encodes a protein having a molecular weight of approximately 181.5 kD and which is approximately 1650 amino acid residues in length. The kinase gene is expressed predominantly in skeletal muscle, brain and liver.

Various aspects of the invention are described in further detail in the following subsections:

I. Isolated Nucleic Acid Molecules

One aspect of the invention pertains to isolated nucleic acid molecules that encode 14790 proteins or biologically active portions thereof, as well as nucleic acid fragments sufficient for use as hybridization probes to identify kinase-encoding nucleic acids (e.g., kinase mRNA) and fragments for use as PCR primers for the amplification or mutation of kinase nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated kinase nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1 or coding region thereof, or a portion thereof, can be isolated using standard molecular biology techniques and the sequence information provided herein. For example, using all or portion of the nucleic acid sequence of SEQ ID NO: 1, or the coding region thereof, as a hybridization probe, kinase nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:1, or the coding region thereof, can be isolated by the polymerase chain reaction (PCR) using synthetic oligonucleotide primers designed based upon the sequence of SEQ ID NO:1, or the coding region thereof.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1. The sequence of SEQ ID NO:1 corresponds to the partial human kinase cDNA. This cDNA comprises sequences encoding the human 14790 protein (i.e., "the coding region", from nucleotides 63–5012), as well as 5' untranslated sequences (62 nucleotides) and 3' untranslated sequences (513 nucleotides). Alternatively, the nucleic acid molecule can comprise only the coding region of SEQ ID NO:1 (e.g., nucleotides 63–5012).

In another preferred embodiment, an isolated nucleic acid molecule of the invention comprises a nucleic acid molecule which is a complement of the nucleotide sequence shown in SEQ ID NO:1, or the coding region thereof, or a portion of any of these nucleotide sequences. A nucleic acid molecule which is complementary to the nucleotide sequence shown in SEQ ID NO:1, or the coding region thereof, is one which is sufficiently complementary to the nucleotide sequence shown in SEQ ID NO:1, or the coding region thereof, such that it can hybridize to the nucleotide sequence shown in SEQ ID NO:1, or the coding region thereof, thereby forming a stable duplex.

In still another preferred embodiment, an isolated nucleic acid molecule of the present invention comprises a nucleotide sequence which is at least about 50%, 54%, 55%, 60%, 62%, 65%, 70%, 75%, 78%, 80%, 85%, 86%, 90%, 95%, 97%, 98% or more homologous to the nucleotide sequence (e.g., to the entire length of the nucleotide sequence) shown in SEQ ID NO:1, or the coding region thereof, or a portion of any of these nucleotide sequences.

Moreover, the nucleic acid molecule of the invention can comprise only a portion of the nucleic acid sequence of SEQ ID NO:1, or the coding region thereof, for example a fragment which can be used as a probe or primer or a fragment encoding a biologically active portion of a 14790 protein. The nucleotide sequence determined from the cloning of the kinase gene allows for the generation of probes and primers designed for use in identifying and/or cloning other kinase family members, as well as kinase homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1, of an anti-sense sequence of SEQ ID NO:1, or the coding region thereof, or of a naturally occurring allelic variant or mutant of SEQ ID NO:1, or the coding region thereof. In an exemplary embodiment, a nucleic acid molecule of the present invention comprises a nucleotide sequence which is at least 350, 400, 450, 500, 550, 600, 650, 700, 750, 800, 850, 900, 950, 1000, 1500, 2000, 2500, 3000, 3500, 4000, or 4500 nucleotides in length and hybridizes under stringent hybridization conditions to a nucleic acid molecule of SEQ ID NO:1, or the coding region thereof.

Probes based on the nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissues which misexpress a 14790 protein, such as by measuring a level of a kinase-encoding nucleic acid in a sample of cells from a subject e.g., detecting kinase mRNA levels or determining whether a genomic kinase gene has been mutated or deleted.

A nucleic acid fragment encoding a "biologically active portion of a 14790 protein" can be prepared by isolating a portion of the nucleotide sequence of SEQ ID NO:1, or the coding region thereof, which encodes a polypeptide having a kinase biological activity (the biological activities of the 14790 proteins are described herein), expressing the encoded portion of the 14790 protein (e.g., by recombinant expression in vitro) and assessing the activity of the encoded portion of the 14790 protein.

The invention further encompasses nucleic acid molecules that differ from the nucleotide sequence shown in SEQ ID NO:1, or the coding region thereof, due to the degeneracy of the genetic code and, thus, encode the same 14790 proteins as those encoded by the nucleotide sequence shown in SEQ ID NO:1, or the coding region thereof. In another embodiment, an isolated nucleic acid molecule of the invention has a nucleotide sequence encoding a protein having an amino acid sequence shown in SEQ ID NO:2.

In addition to the kinase nucleotide sequences shown in SEQ ID NO:1, or the coding region thereof, it will be appreciated by those skilled in the art that DNA sequence polymorphisms that lead to changes in the amino acid sequences of the 14790 proteins may exist within a population (e.g., the human population). Such genetic polymorphism in the kinase genes may exist among individuals within a population due to natural allelic variation. As used herein, the terms "gene" and "recombinant gene" refer to nucleic acid molecules which include an open reading frame encoding a 14790 protein, preferably a mammalian 14790 protein, and can further include non-coding regulatory sequences, and introns. Such natural allelic variations include both functional and non-functional 14790 proteins and can typically result in 1–5% variance in the nucleotide sequence of a kinase gene. Any and all such nucleotide variations and resulting amino acid polymorphisms in genes that are the result of natural allelic variation and that do not alter the functional activity of a protein are intended to be within the scope of the invention.

Moreover, nucleic acid molecules encoding other kinase family members and, thus, which have a nucleotide sequence which differs from the kinase sequences of SEQ ID NO:1, or the coding region thereof, are intended to be within the scope of the invention. For example, another kinase cDNA can be identified based on the nucleotide sequence of human kinase. Moreover, nucleic acid molecules encoding 14790 proteins from different species, and thus which have a nucleotide sequence which differs from the kinase sequences of SEQ ID NO:1, or the coding region thereof, are intended to be within the scope of the invention. For example, a mouse kinase cDNA can be identified based on the nucleotide sequence of a human kinase.

Nucleic acid molecules corresponding to natural allelic variants and homologues of the kinase cDNAs of the invention can be isolated based on their homology to the kinase nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1, or the coding region thereof. In other embodiment, the nucleic acid is at least 30, 50, 100, 150, 200, 250, 300, 350, 400, 450, 500, 550, 600, 650, 700, 750, 800, 850, 900, 950, 1000, 1500, 2000, 2500, 3000, 3500, 4000, or 4500 nucleotides in length. As used herein, the term "hybridizes under stringent conditions" is intended to describe conditions for hybridization and washing under which nucleotide sequences at least 30%, 40%, 50%, or 60% homologous to each other typically remain hybridized to each other. Preferably, the conditions are such that sequences at least about 70%, more preferably at least about 80%, even more preferably at least about 85% or 90% homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50–65° C. A more preferred example of stringent hybridization conditions is hybridization in 0.5M sodium phosphate, 7% SDS at 65° C., followed by one or more washes in 0.2×SSC at 65° C. Preferably, an isolated nucleic acid molecule of the invention that hybridizes under stringent conditions to the sequence of SEQ ID NO:1, or the coding region thereof, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the kinase sequences that may exist in the population, the skilled artisan will further appreciate that changes can be introduced by mutation into the nucleotide sequences of SEQ ID NO:1, or the coding region thereof, thereby leading to changes in the amino acid sequence of the encoded 14790 proteins, without altering the functional ability of the 14790 proteins. For example, nucleotide substitutions leading to amino acid substitutions at "non-essential" amino acid residues can be made in the sequence of SEQ ID NO:1, or the coding region thereof. A "non-essential" amino acid residue is a residue that can be altered from the wild-type sequence of kinase (e.g., the sequence of SEQ ID NO:2) without altering the biological activity, whereas an "essential" amino acid residue is required for biological activity. For example, amino acid residues that are conserved among the 14790 proteins of the present invention, are predicted to be particularly unamenable to alteration. Furthermore, additional amino acid residues that are conserved between the 14790 proteins of the present invention and other kinase family members are not likely to be amenable to alteration.

Accordingly, another aspect of the invention pertains to nucleic acid molecules encoding 14790 proteins that contain changes in amino acid residues that are not essential for activity. Such 14790 proteins differ in amino acid sequence from SEQ ID NO:2, yet retain biological activity. In one embodiment, the isolated nucleic acid molecule comprises a nucleotide sequence encoding a protein, wherein the protein comprises an amino acid sequence at least about 41%, 42%, 45%, 50%, 55%, 59%, 60%, 65%, 70%, 75%, 80%, 81%, 85%, 90%, 95%, 98% or more homologous to the amino acid sequence of SEQ ID NO:2 (e.g., the entire amino acid sequence of SEQ ID NO:2).

An isolated nucleic acid molecule encoding a 14790 protein homologous to the protein of SEQ ID NO:2 can be created by introducing one or more nucleotide substitutions, additions or deletions into the nucleotide sequence of SEQ ID NO:1 such that one or more amino acid substitutions, additions or deletions are introduced into the encoded protein. Mutations can be introduced into SEQ ID NO:1, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 14790 protein is preferably replaced with another amino acid residue from the same side chain family. Alternatively, in another embodiment, mutations can be introduced randomly along all or part of a kinase coding sequence, such as by saturation mutagenesis, and the resultant mutants can be screened for kinase biological activity to identify mutants that retain activity. Following mutagenesis of SEQ ID NO:1, the encoded protein can be expressed recombinantly and the activity of the protein can be determined.

In a preferred embodiment, a mutant 14790 protein can be assayed for the ability to: 1) regulate transmission of signals from cellular receptors, e.g., cardiac cell growth factor receptors; 2) control entry of cells, e.g., cardiac cells, into mitosis; 3) modulate cellular differentiation; 4) modulate cell death; 5) regulate cytoskeleton function, e.g., actin bundling; or being able to phosphorylate the core protein of HBV.

In addition to the nucleic acid molecules encoding 14790 proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire kinase coding strand, or only to a portion thereof. In one embodiment, an antisense nucleic acid molecule is antisense to a "coding region" of the coding strand of a nucleotide sequence encoding kinase. The term "coding region" refers to the region of the nucleotide sequence comprising codons which are translated into amino acid residues (e.g., the coding region of human kinase corresponds to 63–5012 of SEQ ID NO:1. In another embodiment, the antisense nucleic acid molecule is antisense to a "noncoding region" of the coding strand of a nucleotide sequence encoding kinase. The term "noncoding region" refers to 5' and 3' sequences which flank the coding region that are not translated into amino acids (i.e., also referred to as 5' and 3' untranslated regions).

Given the coding strand sequences encoding kinase disclosed herein (e.g., nucleic acids 63–5012 of SEQ ID NO:1) antisense nucleic acids of the invention can be designed according to the rules of Watson and Crick base pairing. The antisense nucleic acid molecule can be complementary to the entire coding region of kinase mRNA, but more preferably is an oligonucleotide which is antisense to only a portion of the coding or noncoding region of kinase mRNA. For example, the antisense oligonucleotide can be complementary to the region surrounding the translation start site of kinase mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a 14790 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleaving a single-stranded nucleic acid, such as a kinase mRNA, to which they have a complementary region. Thus, ribozymes (e.g., hammerhead ribozymes (described in Haselhoff and Gerlach (1988) *Nature* 334:585–591)) can be used to catalytically cleave kinase mRNA transcripts to thereby inhibit translation of kinase mRNA. A ribozyme having specificity for a kinase-encoding nucleic acid can be designed based upon the nucleotide sequence of a kinase cDNA disclosed herein (i.e., SEQ ID NO:1, or the coding region thereof). For example, a derivative of a *Tetrahymena* L-19 IVS RNA can be constructed in which the nucleotide sequence of the active site is complementary to the nucleotide sequence to be cleaved in a kinase-encoding mRNA. See, e.g., Cech et al. U.S. Pat. No. 4,987,071; and Cech et al. U.S. Pat. No. 5,116,742. Alternatively, kinase mRNA can be used to select a catalytic RNA having a specific ribonuclease activity from a pool of RNA molecules. See, e.g., Bartel, D. and Szostak, J. W. (1993) *Science* 261:1411–1418.

Alternatively, kinase gene expression can be inhibited by targeting nucleotide sequences complementary to the regulatory region of the kinase (e.g., the kinase promoter and/or enhancers) to form triple helical structures that prevent transcription of the kinase gene in target cells. See generally, Helene, C. (1991) *Anticancer Drug Des.* 6(6):569–84; Helene, C. et al. (1992) *Ann. N.Y. Acad. Sci.* 660:27–36; and Maher, L. J. (1992) *Bioassays* 14(12):807–15.

In yet another embodiment, the kinase nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670–675.

PNAs of kinase nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of kinase nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of kinase can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of kinase nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. US.* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

II. Isolated 14790 Proteins and Anti-Kinase Antibodies

One aspect of the invention pertains to isolated 14790 proteins, and biologically active portions thereof, as well as polypeptide fragments suitable for use as immunogens to raise anti-kinase antibodies. In one embodiment, native 14790 proteins can be isolated from cells or tissue sources by an appropriate purification scheme using standard protein purification techniques. In another embodiment, 14790 proteins are produced by recombinant DNA techniques. Alternative to recombinant expression, a 14790 protein or polypeptide can be synthesized chemically using standard peptide synthesis techniques.

An "isolated" or "purified" protein or biologically active portion thereof is substantially free of cellular material or other contaminating proteins from the cell or tissue source from which the 14790 protein is derived, or substantially free from chemical precursors or other chemicals when chemically synthesized. The language "substantially free of cellular material" includes preparations of 14790 protein in which the protein is separated from cellular components of the cells from which it is isolated or recombinantly produced. In one embodiment, the language "substantially free of cellular material" includes preparations of 14790 protein having less than about 30% (by dry weight) of non-14790 protein (also referred to herein as a "contaminating protein"), more preferably less than about 20% of non-14790 protein, still more preferably less than about 10% of non-14790 protein, and most preferably less than about 5% non-14790 protein. When the 14790 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of 14790 protein in which the protein is separated from chemical precursors or other chemicals which are involved in the synthesis of the protein. In one embodiment, the language "substantially free of chemical precursors or other chemicals" includes preparations of 14790 protein having less than about 30% (by dry weight) of chemical precursors or non-kinase chemicals, more preferably less than about 20% chemical precursors or non-kinase chemicals, still more preferably less than about 10% chemical precursors or non-kinase chemicals, and most preferably less than about 5% chemical precursors or non-kinase chemicals.

Biologically active portions of a 14790 protein include peptides comprising amino acid sequences sufficiently homologous to or derived from the amino acid sequence of the 14790 protein, e.g., the amino acid sequence shown in SEQ ID NO:2, which include less amino acids than the full length 14790 proteins, and exhibit at least one activity of a 14790 protein. Typically, biologically active portions comprise a domain or motif with at least one activity of the 14790 protein. A biologically active portion of a 14790 protein can be a polypeptide which is, for example, at least 10, 25, 50, 100 or more amino acids in length.

In a preferred embodiment, the 14790 protein has an amino acid sequence shown in SEQ ID NO:2. In other embodiments, the 14790 protein is substantially homologous to SEQ ID NO:2, and retains the functional activity of the protein of SEQ ID NO:2, yet differs in amino acid sequence due to natural allelic variation or mutagenesis, as described in detail in subsection I above. Accordingly, in another embodiment, the 14790 protein is a protein which comprises an amino acid sequence at least about 55%, 59%, 60%, 65%, 70%, 75%, 80%, 81%, 85%, 90%, 95%, 98% or more homologous to the amino acid sequence of SEQ ID NO:2 (e.g., the entire amino acid sequence of SEQ ID NO:2).

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the kinase amino acid sequence of SEQ ID NO:2 having 1649 amino acid residues, at least 49, preferably at least 660, more preferably at least 825, even more preferably at least 990, and even more preferably at least 1155, 1320 or 1486 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A more preferred embodiment, the percent identity between two nucleotide or amino acid sequences is determined using a Blosum 62 scoring matrix with a gap open penalty of 12, a gap extend penalty of 4, and a frameshift gap penalty of 5.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used.

The invention also provides kinase chimeric or fusion proteins. As used herein, a kinase "chimeric protein" or "fusion protein" comprises a 14790 polypeptide operatively linked to a non-14790 polypeptide. A kinase "polypeptide" refers to a polypeptide having an amino acid sequence corresponding to kinase, whereas a "non-14790 polypeptide" refers to a polypeptide having an amino acid sequence corresponding to a protein which is not substantially homologous to the 14790 protein, e.g., a protein which is different from the 14790 protein and which is derived from the same or a different organism. Within a kinase fusion protein the 14790 polypeptide can correspond to all or a portion of a protein. In a preferred embodiment, a kinase fusion protein comprises at least one biologically active portion of a 14790 protein. In another preferred embodiment, a kinase fusion protein comprises at least two biologically active portions of a 14790 protein. Within the fusion protein, the term "operatively linked" is intended to indicate that the 14790 polypeptide and the non-14790 polypeptide are fused in-frame to each other. The non-14790 polypeptide can be fused to the N-terminus or C-terminus of the 14790 polypeptide.

For example, in one embodiment, the fusion protein is a GST-kinase fusion protein in which the kinase sequences are fused to the C-terminus of the GST sequences. Such fusion proteins can facilitate the purification of recombinant kinase.

In another embodiment, the fusion protein is a 14790 protein containing a heterologous signal sequence at its N-terminus. In certain host cells (e.g., mammalian host cells), expression and/or secretion of kinase can be increased through use of a heterologous signal sequence.

The kinase fusion proteins of the invention can be incorporated into pharmaceutical compositions and administered to a subject in vivo. The kinase fusion proteins can be used to affect the bioavailability of a kinase substrate. Use of kinase fusion proteins may be useful therapeutically for the treatment of viral infections, e.g., infection of liver cells with HBV. Moreover, the kinase-fusion proteins of the invention can be used as immunogens to produce anti-kinase antibodies in a subject, to purify kinase ligands and in screening assays to identify 14790 molecules which inhibit the interaction of with a kinase substrate.

Preferably, a kinase chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g., a GST polypeptide). A kinase-encoding nucleic acid can be cloned into such an expression vector such that the fusion moiety is linked in-frame to the 14790 protein.

The present invention also pertains to variants of the 14790 proteins which function as either kinase agonists (mimetics) or as kinase antagonists. Variants of the 14790 proteins can be generated by mutagenesis, e.g., discrete point mutation or truncation of a 14790 protein. An agonist of the 14790 proteins can retain substantially the same, or a subset, of the biological activities of the naturally occurring form of a 14790 protein. An antagonist of a 14790 protein can inhibit one or more of the activities of the naturally occurring form of the 14790 kinase protein. An antagonist of the 14790 protein can inhibit one or more of the activities of the naturally occurring from of the kinase protein by, for example, by competitively modulating the ability of 14790 protein to phosphorylate the core protein of HBV. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the 14790 protein.

In one embodiment, variants of a 14790 protein which function as either kinase agonists (mimetics) or as kinase antagonists can be identified by screening combinatorial libraries of mutants, e.g., truncation mutants, of a 14790 protein for 14790 protein agonist or antagonist activity. In one embodiment, a variegated library of kinase variants is generated by combinatorial mutagenesis at the nucleic acid level and is encoded by a variegated gene library. A variegated library of kinase variants can be produced by, for example, enzymatically ligating a mixture of synthetic oligonucleotides into gene sequences such that a degenerate set of potential kinase sequences is expressible as individual polypeptides, or alternatively, as a set of larger fusion proteins (e.g., for phage display) containing the set of kinase sequences therein. There are a variety of methods which can be used to produce libraries of potential kinase variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential kinase sequences. Methods for synthesizing degenerate oligonucleotides are known in the art (see, e.g., Narang, S. A. (1983) Tetrahedron 39:3; Itakura et al. (1984) Annu. Rev. Biochem. 53:323; Itakura et al. (1984) Science 198:1056; Ike et al. (1983) Nucleic Acid Res. 11:477.

In addition, libraries of fragments of a 14790 protein coding sequence can be used to generate a variegated population of kinase fragments for screening and subsequent selection of variants of a 14790 protein. In one embodiment, a library of coding sequence fragments can be generated by treating a double stranded PCR fragment of a kinase coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the 14790 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of 14790 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify kinase variants (Arkin and Yourvan (1992) Proc. Natl. Acad. Sci. USA 89:7811–7815; Delgrave et al. (1993) Protein Engineering 6(3):327–331).

In one embodiment, cell based assays can be exploited to analyze a variegated kinase library. For example, a library of expression vectors can be transfected into a cell line which ordinarily synthesizes and secretes kinase. The transfected cells are then cultured such that kinase and a particular mutant are secreted and the effect of expression of the mutant on activity in cell supernatants can be detected, e.g., by any of a number of enzymatic assays. Plasmid DNA can then be recovered from the cells which score for inhibition, or alternatively, potentiation of kinase activity, and the individual clones further characterized.

An isolated 14790 protein, or a portion or fragment thereof, can be used as an immunogen to generate antibodies that bind kinase using standard techniques for polyclonal and monoclonal antibody preparation. A full-length 14790 protein can be used or, alternatively, the invention provides antigenic peptide fragments of kinase for use as immunogens. The antigenic peptide of kinase comprises at least 8 amino acid residues of the amino acid sequence shown in SEQ ID NO:2 and encompasses an epitope of kinase such that an antibody raised against the peptide forms a specific immune complex with kinase. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of kinase that are located on the surface of the protein, e.g., hydrophilic regions.

A kinase immunogen typically is used to prepare antibodies by immunizing a suitable subject, (e.g., rabbit, goat, mouse or other mammal) with the immunogen. An appropriate immunogenic preparation can contain, for example, recombinantly expressed 14790 protein or a chemically synthesized 14790 polypeptide. The preparation can further include an adjuvant, such as Freund's complete or incomplete adjuvant, or similar immunostimulatory agent. Immunization of a suitable subject with an immunogenic kinase preparation induces a polyclonal anti-kinase antibody response.

Accordingly, another aspect of the invention pertains to anti-kinase antibodies. The term "antibody" as used herein refers to immunoglobulin molecules and immunologically active portions of immunoglobulin molecules, i.e., molecules that contain an antigen binding site which specifically binds (immunoreacts with) an antigen, such as kinase. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind kinase. The term "monoclonal antibody" or "monoclonal antibody composition", as used herein, refers to a population of antibody molecules that contain only one species of an antigen binding site capable of immunoreacting with a particular epitope of kinase. A monoclonal antibody composition thus typically displays a single binding affinity for a particular 14790 protein with which it immunoreacts.

Polyclonal anti-kinase antibodies can be prepared as described above by immunizing a suitable subject with a kinase immunogen. The anti-kinase antibody titer in the immunized subject can be monitored over time by standard techniques, such as with an enzyme linked immunosorbent assay (ELISA) using immobilized kinase. If desired, the antibody molecules directed against kinase can be isolated from the mammal (e.g., from the blood) and further purified by well known techniques, such as protein A chromatography to obtain the IgG fraction. At an appropriate time after immunization, e.g., when the anti-kinase antibody titers are highest, antibody-producing cells can be obtained from the subject and used to prepare monoclonal antibodies by standard techniques, such as the hybridoma technique originally described by Kohler and Milstein (1975)*Nature* 256:495–497) (see also, Brown et al. (1981) *J. Immunol.* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J.*

Biol. Med., 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with a kinase immunogen as described above, and the culture supernatants of the resulting hybridoma cells are screened to identify a hybridoma producing a monoclonal antibody that binds kinase.

Any of the many well known protocols used for fusing lymphocytes and immortalized cell lines can be applied for the purpose of generating an anti-kinase monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O -Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind kinase, e.g., using a standard ELISA assay.

Alternative to preparing monoclonal antibody-secreting hybridomas, a monoclonal anti-kinase antibody can be identified and isolated by screening a recombinant combinatorial immunoglobulin library (e.g., an antibody phage display library) with kinase to thereby isolate immunoglobulin library members that bind kinase. Kits for generating and screening phage display libraries are commercially available (e.g., the *Pharmacia Recombinant Phage Antibody System*, Catalog No. 27-9400-01; and the *Stratagene SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, recombinant anti-kinase antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-kinase antibody (e.g., monoclonal antibody) can be used to isolate kinase by standard techniques, such as affinity chromatography or immunoprecipitation. An anti-kinase antibody can facilitate the purification of natural kinase from cells and of recombinantly produced kinase expressed in host cells. Moreover, an anti-kinase antibody can be used to detect 14790 protein (e.g., in a cellular lysate or cell supernatant) in order to evaluate the abundance and pattern of expression of the 14790 protein. Anti-kinase antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to vectors, preferably expression vectors, containing a nucleic acid encoding a 14790 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., 14790 proteins, mutant forms of 14790 proteins, fusion proteins, and the like).

The recombinant expression vectors of the invention can be designed for expression of 14790 proteins in prokaryotic or eukaryotic cells. For example, 14790 proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in kinase activity assays, (e.g., direct assays or competitive assays described in detail below), or to generate antibodies specific for 14790 proteins, for example. In a preferred embodiment, a kinase fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res*. 20:2111–2118). Such alteration of nucleic acid sequences of the invention can be carried out by standard DNA synthesis techniques.

In another embodiment, the kinase expression vector is a yeast expression vector. Examples of vectors for expression in yeast *S. cerivisae* include pYepSec1 (Baldari, et al., (1987) *Embo J*. 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, 14790 proteins can be expressed in insect cells using baculovirus expression vectors. Baculovirus vectors available for expression of proteins in cultured insect cells (e.g., Sf9 cells) include the pAc series (Smith et al. (1983) *Mol. Cell Biol*. 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to kinase mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 14790 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a 14790 protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a 14790 protein. Accordingly, the invention further provides methods for producing a 14790 protein using the host cells of the invention. In one embodiment, the method comprises culturing the host cell of invention (into which a recombinant expression vector encoding a 14790 protein has been introduced) in a suitable medium such that a 14790 protein is produced. In another embodiment, the method further comprises isolating a 14790 protein from the medium or the host cell.

The host cells of the invention can also be used to produce non-human transgenic animals. For example, in one embodiment, a host cell of the invention is a fertilized oocyte or an embryonic stem cell into which kinase-coding sequences have been introduced. Such host cells can then be used to create non-human transgenic animals in which exogenous kinase sequences have been introduced into their genome or homologous recombinant animals in which endogenous kinase sequences have been altered. Such animals are useful for studying the function and/or activity of a kinase and for identifying and/or evaluating modulators of kinase activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a kinase encoding nucleic acid into the male pronuclei of a fertilized oocyte, e.g., by microinjection, retroviral infection, and allowing the oocyte to develop in a pseudopregnant female foster animal. The kinase cDNA sequence corresponding to SEQ ID NO:1 can be introduced as a transgene into the genome of a non-human animal. Alternatively, a nonhuman homologue of a human kinase gene, such as a mouse or rat kinase gene, can be used as a transgene. Alternatively, a kinase gene homologue, such as another kinase family member, can be isolated based on hybridization to the kinase cDNA sequences of SEQ ID NO:1, or the coding region thereof, (described further in subsection I above) and used as a transgene. Intronic sequences and polyadenylation signals can also be included in the transgene to increase the efficiency of expression of the transgene. A tissue-specific regulatory sequence(s) can be operably linked to a kinase transgene to direct expression of a 14790 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a kinase transgene in its genome and/or expression of kinase mRNA in tissues or cells of the animals. A transgenic founder animal can then be used to breed additional animals carrying the transgene. Moreover, transgenic animals carrying a transgene encoding a 14790 protein can further be bred to other transgenic animals carrying other transgenes.

To create a homologous recombinant animal, a vector is prepared which contains at least a portion of a kinase gene into which a deletion, addition or substitution has been introduced to thereby alter, e.g., functionally disrupt, the kinase gene. The kinase gene can be a human gene (e.g., the SEQ ID NO:1), but more preferably, is a non-human homologue of a human kinase gene (e.g., a cDNA isolated by stringent hybridization with the nucleotide sequence of SEQ ID NO:1). For example, a mouse kinase gene can be used to construct a homologous recombination vector suitable for altering an endogenous kinase gene in the mouse genome. In a preferred embodiment, the vector is designed such that, upon homologous recombination, the endogenous kinase gene is functionally disrupted (i.e., no longer encodes a functional protein; also referred to as a "knock out" vector). Alternatively, the vector can be designed such that, upon homologous recombination, the endogenous kinase gene is mutated or otherwise altered but still encodes a functional protein (e.g., the upstream regulatory region can be altered to thereby alter the expression of the endogenous 14790 protein). In the homologous recombination vector, the altered portion of the kinase gene is flanked at its 5' and 3' ends by additional nucleic acid sequence of the gene to allow for homologous recombination to occur between the exogenous kinase gene carried by the vector and an endogenous kinase gene in an embryonic stem cell. The additional flanking kinase nucleic acid sequence is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced kinase gene has homologously recombined with the endogenous kinase gene are selected (see, e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconctructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The kinase nucleic acid molecules, 14790 proteins, and anti-kinase antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a 14790 protein or anti-kinase antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratiot LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). The isolated nucleic acid molecules of the invention can be used, for example, to express 14790 protein (e.g., via a recombinant expression vector in a host cell in gene therapy applications), to detect kinase mRNA (e.g., in a biological sample) or a genetic alteration in a kinase gene, and to modulate kinase activity, as described further below. The 14790 proteins can be used to treat disorders characterized by insufficient or excessive production of a kinase substrate or production of kinase inhibitors. In addition, the 14790 proteins can be used to screen for naturally occurring kinase substrates, to screen for drugs or compounds which modulate kinase activity, as well as to treat disorders characterized by insufficient or excessive production of 14790 protein or production of 14790 protein forms which have decreased or aberrant activity compared to kinase wild type protein. Moreover, the anti-kinase antibodies of the invention can be used to detect and isolate 14790 proteins, regulate the bioavailability of 14790 proteins, and modulate kinase activity.

A. Screening Assays:

The invention provides a method (also referred to herein as a "screening assay") for identifying modulators, i.e., candidate or test compounds or agents (e.g., peptides, peptidomimetics, small molecules or other drugs) which bind to 14790 proteins, have a stimulatory or inhibitory effect on, for example, kinase expression or kinase activity, or have a stimulatory or inhibitory effect on, for example, the expression or activity of a kinase substrate.

In one embodiment, the invention provides assays for screening candidate or test compounds which are substrates of a 14790 protein or polypeptide or biologically active portion thereof. In another embodiment, the invention provides assays for screening candidate or test compounds which bind to or modulate the activity of a 14790 protein or polypeptide or biologically active portion thereof, e.g., modulate the ability of kinase to interact with its cognate ligand. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In another embodiment, an assay is a cell-based assay comprising contacting a cell expressing a kinase target molecule (e.g., a kinase phosphorylation substrate) with a test compound and determining the ability of the test compound to modulate (e.g. stimulate or inhibit) the activity of the kinase target molecule. Determining the ability of the test compound to modulate the activity of a kinase target molecule can be accomplished, for example, by determining the ability of the 14790 protein to bind to or interact with the target molecule, or by determining the ability of the protein to phosphorylate the kinase target molecule.

The ability of the protein to phosphorylate a kinase target molecule can be determined by, for example, an in vitro kinase assay. Briefly, a kinase target molecule, e.g., an immunoprecipitated kinase target molecule from a cell line expressing such a molecule, can be incubated with the 14790 protein and radioactive ATP, e.g., [$\gamma$-$^{32}$P] ATP, in a buffer containing $MgCl_2$ and $MnCl_2$, e.g., 10 mM $MgCl_2$ and 5 mM $MnCl_2$. Following the incubation, the immunoprecipitated kinase target molecule can be separated by SDS-polyacrylamide gel electrophoresis under reducing conditions, transferred to a membrane, e.g., a PVDF membrane, and autoradiographed. The appearance of detectable bands on the autoradiograph indicates that the kinase substrate has been phosphorylated. Phosphoaminoacid analysis of the phosphorylated substrate can also be performed in order to determine which residues on the substrate are phosphorylated. Briefly, the radiophosphorylated protein band can be excised from the SDS gel and subjected to partial acid hydrolysis. The products can then be separated by one-dimensional electrophoresis and analyzed on, for example, a phosphoimager and compared to ninhydrin-stained phosphoaminoacid standards.

Determining the ability of the 14790 protein to bind to or interact with a kinase target molecule can be accomplished by determining direct binding. Determining the ability of the 14790 protein to bind to or interact with a target molecule can be accomplished, for example, by coupling the 14790 protein with a radioisotope or enzymatic label such that binding of the protein to a kinase target molecule can be determined by detecting the labeled protein in a complex. For example, molecules, e.g., proteins, can be labeled with $^{125}$I, $^{35}$S, $^{14}$C, or $^{3}$H, either directly or indirectly, and the radioisotope detected by direct counting of radioemmission or by scintillation counting. Alternatively, molecules can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to modulate the interaction between kinase and its target molecule, without the labeling of any of the interactants. For example, a microphysiometer can be used to detect the interaction of with its target molecule without the labeling of either kinase or the target molecule. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, determining the ability of the 14790 protein to bind to or interact with a kinase target molecule can be accomplished by determining the activity of the target molecule. For example, the activity of the target molecule can be determined by detecting induction of a cellular second messenger of the target (e.g., intracellular $Ca^{2+}$, diacylglycerol, $IP_3$, etc.), detecting catalytic/enzymatic activity of the target an appropriate substrate, detecting the induction of a reporter gene (comprising a target-responsive regulatory element operatively linked to a nucleic acid encoding a detectable marker, e.g., chloramphenicol acetyl transferase), or detecting a target-regulated cellular response.

In yet another embodiment, an assay of the present invention is a cell-free assay in which a protein or biologically active portion thereof is contacted with a test compound and the ability of the test compound to bind to the 14790 protein or biologically active portion thereof is determined. Binding of the test compound to the 14790 protein can be determined either directly or indirectly as described above. In a preferred embodiment, the assay includes contacting the 14790 protein or biologically active portion thereof with a known compound which binds kinase to form an assay mixture, contacting the assay mixture with a test compound, and determining the ability of the test compound to interact with a 14790 protein, wherein determining the ability of the test compound to interact with a 14790 protein comprises determining the ability of the test compound to preferentially bind to kinase or biologically active portion thereof as compared to the known compound.

In another embodiment, the assay is a cell-free assay in which a 14790 protein or biologically active portion thereof is contacted with a test compound and the ability of the test compound to modulate (e.g., stimulate or inhibit) the activity of the 14790 protein or biologically active portion thereof is determined. Determining the ability of the test compound to modulate the activity of a 14790 protein can be accomplished, for example, by determining the ability of the 14790 protein to bind to a kinase target molecule by one of the methods described above for determining direct binding. Determining the ability of the 14790 protein to bind to a kinase target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a 14790 protein can be accomplished by determining the ability of the 14790 protein to further modulate the activity of a kinase target molecule (e.g., a kinase mediated signal transduction pathway component). For example, the activity of the effector molecule on an appropriate target can be determined, or the binding of the effector to an appropriate target can be determined as previously described.

In yet another embodiment, the cell-free assay involves contacting a 14790 protein or biologically active portion thereof with a known compound which binds the 14790 protein to form an assay mixture, contacting the assay mixture with a test compound, and determining the ability of the test compound to interact with the 14790 protein, wherein determining the ability of the test compound to interact with the 14790 protein comprises determining the ability of the 14790 protein to preferentially bind to or modulate the activity of a kinase target molecule.

The cell-free assays of the present invention are amenable to use of both soluble and/or membrane-bound forms of proteins (e.g., 14790 proteins or biologically active portions thereof, or receptors to which kinase binds). In the case of cell-free assays in which a membrane-bound form a 14790 protein is used (e.g., a cell surface kinase receptor) it may be desirable to utilize a solubilizing agent such that the membrane-bound form of the 14790 protein is maintained in solution. Examples of such solubilizing agents include nonionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl) dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either kinase or its target molecule to facilitate separation of complexed from uncomplexed forms of one or both of the proteins, as well as to accommodate automation of the assay. Binding of kinase a test compound to a protein, or interaction of a 14790 protein with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/kinase fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or 14790 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of kinase binding or activity determined using standard techniques.

Other techniques for immobilizing proteins on matrices can also be used in the screening assays of the invention. For example, either a 14790 protein or a kinase target molecule can be immobilized utilizing conjugation of biotin and streptavidin. Biotinylated 14790 protein or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with 14790 protein or target molecules but which do not interfere with binding of the 14790 protein to its target molecule can be derivatized to the wells of the plate, and unbound target or 14790 protein trapped in the wells by antibody conjugation. Methods for detecting such complexes, in addition to those described above for the GST-immobilized complexes, include immunodeection of complexes using antibodies reactive with the 14790 protein or target molecule, as well as enzyme-linked assays which rely on detecting an enzymatic activity associated with the 14790 protein or target molecule.

In another embodiment, modulators of kinase expression are identified in a method wherein a cell is contacted with a candidate compound and the expression of kinase mRNA or protein in the cell is determined. The level of expression of kinase MRNA or protein in the presence of the candidate compound is compared to the level of expression of kinase mRNA or protein in the absence of the candidate compound. The candidate compound can then be identified as a modulator of kinase expression based on this comparison. For example, when expression of kinase mRNA or protein is greater (statistically significantly greater) in the presence of the candidate compound than in its absence, the candidate compound is identified as a stimulator of kinase mRNA or protein expression. Alternatively, when expression of kinase mRNA or protein is less (statistically significantly less) in the presence of the candidate compound than in its absence, the candidate compound is identified as an inhibitor of kinase mRNA or protein expression. The level of kinase mRNA or protein expression in the cells can be determined by methods described herein for detecting kinase mRNA or protein.

In yet another aspect of the invention, the 14790 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with kinase ("kinase-binding proteins" or "kinase-bp") and are involved in kinase activity. Such kinase-binding proteins are also likely to be involved in the propagation of signals by the 14790 proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a 14790 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a kinase dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the 14790 protein which interacts with the protein.

This invention further pertains to novel agents identified by the above-described screening assays. Accordingly, it is within the scope of this invention to further use an agent identified as described herein in an appropriate animal model. For example, an agent identified as described herein (e.g., a kinase modulating agent, an antisense kinase nucleic acid molecule, a kinase-specific antibody, or a kinase-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the kinase nucleotide sequences, described herein, can be used to map the location of the kinase genes on a chromosome. The mapping of the kinase sequences to chromosomes is an important first step in correlating these sequences with genes associated with disease.

Briefly, kinase genes can be mapped to chromosomes by preparing PCR primers (preferably 15–25 bp in length) from the kinase nucleotide sequences. Computer analysis of the kinase sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the kinase sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the kinase nucleotide sequences to design oligonucleotide primers, sublocalization can be achieved with panels of fragments from specific chromosomes. Other mapping strategies which can similarly be used to map a 9o, 1p, or 1v kinase sequence to its chromosome include in situ hybridization (described in Fan, Y. et al. (1990) *Proc. Natl. Acad. Sci. USA*, 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The kinase sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the kinase nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The kinase nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can comfortably provide positive individual identification with a panel of perhaps 10 to 1,000 primers which each yield a noncoding amplified sequence of 100 bases. If predicted coding sequences, such as nucleotides 63–5012 in SEQ ID NO:1 are used, a more appropriate number of primers for positive individual identification would be 500–2,000.

If a panel of reagents from nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding regions, making it easier to differentiate individuals using this technique. Examples of polynucleotide reagents include the kinase nucleotide sequences or portions thereof, e.g., fragments derived from the noncoding regions of SEQ ID NO:1 having a length of at least 20 bases, preferably at least 30 bases.

The kinase nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such kinase probes can be used to identify tissue by species and/or by organ type.

In a similar fashion, these reagents, e.g., kinase primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining 14790 protein and/or nucleic acid expression as well as kinase activity, in the context of a biological sample (e.g., blood, serum, cells, tissue) to thereby determine whether an individual is afflicted with a disease or disorder, or is at risk of developing a disorder, associated with aberrant kinase expression or activity. The invention also provides for prognostic (or predictive) assays for determining whether an individual is at risk of developing a disorder associated with 14790 protein, nucleic acid expression or activity. For example, mutations in a kinase gene can be assayed in a biological sample. Such assays can be used for prognostic or predictive purpose to thereby phophylactically treat an individual prior to the onset of a disorder characterized by or associated with 14790 protein, nucleic acid expression or activity.

Another aspect of the invention pertains to monitoring the influence of agents (e.g., drugs, compounds) on the expression or activity of kinase in clinical trials.

These and other agents are described in further detail in the following sections.

1. Diagnostic Assays

An exemplary method for detecting the presence or absence of 14790 protein or nucleic acid in a biological sample involves obtaining a biological sample from a test subject and contacting the biological sample with a compound or an agent capable of detecting 14790 protein or nucleic acid (e.g., mRNA, genomic DNA) that encodes 14790 protein such that the presence of 14790 protein or nucleic acid is detected in the biological sample. A preferred agent for detecting mRNA or genomic DNA is a labeled nucleic acid probe capable of hybridizing to mRNA or genomic DNA. The nucleic acid probe can be, for example, a human nucleic acid, such as the nucleic acid of SEQ ID NO:1 or a portion thereof, such as an oligonucleotide of at least 15, 30, 50, 100, 250 or 500 nucleotides in length and sufficient to specifically hybridize under stringent conditions to kinase mRNA or genomic DNA. Other suitable probes for use in the diagnostic assays of the invention are described herein.

A preferred agent for detecting protein is an antibody capable of binding to protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect kinase mRNA, protein, or genomic DNA in a biological sample in vitro as well as in vivo. For example, in vitro techniques for detection of kinase mRNA include Northern hybridizations and in situ hybridizations. In vitro techniques for detection of 14790 protein include enzyme linked immunosorbent assays (ELISAs), Western blots, immunoprecipitations and immunofluorescence. In vitro techniques for detection of kinase genomic DNA include Southern hybridizations. Furthermore, in vivo techniques for detection of 14790 protein include introducing into a subject a labeled anti-kinase antibody. For example, the antibody can be labeled with a radioactive marker whose presence and location in a subject can be detected by standard imaging techniques.

In one embodiment, the biological sample contains 14790 protein molecules from the test subject. Alternatively, the biological sample can contain kinase mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting 14790 protein, mRNA, or genomic DNA, such that the presence of 14790 protein, mRNA or genomic DNA is detected in the biological sample, and comparing the presence of 14790 protein, mRNA or genomic DNA in the control sample with the presence of 14790 protein, mRNA or genomic DNA in the test sample.

The invention also encompasses kits for detecting the presence of kinase in a biological sample. For example, the kit can comprise a labeled compound or agent capable of detecting 14790 protein or mRNA in a biological sample; means for determining the amount of kinase in the sample; and means for comparing the amount of kinase in the sample with a standard. The compound or agent can be packaged in a suitable container. The kit can further comprise instructions for using the kit to detect 14790 protein or nucleic acid.

2. Prognostic Assays

The diagnostic methods described herein can furthermore be utilized to identify subjects having or at risk of developing a disease or disorder associated with aberrant kinase expression or activity. For example, the assays described herein, such as the preceding diagnostic assays or the following assays, can be utilized to identify a subject having or at risk of developing a disorder associated with 14790 protein, nucleic acid expression or activity. Thus, the present invention provides a method for identifying a disease or disorder associated with aberrant kinase expression or activity in which a test sample is obtained from a subject and 14790 protein or nucleic acid (e.g., mRNA, genomic DNA) is detected, wherein the presence of 14790 protein or nucleic acid is diagnostic for a subject having or at risk of developing a disease or disorder associated with aberrant kinase expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant kinase expression or activity. Thus, the present invention provides methods for determining whether a subject can be effectively treated with an agent for a disorder associated with aberrant kinase expression or activity in which a test sample is obtained and 14790 protein or nucleic acid expression or activity is detected (e.g., wherein the abundance of 14790 protein or nucleic acid expression or activity is diagnostic for a subject that can be administered the agent to treat a disorder associated with aberrant kinase expression or activity).

The methods of the invention can also be used to detect genetic alterations in a kinase gene, thereby determining if a subject with the altered gene is at risk for a disorder associated with the kinase gene. In preferred embodiments, the methods include detecting, in a sample of cells from the subject, the presence or absence of a genetic alteration characterized by at least one of an alteration affecting the integrity of a gene encoding a kinase-protein, or the mis-expression of the kinase gene. For example, such genetic alterations can be detected by ascertaining the existence of at least one of 1) a deletion of one or more nucleotides from a kinase gene; 2) an addition of one or more nucleotides to a kinase gene; 3) a substitution of one or more nucleotides of a kinase gene, 4) a chromosomal rearrangement of a kinase gene; 5) an alteration in the level of a messenger RNA transcript of a kinase gene, 6) aberrant modification of a kinase gene, such as of the methylation pattern of the genomic DNA, 7) the presence of a non-wild type splicing pattern of a messenger RNA transcript of a kinase gene, 8) a non-wild type level of a kinase-protein, 9) allelic loss of a gene, and 10) inappropriate post-translational modification of a kinase-protein. As described herein, there are a large number of assay techniques known in the art which can be used for detecting alterations in a kinase gene. A preferred biological sample is a tissue or serum sample isolated by conventional means from a subject, e.g., a hepatic tissue sample.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Naka-zawa et al. (1994) *Proc. Natl. Acad. Sci. USA* 91:360–364), the latter of which can be particularly useful for detecting point mutations in the kinase-gene (see Abravaya et al. (1995) *Nucleic Acids Res*. 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a kinase gene under conditions such that hybridization and amplification of the kinase-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al.

(1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a kinase gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in kinase can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in kinase can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential ovelapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the kinase gene and detect mutations by comparing the sequence of the kinase sample with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) Adv. Chromatogr. 36:127–162; and Griffin et al. (1993) *Appl. Biochem. Biotechnol.* 38:147–159).

Other methods for detecting mutations in the kinase gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes formed by hybridizing (labeled) RNA or DNA containing the wild-type kinase sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in kinase cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on kinase a sequence, e.g., a wild-type kinase sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in kinase genes. For example, single strand conformation polymorphism (SSCP) may be used to detect differences in electrophoretic mobility between mutant and wild type nucleic acids (Orita et al. (1989) *Proc Natl. Acad. Sci USA*: 86:2766, see also Cotton (1993) *Mutat Res* 285:125–144; and Hayashi (1992) *Genet Anal Tech Appl* 9:73–79). Single-stranded DNA fragments of sample and control kinase nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner et al. (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a kinase gene.

Furthermore, any cell type or tissue in which kinase is expressed may be utilized in the prognostic assays described herein.

3. Monitoring of Effects During Clinical Trials

Monitoring the influence of agents (e.g., drugs or compounds) on the expression or activity of a 14790 protein can be applied not only in basic drug screening, but also in clinical trials. For example, the effectiveness of an agent determined by a screening assay as described herein to increase kinase gene expression, protein levels, or upregulate kinase activity, can be monitored in clinical trials of subjects exhibiting decreased kinase gene expression, protein levels, or downregulated kinase activity. Alternatively, the effectiveness of an agent determined by a screening assay to decrease kinase gene expression, protein levels, or downregulate kinase activity, can be monitored in clinical trials of subjects exhibiting increased kinase gene expression, protein levels, or upregulated activity. In such clinical trials, the expression or activity of a kinase gene, and preferably, other genes that have been implicated in a disorder can be used as a "read out" or markers of the phenotype of a particular cell.

For example, and not by way of limitation, genes, including kinase, that are modulated in cells by treatment with an agent (e.g., compound, drug or small molecule) which modulates kinase activity (e.g., identified in a screening assay as described herein) can be identified. Thus, to study the effect of agents on a kinase associated disorder, for example, in a clinical trial, cells can be isolated and RNA prepared and analyzed for the levels of expression of kinase and other genes implicated in the kinase associated disorder, respectively. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of kinase or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a 14790 protein, mRNA, or genomic DNA in the pre-administration sample; (iii) obtaining one or more post-administration samples from the subject; (iv) detecting the level of expression or activity of the 14790 protein, mRNA, or genomic DNA in the post-administration samples; (v) comparing the level of expression or activity of the 14790 protein, mRNA, or genomic DNA in the pre-administration sample with the 14790 protein, mRNA, or genomic DNA in the post administration sample or samples; and (vi) altering the administration of the agent to the subject accordingly. For example, increased administration of the agent may be desirable to increase the expression or activity of kinase to higher levels than detected, i.e., to increase the effectiveness of the agent. Alternatively, decreased administration of the agent may be desirable to decrease expression or activity of kinase to lower levels than detected, i.e. to decrease the effectiveness of the agent. According to such an embodiment, kinase expression or activity may be used as an indicator of the effectiveness of an agent, even in the absence of an observable phenotypic response.

C. Methods of Treatment:

The present invention provides for both prophylactic and therapeutic methods of treating a subject at risk of (or susceptible to) a disorder or having a disorder associated with aberrant kinase expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 14790 molecules of the present invention or kinase modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant kinase expression or activity, by administering to the subject a or an agent which modulates kinase expression or at least one kinase activity. Subjects at risk for a disease which is caused or contributed to by aberrant kinase expression or activity can be identified by, for example, any or a combination of diagnostic or prognostic assays as described herein. Administration of a prophylactic agent can occur prior to the manifestation of symptoms characteristic of kinase aberrancy, such that a disease or disorder is prevented or, alternatively, delayed in its progression. Depending on the type of kinase aberrancy, for example, a kinase, kinase agonist or kinase antagonist agent can be used for treating the subject. The appropriate agent can be determined based on screening assays described herein.

2. Therapeutic Methods

Another aspect of the invention pertains to methods of modulating kinase expression or activity for therapeutic purposes. Accordingly, in an exemplary embodiment, the modulatory method of the invention involves contacting a cell with a kinase or agent that modulates one or more of the activities of 14790 protein activity associated with the cell. An agent that modulates 14790 protein activity can be an agent as described herein, such as a nucleic acid or a protein, a naturally-occurring target molecule of a 14790 protein (e.g., a kinase phosphorylation substrate), a kinase antibody, a kinase agonist or antagonist, a peptidomimetic of a kinase agonist or antagonist, or other small molecule. In one embodiment, the agent stimulates one or more kinase activities. Examples of such stimulatory agents include active 14790 protein and a nucleic acid molecule encoding kinase that has been introduced into the cell. In another embodiment, the agent inhibits one or more kinase activites. Examples of such inhibitory agents include antisense kinase nucleic acid molecules, anti-kinase antibodies, and kinase inhibitors. These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of a 14790 protein or nucleic acid molecule. In one embodiment, the method involves administering an agent (e.g., an agent identified by a screening assay described herein), or combination of agents that modulates (e.g., upregulates or downregulates) kinase expression or activity. In another embodiment, the method involves administering a 14790 protein or nucleic acid molecule as therapy to compensate for reduced or aberrant kinase expression or activity.

Stimulation of kinase activity is desirable in situations in which kinase is abnormally downregulated and/or in which increased kinase activity is likely to have a beneficial effect. For example, stimulation of kinase activity is desirable in situations in which a kinase is downregulated and/or in which increased kinase activity is likely to have a beneficial effect. Likewise, inhibition of kinase activity is desirable in situations in which kinase is abnormally upregulated and/or in which decreased kinase activity is likely to have a beneficial effect.

3. Pharmacogenomics

The 14790 molecules of the present invention, as well as agents, or modulators which have a stimulatory or inhibitory effect on kinase activity (e.g., kinase gene expression) as identified by a screening assay described herein can be administered to individuals to treat (prophylactically or therapeutically) disorders (e.g, infection with HBV) associated with aberrant kinase activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 14790 molecule or kinase modulator as well as tailoring the dosage and/or therapeutic regimen of treatment with a 14790 molecule or kinase modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–11):983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict a drug response. According to this method, if a gene that encodes a drug target is known (e.g., a 14790 protein or kinase receptor of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a 14790 molecule or kinase modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a 14790 molecule or kinase modulator, such as a modulator identified by one of the exemplary screening assays described herein.

This invention is further illustrated by the following examples which should not be construed as limiting. The contents of all references, patents and published patent applications cited throughout this application are incorporated herein by reference.

EXAMPLES

Example 1

Identification and Characterization of Human cDNA

Isolation of the Human cDNA

The invention is based, at least in part, on the discovery of a human gene encoding a novel member of the kinase family. The human kinase family members were isolated from cDNA. A cDNA library was prepared therefrom using art known methods (described in, for example, *Molecular Cloning A Laboratory Manual*, 2nd Ed., ed. by Sambrook, Fritsch and Maniatis (Cold Spring Harbor Laboratory Press: 1989). Positive clones were isolated following comparison to homologs in public protein databases, including a comparison with known kinases and/or examination of the sequence for protein motifs of kinases.

The sequences of the positive clones were determined and found to contain open reading frames. The nucleotide sequence encoding the human 14790 protein is shown in FIG. 1 and is set forth as SEQ ID NO:1. The protein encoded by this nucleic acid comprises about 1649 amino acids and has the amino acid sequence shown in FIG. 1 and set forth as SEQ ID NO:2. The coding region (open reading frame) of SEQ ID NO:1 is shown in FIG. 1 as the portion of the nucleotide sequence corresponding to the amino acid sequence of SEQ ID NO:2.

Analysis of Human 14790 Molecule

A BLASTN 1.4.9 search, using a score of 100 and a word length of 12 (Altschul et al. (1990) *J. Mol. Biol.* 215:403) of the nucleotide sequence of human kinase revealed that kinase is similar to the human protein kinase HPK-1 coding sequence (Accession No. V23831). This nucleic acid molecule is approximately 70% identical to kinase, over nucleotides 388–1214.

Tissue Distribution of Kinase mRNA

This Example describes the tissue distribution of kinase mRNA, as determined by TaqMan RT-PCR and in situ hybridization.

14790 mRNA was found to be expressed in human skeletal muscle, brain and liver. TaqMan RT-PCR analysis revealed that 14790 mRNA was found to be upregulated in liver cells which were infected with HBV. Moreover, mRNA expression of 14790 was found to be restricted to hepatocytes of HBV infected livers as seen by in situ hybridization. 14790 mRNA was also found to be upregulated in HepG2.2.15 cells (HBV positive) compared to HepG2 parent cells (HBV negative). When HepG2.2.15 cells were treated with anti-HBV drug treatment, the upregulation of 14790 mRNA was eliminated. Thus indicating that a modulator of 14790 activity or mRNA may be used to treat infection by HBV.

Equivalents

Those skilled in the art will recognize, or be able to ascertain using no more than routine experimentation, many equivalents to the specific embodiments of the invention described herein. Such equivalents are intended to be encompassed by the following claims.

SEQUENCE LISTING

<160> NUMBER OF SEQ ID NOS: 33

<210> SEQ ID NO 1
<211> LENGTH: 5525
<212> TYPE: DNA
<213> ORGANISM: Homo sapiens
<220> FEATURE:
<221> NAME/KEY: CDS
<222> LOCATION: (63)...(5012)

<400> SEQUENCE: 1
tcgccccacg cgtccgcacc gccgcccagg caaggccgcc ctgccttggg cgcagcgctg    60

-continued

```
cc atg gct ggg ggc cgt ggg gcc ccc ggg cgc ggc cgg gac gag cct         107
   Met Ala Gly Gly Arg Gly Ala Pro Gly Arg Gly Arg Asp Glu Pro
    1               5                  10                  15 ccg gag agc tac ccg caa cga cag gac cac gag cta cag gcc ctg gag         155
Pro Glu Ser Tyr Pro Gln Arg Gln Asp His Glu Leu Gln Ala Leu Glu
                 20                  25                  30 gcc atc tac ggc gcg gac ttc caa gac ctg cgg ccg gac gct tgc gga         203
Ala Ile Tyr Gly Ala Asp Phe Gln Asp Leu Arg Pro Asp Ala Cys Gly
             35                  40                  45 ccg gtc aaa gag ccc cct gaa atc aat tta gtt ttg tac cct caa ggc         251
Pro Val Lys Glu Pro Pro Glu Ile Asn Leu Val Leu Tyr Pro Gln Gly
         50                  55                  60 cta act ggt gaa gaa gta tat gta aaa gtg gat ttg agg gtt aaa tgc         299
Leu Thr Gly Glu Glu Val Tyr Val Lys Val Asp Leu Arg Val Lys Cys
     65                  70                  75 cca cct acc tat cca gat gta gtt cct gaa ata gag tta aaa aat gcc         347
Pro Pro Thr Tyr Pro Asp Val Val Pro Glu Ile Glu Leu Lys Asn Ala
 80                  85                  90                  95 aaa ggt cta tca aat gaa agt gtc aat ttg tta aaa tct cgc cta gaa         395
Lys Gly Leu Ser Asn Glu Ser Val Asn Leu Leu Lys Ser Arg Leu Glu
                100                 105                 110 gaa ctg gcc aag aaa cac tgt ggg gag gtg atg atc ttt gaa ctg gct         443
Glu Leu Ala Lys Lys His Cys Gly Glu Val Met Ile Phe Glu Leu Ala
            115                 120                 125 tac cac gtg cag tca ttt ctc agc gag cat aac aag ccc cct ccc aag         491
Tyr His Val Gln Ser Phe Leu Ser Glu His Asn Lys Pro Pro Pro Lys
        130                 135                 140 tct ttt cat gaa gaa atg ctg gaa agg cgg gct cag gag gag cag cag         539
Ser Phe His Glu Glu Met Leu Glu Arg Arg Ala Gln Glu Glu Gln Gln
    145                 150                 155 agg ctg ttg gag gcc aag cgg aaa gaa gag cag gag caa cgt gaa atc         587
Arg Leu Leu Glu Ala Lys Arg Lys Glu Glu Gln Glu Gln Arg Glu Ile
160                 165                 170                 175 ctg cat gag att cag aga agg aaa gaa gag ata aaa gaa gag aaa aaa         635
Leu His Glu Ile Gln Arg Arg Lys Glu Glu Ile Lys Glu Glu Lys Lys
                180                 185                 190 agg aaa gaa atg gct aag cag gaa cgt ttg gaa att gct agt ttg tca         683
Arg Lys Glu Met Ala Lys Gln Glu Arg Leu Glu Ile Ala Ser Leu Ser
            195                 200                 205 aac caa gat cat acc tct aag aag gac cca gga gga cac aga acg gct         731
Asn Gln Asp His Thr Ser Lys Lys Asp Pro Gly Gly His Arg Thr Ala
        210                 215                 220 gcc att cta cat gga ggc tct cct gac ttt gta gga aat ggt aaa cat         779
Ala Ile Leu His Gly Gly Ser Pro Asp Phe Val Gly Asn Gly Lys His
    225                 230                 235 cgg gca aac tcc tca gga agg tct agg cga gaa cgt cag tat tct gta         827
Arg Ala Asn Ser Ser Gly Arg Ser Arg Arg Glu Arg Gln Tyr Ser Val
240                 245                 250                 255 tgt aat agt gaa gat tct cct ggc tct tgt gaa att ctg tat ttc aat         875
Cys Asn Ser Glu Asp Ser Pro Gly Ser Cys Glu Ile Leu Tyr Phe Asn
                260                 265                 270 atg ggg agt cct gat cag ctc atg gtg cac aaa ggg aaa tgt att ggc         923
Met Gly Ser Pro Asp Gln Leu Met Val His Lys Gly Lys Cys Ile Gly
            275                 280                 285 agt gat gaa caa ctt gga aaa tta gtc tac aat gct ttg gaa aca gcc         971
Ser Asp Glu Gln Leu Gly Lys Leu Val Tyr Asn Ala Leu Glu Thr Ala
        290                 295                 300 act ggt ggc ttt gtc ttg ttg tat gag tgg gtc ctt cag tgg cag aaa        1019
Thr Gly Gly Phe Val Leu Leu Tyr Glu Trp Val Leu Gln Trp Gln Lys
    305                 310                 315
```

```
aaa atg ggt cca ttc ctt acc agt caa gaa aaa gag aag att gat aag   1067
Lys Met Gly Pro Phe Leu Thr Ser Gln Glu Lys Glu Lys Ile Asp Lys
320             325                 330                 335 tgc aaa aag cag att caa gga aca gaa aca gaa ttc aac tca ctg gta   1115
Cys Lys Lys Gln Ile Gln Gly Thr Glu Thr Glu Phe Asn Ser Leu Val
            340                 345                 350 aaa ttg agc cat cca aat gta gta cgc tac ctt gca atg aat ctc aaa   1163
Lys Leu Ser His Pro Asn Val Val Arg Tyr Leu Ala Met Asn Leu Lys
        355                 360                 365 gag caa gac gac tcc atc gtg gtg gac att tta gtg gag cac att agt   1211
Glu Gln Asp Asp Ser Ile Val Val Asp Ile Leu Val Glu His Ile Ser
    370                 375                 380 ggg gtc tct ctt gct gca cac ctg agc cac tca ggc ccc atc cct gtg   1259
Gly Val Ser Leu Ala Ala His Leu Ser His Ser Gly Pro Ile Pro Val
385                 390                 395 cat cag ctt cgc agg tac aca gct cag ctc ctg tca ggc ctt gat tat   1307
His Gln Leu Arg Arg Tyr Thr Ala Gln Leu Leu Ser Gly Leu Asp Tyr
400                 405                 410                 415 ctg cac agc aat tct gtg gtg cat aag gtc ctg agt gca tct aat gtc   1355
Leu His Ser Asn Ser Val Val His Lys Val Leu Ser Ala Ser Asn Val
            420                 425                 430 ttg gtg gat gca gaa ggc acc gtc aag att acg gac tat agc att tct   1403
Leu Val Asp Ala Glu Gly Thr Val Lys Ile Thr Asp Tyr Ser Ile Ser
        435                 440                 445 aag cgc ctc gca gac att tgc aag gag gat gtg ttt gag caa acc cga   1451
Lys Arg Leu Ala Asp Ile Cys Lys Glu Asp Val Phe Glu Gln Thr Arg
    450                 455                 460 gtt cgt ttt agt gac aat gct ctg cct tat aaa acg ggg aag aaa gga   1499
Val Arg Phe Ser Asp Asn Ala Leu Pro Tyr Lys Thr Gly Lys Lys Gly
465                 470                 475 gat gtt tgg cgt ctt ggc ctt ctg ctg tcc ctc agc caa gga cag       1547
Asp Val Trp Arg Leu Gly Leu Leu Leu Ser Leu Ser Gln Gly Gln
480                 485                 490                 495 gaa tgt gga gag tac cct gtg acc atc cct agt gac tta cca gct gac   1595
Glu Cys Gly Glu Tyr Pro Val Thr Ile Pro Ser Asp Leu Pro Ala Asp
            500                 505                 510 ttt caa gat ttt cta aag aaa tgt gtg tgc ttg gat gac aag gaa aga   1643
Phe Gln Asp Phe Leu Lys Lys Cys Val Cys Leu Asp Asp Lys Glu Arg
        515                 520                 525 tgg agt ccc cag cag ttg ttg aaa cac agc ttt ata aat ccc cag cca   1691
Trp Ser Pro Gln Gln Leu Leu Lys His Ser Phe Ile Asn Pro Gln Pro
    530                 535                 540 aaa atg cct cta gtg gaa caa agt cct gaa gat tct gga gga caa gat   1739
Lys Met Pro Leu Val Glu Gln Ser Pro Glu Asp Ser Gly Gly Gln Asp
545                 550                 555 tat gtt gag act gtt att cct agc aac cgg cta ccc agt gct gcc ttc   1787
Tyr Val Glu Thr Val Ile Pro Ser Asn Arg Leu Pro Ser Ala Ala Phe
560                 565                 570                 575 ttt agt gag aca cag aga cag ttt tcc cga tac ttc att gag ttt gaa   1835
Phe Ser Glu Thr Gln Arg Gln Phe Ser Arg Tyr Phe Ile Glu Phe Glu
            580                 585                 590 gaa tta caa ctt ctt ggt aaa gga gct ttt gga gct gtc atc aag gtg   1883
Glu Leu Gln Leu Leu Gly Lys Gly Ala Phe Gly Ala Val Ile Lys Val
        595                 600                 605 cag aac aag ttg gac ggc tgc tgc tac gca gtg aag cgc atc ccc atc   1931
Gln Asn Lys Leu Asp Gly Cys Cys Tyr Ala Val Lys Arg Ile Pro Ile
    610                 615                 620 aac ccg gcc agc cgg cag ttc cgc agg atc aag ggc gaa gtg aca ctg   1979
Asn Pro Ala Ser Arg Gln Phe Arg Arg Ile Lys Gly Glu Val Thr Leu
```

-continued

|  |  |  |  |  |  |  |  |  |  |  |  |  |  |  |  |
|---|---|---|---|---|---|---|---|---|---|---|---|---|---|---|---|
|  |  | 625 |  |  |  | 630 |  |  |  | 635 |  |  |  |  |  | ctg tca cgg ctg cac cat gag aac att gtg cgc tac tac aac gcc tgg  2027
Leu Ser Arg Leu His His Glu Asn Ile Val Arg Tyr Tyr Asn Ala Trp
640                 645                 650                 655 atc gag cgg cac gag cgg ccg gcg gga ccg ggg acg ccg ccc ccg gac  2075
Ile Glu Arg His Glu Arg Pro Ala Gly Pro Gly Thr Pro Pro Pro Asp
            660                 665                 670 tcc ggg ccc ctg gcc aag gat gac cga gct gca cgc ggg cag ccg gcg  2123
Ser Gly Pro Leu Ala Lys Asp Asp Arg Ala Ala Arg Gly Gln Pro Ala
        675                 680                 685 agc gac aca gac ggc ctg gac agc gta gag gcc gcc gcg ccg cca ccc  2171
Ser Asp Thr Asp Gly Leu Asp Ser Val Glu Ala Ala Ala Pro Pro Pro
    690                 695                 700 atc ctc agc agc tcg gtg gag tgg agc act tcg ggc gag cgc tcg gcc  2219
Ile Leu Ser Ser Ser Val Glu Trp Ser Thr Ser Gly Glu Arg Ser Ala
705                 710                 715 agt gcc cgt ttc ccc gcc acc ggc ccg ggc tcc agc gat gac gag gac  2267
Ser Ala Arg Phe Pro Ala Thr Gly Pro Gly Ser Ser Asp Asp Glu Asp
720                 725                 730                 735 gac gac gag gac gag cac ggt ggc gtc ttc tcc cag tcc ttc ctg cct  2315
Asp Asp Glu Asp Glu His Gly Gly Val Phe Ser Gln Ser Phe Leu Pro
                740                 745                 750 gct tca gat tct gaa agt gat att atc ttt gac aat gaa gat gag aac  2363
Ala Ser Asp Ser Glu Ser Asp Ile Ile Phe Asp Asn Glu Asp Glu Asn
            755                 760                 765 agt aaa agt cag aat cag gat gaa gat tgc aat gaa aag aat ggc tgc  2411
Ser Lys Ser Gln Asn Gln Asp Glu Asp Cys Asn Glu Lys Asn Gly Cys
        770                 775                 780 cat gaa agt gag cca tca gtg acg act gag gct gtg cac tac cta tac  2459
His Glu Ser Glu Pro Ser Val Thr Thr Glu Ala Val His Tyr Leu Tyr
    785                 790                 795 atc cag atg gag tac tgt gag aag agc act tta cga gac acc att gac  2507
Ile Gln Met Glu Tyr Cys Glu Lys Ser Thr Leu Arg Asp Thr Ile Asp
800                 805                 810                 815 cag gga ctg tat cga gac acc gtc aga ctc tgg agg ctt ttt cga gag  2555
Gln Gly Leu Tyr Arg Asp Thr Val Arg Leu Trp Arg Leu Phe Arg Glu
                820                 825                 830 att ctg gat gga tta gct tat atc cat gag aaa gga atg att cac cgg  2603
Ile Leu Asp Gly Leu Ala Tyr Ile His Glu Lys Gly Met Ile His Arg
            835                 840                 845 gat ttg aag cct gtc aac att ttt ttg gat tct gat gac cat gtg aaa  2651
Asp Leu Lys Pro Val Asn Ile Phe Leu Asp Ser Asp Asp His Val Lys
        850                 855                 860 ata ggt gat ttt ggt ttg gcg aca gac cat cta gcc ttt tct gct gac  2699
Ile Gly Asp Phe Gly Leu Ala Thr Asp His Leu Ala Phe Ser Ala Asp
    865                 870                 875 agc aaa caa gac gat cag aca gga gac ttg att aag tca gac cct tca  2747
Ser Lys Gln Asp Asp Gln Thr Gly Asp Leu Ile Lys Ser Asp Pro Ser
880                 885                 890                 895 ggt cac tta act ggg atg gtt ggc act gct ctc tat gta agc cca gag  2795
Gly His Leu Thr Gly Met Val Gly Thr Ala Leu Tyr Val Ser Pro Glu
                900                 905                 910 gtc caa gga agc acc aaa tct gca tac aac cag aaa gtg gat ctc ttc  2843
Val Gln Gly Ser Thr Lys Ser Ala Tyr Asn Gln Lys Val Asp Leu Phe
            915                 920                 925 agc ctg gga att atc ttc ttt gag atg tcc tat cac ccc atg gtc acg  2891
Ser Leu Gly Ile Ile Phe Phe Glu Met Ser Tyr His Pro Met Val Thr
        930                 935                 940 gct tca gaa agg atc ttt gtt ctc aac caa ctc aga gat ccc act tcg  2939

```
                                                                      -continued Ala Ser Glu Arg Ile Phe Val Leu Asn Gln Leu Arg Asp Pro Thr Ser
    945                 950                 955 cct aag ttt cca gaa gac ttt gac gat gga gag cat gca aag cag aaa      2987
Pro Lys Phe Pro Glu Asp Phe Asp Asp Gly Glu His Ala Lys Gln Lys
960                 965                 970                 975 tca gtc atc tcc tgg ctg ttg aac cac gat cca gca aaa cgg ccc aca      3035
Ser Val Ile Ser Trp Leu Leu Asn His Asp Pro Ala Lys Arg Pro Thr
                980                 985                 990 gcc aca gaa ctg ctc aag agt gag ctg ctc ccc cca ccc cag atg gag      3083
Ala Thr Glu Leu Leu Lys Ser Glu Leu Leu Pro Pro Pro Gln Met Glu
            995                1000               1005 gag tca gag ctg cat gaa gtg ctg cac cac acg ctg acc aac gtg gat      3131
Glu Ser Glu Leu His Glu Val Leu His His Thr Leu Thr Asn Val Asp
        1010                1015               1020 ggg aag gcc tac cgc acc atg atg gcc cag atc ttc tcg cag cgc atc      3179
Gly Lys Ala Tyr Arg Thr Met Met Ala Gln Ile Phe Ser Gln Arg Ile
    1025                1030               1035 tcc cct gcc atc gat tac acc tat gac agc gac ata ctg aag ggc aac      3227
Ser Pro Ala Ile Asp Tyr Thr Tyr Asp Ser Asp Ile Leu Lys Gly Asn
1040               1045                1050                1055 ttc tca atc cgt aca gcc aag atg cag cag cat gtg tgt gaa acc atc      3275
Phe Ser Ile Arg Thr Ala Lys Met Gln Gln His Val Cys Glu Thr Ile
                1060                1065                1070 atc cgc atc ttt aaa aga cat gga gct gtt cag ttg tgt act cca cta      3323
Ile Arg Ile Phe Lys Arg His Gly Ala Val Gln Leu Cys Thr Pro Leu
            1075                1080                1085 ctg ctt ccc cga aac aga caa ata tat gag cac aac gaa gct gcc cta      3371
Leu Leu Pro Arg Asn Arg Gln Ile Tyr Glu His Asn Glu Ala Ala Leu
        1090                1095                1100 ttc atg gac cac agc ggg atg ctg gtg atg ctt cct ttt gac ctg cgg      3419
Phe Met Asp His Ser Gly Met Leu Val Met Leu Pro Phe Asp Leu Arg
    1105                1110                1115 atc cct ttt gca aga tat gtg gca aga aat aat ata ttg aat tta aaa      3467
Ile Pro Phe Ala Arg Tyr Val Ala Arg Asn Asn Ile Leu Asn Leu Lys
1120                1125                1130                1135 cga tac tgc ata gaa cgt gtg ttc agg ccg cgc aag tta gat cga ttt      3515
Arg Tyr Cys Ile Glu Arg Val Phe Arg Pro Arg Lys Leu Asp Arg Phe
                1140                1145                1150 cat ccc aaa gaa ctt ctg gag tgt gca ttt gat att gtc act tct acc      3563
His Pro Lys Glu Leu Leu Glu Cys Ala Phe Asp Ile Val Thr Ser Thr
            1155                1160                1165 acc aac agc ttt ctg ccc act gct gaa att atc tac act atc tat gaa      3611
Thr Asn Ser Phe Leu Pro Thr Ala Glu Ile Ile Tyr Thr Ile Tyr Glu
        1170                1175                1180 atc atc caa gag ttt cca gca ctt cag gaa aga aat tac agt att tat      3659
Ile Ile Gln Glu Phe Pro Ala Leu Gln Glu Arg Asn Tyr Ser Ile Tyr
    1185                1190                1195 ttg aac cat acc atg tta ttg aaa gca ata ctc tta cac tgt ggg atc      3707
Leu Asn His Thr Met Leu Leu Lys Ala Ile Leu Leu His Cys Gly Ile
1200                1205                1210                1215 cca gaa gat aaa ctc agt caa gtc tac att att ctg tat gat gct gtg      3755
Pro Glu Asp Lys Leu Ser Gln Val Tyr Ile Ile Leu Tyr Asp Ala Val
                1220                1225                1230 aca gag aag ctg acg agg aga gaa gtg gaa gct aaa ttt tgt aat ctg      3803
Thr Glu Lys Leu Thr Arg Arg Glu Val Glu Ala Lys Phe Cys Asn Leu
            1235                1240                1245 tct ttg tct tct aat agt ctg tgt cga ctc tac aag ttt att gaa cag      3851
Ser Leu Ser Ser Asn Ser Leu Cys Arg Leu Tyr Lys Phe Ile Glu Gln
        1250                1255                1260
```

```
aag gga gat ttg caa gat ctt atg cca aca ata aat tca tta ata aaa    3899
Lys Gly Asp Leu Gln Asp Leu Met Pro Thr Ile Asn Ser Leu Ile Lys
    1265                1270                1275 cag aaa aca ggt att gca cag ttg gtg aag tat ggc tta aaa gac cta    3947
Gln Lys Thr Gly Ile Ala Gln Leu Val Lys Tyr Gly Leu Lys Asp Leu
1280                1285                1290                1295 gag gag gtt gtt gga ctg ttg aag aaa ctc ggc atc aag tta cag gtc    3995
Glu Glu Val Val Gly Leu Leu Lys Lys Leu Gly Ile Lys Leu Gln Val
                1300                1305                1310 ttg atc aat ttg ggc ttg gtt tac aag gtg cag cag cac aat gga atc    4043
Leu Ile Asn Leu Gly Leu Val Tyr Lys Val Gln Gln His Asn Gly Ile
            1315                1320                1325 atc ttc cag ttt gtg gct ttc atc aaa cga agg caa agg gct gta cct    4091
Ile Phe Gln Phe Val Ala Phe Ile Lys Arg Arg Gln Arg Ala Val Pro
        1330                1335                1340 gaa atc ctc gca gct gga ggc aga tat gac ctg ctg att ccc cag ttt    4139
Glu Ile Leu Ala Ala Gly Gly Arg Tyr Asp Leu Leu Ile Pro Gln Phe
    1345                1350                1355 aga ggg cca caa gct ctg ggg cca gtt ccc act gcc att ggg gtc agc    4187
Arg Gly Pro Gln Ala Leu Gly Pro Val Pro Thr Ala Ile Gly Val Ser
1360                1365                1370                1375 ata gct ata gac aag ata tct gct gct gtc ctc aac atg gag gaa tct    4235
Ile Ala Ile Asp Lys Ile Ser Ala Ala Val Leu Asn Met Glu Glu Ser
                1380                1385                1390 gtt aca ata agc tct tgt gac ctc ctg gtt gta agt gtt ggt cag atg    4283
Val Thr Ile Ser Ser Cys Asp Leu Leu Val Val Ser Val Gly Gln Met
            1395                1400                1405 tct atg tcc agg gcc atc aac cta acc cag aaa ctc tgg aca gca ggc    4331
Ser Met Ser Arg Ala Ile Asn Leu Thr Gln Lys Leu Trp Thr Ala Gly
        1410                1415                1420 atc aca gca gaa atc atg tac gac tgg tca cag tcc caa gag gaa tta    4379
Ile Thr Ala Glu Ile Met Tyr Asp Trp Ser Gln Ser Gln Glu Glu Leu
    1425                1430                1435 caa gag tac tgc aga cat cat gaa atc acc tat gtg gcc ctt gtc tcg    4427
Gln Glu Tyr Cys Arg His His Glu Ile Thr Tyr Val Ala Leu Val Ser
1440                1445                1450                1455 gat aaa gaa gga agc cat gtc aag gtt aag tct ttc gag aag gaa agg    4475
Asp Lys Glu Gly Ser His Val Lys Val Lys Ser Phe Glu Lys Glu Arg
                1460                1465                1470 cag aca gag aag cgt gtg ctg gag act gaa ctt gtg gac cat gta ctg    4523
Gln Thr Glu Lys Arg Val Leu Glu Thr Glu Leu Val Asp His Val Leu
            1475                1480                1485 cag aaa ctg agg act aaa gtc act gat gaa agg aat ggc aga gaa gct    4571
Gln Lys Leu Arg Thr Lys Val Thr Asp Glu Arg Asn Gly Arg Glu Ala
        1490                1495                1500 tcc gat aat ctt gca gtg caa aat ctg aag ggg tca ttt tct aat gct    4619
Ser Asp Asn Leu Ala Val Gln Asn Leu Lys Gly Ser Phe Ser Asn Ala
    1505                1510                1515 tca ggt ttg ttt gaa atc cat gga gca aca gtg gtt ccc att gtg agt    4667
Ser Gly Leu Phe Glu Ile His Gly Ala Thr Val Val Pro Ile Val Ser
1520                1525                1530                1535 gtg cta gcc ccg gag aag ctg tca gcc agc act agg agg cgc tat gaa    4715
Val Leu Ala Pro Glu Lys Leu Ser Ala Ser Thr Arg Arg Arg Tyr Glu
                1540                1545                1550 act cag gta caa act cga ctt cag acc tcc ctt gcc aac tta cat cag    4763
Thr Gln Val Gln Thr Arg Leu Gln Thr Ser Leu Ala Asn Leu His Gln
            1555                1560                1565 aaa agc agt gaa att gaa att ctg gct gtg gat cta ccc aaa gaa aca    4811
Lys Ser Ser Glu Ile Glu Ile Leu Ala Val Asp Leu Pro Lys Glu Thr
        1570                1575                1580
```

-continued

```
ata tta cag ttt tta tca tta gag tgg gat gct gat gaa cag gca ttt    4859
Ile Leu Gln Phe Leu Ser Leu Glu Trp Asp Ala Asp Glu Gln Ala Phe
    1585                1590                1595 aac aca act gtg aag cag ctg ctg tca cgc ctg cca aag caa aga tac    4907
Asn Thr Thr Val Lys Gln Leu Leu Ser Arg Leu Pro Lys Gln Arg Tyr
1600                1605                1610                1615 ctc aaa tta gtc tgt gat gaa att tat aac atc aaa gta gaa aaa aag    4955
Leu Lys Leu Val Cys Asp Glu Ile Tyr Asn Ile Lys Val Glu Lys Lys
                1620                1625                1630 gtg tct gtg cta ttt ctg tac agc tat aga gat gac tac tac aga atc    5003
Val Ser Val Leu Phe Leu Tyr Ser Tyr Arg Asp Asp Tyr Tyr Arg Ile
            1635                1640                1645 tta ttt taa ccctaaagaa ctgtcgttaa cctcattcaa acagacagag             5052
Leu Phe * gcttatactg gaataatgga atgttgtaca ttcatcataa tttaaaatta aattctaaga   5112
agaggctggg tgcagtggct cacacctta atcccagcac tttgggaagc caaggcagga   5172
agactgcttg aaaccaggag tttgagacca gcctgagcaa caaagcaaga ccccatctct   5232
ataaaaacta aaaaaattag ttgggcatgg tggcacatgc ctgtagtccc agctactcca   5292
gaggctgaga tggatcatct gagcctcagg aggttgaggc tgcagtgagc tgtgactgcg   5352
ccactgcact ccagtctggg acaacagagc aagaccctgt cttaaaaaaa aaagaaaaa   5412 aaaatttttt ttctaagaag ctgtcctaca aagttgagct tgttagtttt ttcatgtgta   5472
atatattata aatttatctt ttgggatata ataaatgctt tcatataccta gca        5525
```

<210> SEQ ID NO 2
<211> LENGTH: 1649
<212> TYPE: PRT
<213> ORGANISM: Homo sapiens

<400> SEQUENCE: 2

```
Met Ala Gly Gly Arg Gly Ala Pro Gly Arg Gly Arg Asp Glu Pro Pro
1               5                   10                  15

Glu Ser Tyr Pro Gln Arg Gln Asp His Glu Leu Gln Ala Leu Glu Ala
                20                  25                  30

Ile Tyr Gly Ala Asp Phe Gln Asp Leu Arg Pro Asp Ala Cys Gly Pro
            35                  40                  45

Val Lys Glu Pro Pro Glu Ile Asn Leu Val Leu Tyr Pro Gln Gly Leu
        50                  55                  60

Thr Gly Glu Glu Val Tyr Val Lys Val Asp Leu Arg Val Lys Cys Pro
65                  70                  75                  80

Pro Thr Tyr Pro Asp Val Val Pro Glu Ile Glu Leu Lys Asn Ala Lys
                85                  90                  95

Gly Leu Ser Asn Glu Ser Val Asn Leu Leu Lys Ser Arg Leu Glu Glu
                100                 105                 110

Leu Ala Lys Lys His Cys Gly Glu Val Met Ile Phe Glu Leu Ala Tyr
            115                 120                 125

His Val Gln Ser Phe Leu Ser Glu His Asn Lys Pro Pro Lys Ser
        130                 135                 140

Phe His Glu Glu Met Leu Glu Arg Arg Ala Gln Glu Glu Gln Gln Arg
145                 150                 155                 160

Leu Leu Glu Ala Lys Arg Lys Glu Glu Gln Glu Gln Arg Glu Ile Leu
                165                 170                 175

His Glu Ile Gln Arg Arg Lys Glu Glu Ile Lys Glu Glu Lys Lys Arg
```

-continued

```
            180                 185                 190
Lys Glu Met Ala Lys Gln Glu Arg Leu Glu Ile Ala Ser Leu Ser Asn
            195                 200                 205
Gln Asp His Thr Ser Lys Lys Asp Pro Gly Gly His Arg Thr Ala Ala
            210                 215                 220
Ile Leu His Gly Gly Ser Pro Asp Phe Val Gly Asn Gly Lys His Arg
225                 230                 235                 240
Ala Asn Ser Ser Gly Arg Ser Arg Arg Glu Arg Gln Tyr Ser Val Cys
                245                 250                 255
Asn Ser Glu Asp Ser Pro Gly Ser Cys Glu Ile Leu Tyr Phe Asn Met
            260                 265                 270
Gly Ser Pro Asp Gln Leu Met Val His Lys Gly Lys Cys Ile Gly Ser
            275                 280                 285
Asp Glu Gln Leu Gly Lys Leu Val Tyr Asn Ala Leu Glu Thr Ala Thr
            290                 295                 300
Gly Gly Phe Val Leu Leu Tyr Glu Trp Val Leu Gln Trp Gln Lys Lys
305                 310                 315                 320
Met Gly Pro Phe Leu Thr Ser Gln Glu Lys Glu Lys Ile Asp Lys Cys
                325                 330                 335
Lys Lys Gln Ile Gln Gly Thr Glu Thr Glu Phe Asn Ser Leu Val Lys
            340                 345                 350
Leu Ser His Pro Asn Val Val Arg Tyr Leu Ala Met Asn Leu Lys Glu
            355                 360                 365
Gln Asp Asp Ser Ile Val Val Asp Ile Leu Val Glu His Ile Ser Gly
            370                 375                 380
Val Ser Leu Ala Ala His Leu Ser His Ser Gly Pro Ile Pro Val His
385                 390                 395                 400
Gln Leu Arg Arg Tyr Thr Ala Gln Leu Leu Ser Gly Leu Asp Tyr Leu
                405                 410                 415
His Ser Asn Ser Val Val His Lys Val Leu Ser Ala Ser Asn Val Leu
            420                 425                 430
Val Asp Ala Glu Gly Thr Val Lys Ile Thr Asp Tyr Ser Ile Ser Lys
            435                 440                 445
Arg Leu Ala Asp Ile Cys Lys Glu Asp Val Phe Glu Gln Thr Arg Val
450                 455                 460
Arg Phe Ser Asp Asn Ala Leu Pro Tyr Lys Thr Gly Lys Lys Gly Asp
465                 470                 475                 480
Val Trp Arg Leu Gly Leu Leu Leu Leu Ser Leu Ser Gln Gly Gln Glu
                485                 490                 495
Cys Gly Glu Tyr Pro Val Thr Ile Pro Ser Asp Leu Pro Ala Asp Phe
                500                 505                 510
Gln Asp Phe Leu Lys Lys Cys Val Cys Leu Asp Asp Lys Glu Arg Trp
            515                 520                 525
Ser Pro Gln Gln Leu Leu Lys His Ser Phe Ile Asn Pro Gln Pro Lys
            530                 535                 540
Met Pro Leu Val Glu Gln Ser Pro Glu Asp Ser Gly Gln Asp Tyr
545                 550                 555                 560
Val Glu Thr Val Ile Pro Ser Asn Arg Leu Pro Ser Ala Ala Phe Phe
                565                 570                 575
Ser Glu Thr Gln Arg Gln Phe Ser Arg Tyr Phe Ile Glu Phe Glu Glu
            580                 585                 590
Leu Gln Leu Leu Gly Lys Gly Ala Phe Gly Ala Val Ile Lys Val Gln
            595                 600                 605
```

```
Asn Lys Leu Asp Gly Cys Cys Tyr Ala Val Lys Arg Ile Pro Ile Asn
    610                 615                 620
Pro Ala Ser Arg Gln Phe Arg Arg Ile Lys Gly Glu Val Thr Leu Leu
625                 630                 635                 640
Ser Arg Leu His His Glu Asn Ile Val Arg Tyr Tyr Asn Ala Trp Ile
                645                 650                 655
Glu Arg His Glu Arg Pro Ala Gly Pro Gly Thr Pro Pro Asp Ser
            660                 665                 670
Gly Pro Leu Ala Lys Asp Asp Arg Ala Ala Arg Gly Gln Pro Ala Ser
            675                 680                 685
Asp Thr Asp Gly Leu Asp Ser Val Glu Ala Ala Pro Pro Ile
690                 695                 700
Leu Ser Ser Ser Val Glu Trp Ser Thr Ser Gly Glu Arg Ser Ala Ser
705                 710                 715                 720
Ala Arg Phe Pro Ala Thr Gly Pro Gly Ser Ser Asp Asp Glu Asp Asp
                725                 730                 735
Asp Glu Asp Glu His Gly Gly Val Phe Ser Gln Ser Phe Leu Pro Ala
            740                 745                 750
Ser Asp Ser Glu Ser Asp Ile Ile Phe Asp Asn Glu Asp Glu Asn Ser
        755                 760                 765
Lys Ser Gln Asn Gln Asp Glu Asp Cys Asn Glu Lys Asn Gly Cys His
770                 775                 780
Glu Ser Glu Pro Ser Val Thr Thr Glu Ala Val His Tyr Leu Tyr Ile
785                 790                 795                 800
Gln Met Glu Tyr Cys Glu Lys Ser Thr Leu Arg Asp Thr Ile Asp Gln
                805                 810                 815
Gly Leu Tyr Arg Asp Thr Val Arg Leu Trp Arg Leu Phe Arg Glu Ile
            820                 825                 830
Leu Asp Gly Leu Ala Tyr Ile His Glu Lys Gly Met Ile His Arg Asp
        835                 840                 845
Leu Lys Pro Val Asn Ile Phe Leu Asp Ser Asp His Val Lys Ile
850                 855                 860
Gly Asp Phe Gly Leu Ala Thr Asp His Leu Ala Phe Ser Ala Asp Ser
865                 870                 875                 880
Lys Gln Asp Asp Gln Thr Gly Asp Leu Ile Lys Ser Asp Pro Ser Gly
                885                 890                 895
His Leu Thr Gly Met Val Gly Thr Ala Leu Tyr Val Ser Pro Glu Val
            900                 905                 910
Gln Gly Ser Thr Lys Ser Ala Tyr Asn Gln Lys Val Asp Leu Phe Ser
        915                 920                 925
Leu Gly Ile Ile Phe Phe Glu Met Ser Tyr His Pro Met Val Thr Ala
    930                 935                 940
Ser Glu Arg Ile Phe Val Leu Asn Gln Leu Arg Asp Pro Thr Ser Pro
945                 950                 955                 960
Lys Phe Pro Glu Asp Phe Asp Asp Gly Glu His Ala Lys Gln Lys Ser
                965                 970                 975
Val Ile Ser Trp Leu Leu Asn His Asp Pro Ala Lys Arg Pro Thr Ala
            980                 985                 990
Thr Glu Leu Leu Lys Ser Glu Leu Pro Pro Pro Gln Met Glu Glu
        995                 1000                1005
Ser Glu Leu His Glu Val Leu His His Thr Leu Thr Asn Val Asp Gly
    1010                1015                1020
```

```
Lys Ala Tyr Arg Thr Met Met Ala Gln Ile Phe Ser Gln Arg Ile Ser
1025                1030                1035                1040

Pro Ala Ile Asp Tyr Thr Tyr Asp Ser Asp Ile Leu Lys Gly Asn Phe
            1045                1050                1055

Ser Ile Arg Thr Ala Lys Met Gln Gln His Val Cys Glu Thr Ile Ile
        1060                1065                1070

Arg Ile Phe Lys Arg His Gly Ala Val Gln Leu Cys Thr Pro Leu Leu
    1075                1080                1085

Leu Pro Arg Asn Arg Gln Ile Tyr Glu His Asn Glu Ala Ala Leu Phe
1090                1095                1100

Met Asp His Ser Gly Met Leu Val Met Leu Pro Phe Asp Leu Arg Ile
1105                1110                1115                1120

Pro Phe Ala Arg Tyr Val Ala Arg Asn Asn Ile Leu Asn Leu Lys Arg
            1125                1130                1135

Tyr Cys Ile Glu Arg Val Phe Arg Pro Arg Lys Leu Asp Arg Phe His
            1140                1145                1150

Pro Lys Glu Leu Leu Glu Cys Ala Phe Asp Ile Val Thr Ser Thr Thr
        1155                1160                1165

Asn Ser Phe Leu Pro Thr Ala Glu Ile Ile Tyr Thr Ile Tyr Glu Ile
    1170                1175                1180

Ile Gln Glu Phe Pro Ala Leu Gln Glu Arg Asn Tyr Ser Ile Tyr Leu
1185                1190                1195                1200

Asn His Thr Met Leu Leu Lys Ala Ile Leu Leu His Cys Gly Ile Pro
            1205                1210                1215

Glu Asp Lys Leu Ser Gln Val Tyr Ile Ile Leu Tyr Asp Ala Val Thr
            1220                1225                1230

Glu Lys Leu Thr Arg Arg Glu Val Glu Ala Lys Phe Cys Asn Leu Ser
        1235                1240                1245

Leu Ser Ser Asn Ser Leu Cys Arg Leu Tyr Lys Phe Ile Glu Gln Lys
    1250                1255                1260

Gly Asp Leu Gln Asp Leu Met Pro Thr Ile Asn Ser Leu Ile Lys Gln
1265                1270                1275                1280

Lys Thr Gly Ile Ala Gln Leu Val Lys Tyr Gly Leu Lys Asp Leu Glu
            1285                1290                1295

Glu Val Val Gly Leu Leu Lys Lys Leu Gly Ile Lys Leu Gln Val Leu
            1300                1305                1310

Ile Asn Leu Gly Leu Val Tyr Lys Val Gln Gln His Asn Gly Ile Ile
        1315                1320                1325

Phe Gln Phe Val Ala Phe Ile Lys Arg Arg Gln Arg Ala Val Pro Glu
    1330                1335                1340

Ile Leu Ala Ala Gly Gly Arg Tyr Asp Leu Leu Ile Pro Gln Phe Arg
1345                1350                1355                1360

Gly Pro Gln Ala Leu Gly Pro Val Pro Thr Ala Ile Gly Val Ser Ile
            1365                1370                1375

Ala Ile Asp Lys Ile Ser Ala Ala Val Leu Asn Met Glu Glu Ser Val
            1380                1385                1390

Thr Ile Ser Ser Cys Asp Leu Leu Val Ser Val Gly Gln Met Ser
        1395                1400                1405

Met Ser Arg Ala Ile Asn Leu Thr Gln Lys Leu Trp Thr Ala Gly Ile
    1410                1415                1420

Thr Ala Glu Ile Met Tyr Asp Trp Ser Gln Ser Gln Glu Glu Leu Gln
1425                1430                1435                1440

Glu Tyr Cys Arg His His Glu Ile Thr Tyr Val Ala Leu Val Ser Asp
```

-continued

```
                        1445                1450                1455
Lys Glu Gly Ser His Val Lys Val Lys Ser Phe Glu Lys Arg Gln
            1460                1465                1470
Thr Glu Lys Arg Val Leu Glu Thr Glu Leu Val Asp His Val Leu Gln
        1475                1480                1485
Lys Leu Arg Thr Lys Val Thr Asp Glu Arg Asn Gly Arg Glu Ala Ser
    1490                1495                1500
Asp Asn Leu Ala Val Gln Asn Leu Lys Gly Ser Phe Ser Asn Ala Ser
1505                1510                1515                1520
Gly Leu Phe Glu Ile His Gly Ala Thr Val Val Pro Ile Val Ser Val
            1525                1530                1535
Leu Ala Pro Glu Lys Leu Ser Ala Ser Thr Arg Arg Arg Tyr Glu Thr
        1540                1545                1550
Gln Val Gln Thr Arg Leu Gln Thr Ser Leu Ala Asn Leu His Gln Lys
        1555                1560                1565
Ser Ser Glu Ile Glu Ile Leu Ala Val Asp Leu Pro Lys Glu Thr Ile
    1570                1575                1580
Leu Gln Phe Leu Ser Leu Glu Trp Asp Ala Asp Glu Gln Ala Phe Asn
1585                1590                1595                1600
Thr Thr Val Lys Gln Leu Leu Ser Arg Leu Pro Lys Gln Arg Tyr Leu
            1605                1610                1615
Lys Leu Val Cys Asp Glu Ile Tyr Asn Ile Lys Val Glu Lys Lys Val
            1620                1625                1630
Ser Val Leu Phe Leu Tyr Ser Tyr Arg Asp Asp Tyr Tyr Arg Ile Leu
        1635                1640                1645
Phe
```

<210> SEQ ID NO 3
<211> LENGTH: 4950
<212> TYPE: DNA
<213> ORGANISM: Homo sapiens

<400> SEQUENCE: 3

| | | |
|---|---|---|
| atggctgggg gccgtggggc ccccgggcgc ggccgggacg agcctccgga gagctacccg | 60 |
| caacgacagg accacgagct acaggccctg gaggccatct acggcgcgga cttccaagac | 120 |
| ctgcggccgg acgcttgcgg accggtcaaa gagcccctg aaatcaattt agttttgtac | 180 |
| cctcaaggcc taactggtga agaagtatat gtaaaagtgg atttgagggt taaatgccca | 240 |
| cctacctatc cagatgtagt tcctgaaata gagttaaaaa atgccaaagg tctatcaaat | 300 |
| gaaagtgtca atttgttaaa atctcgccta gaagaactgg ccaagaaaca ctgtggggag | 360 |
| gtgatgatct tgaactggc ttaccacgtg cagtcatttc tcagcgagca taacaagccc | 420 |
| cctcccaagt cttttcatga gaaatgctg gaaggcggg ctcaggagga gcagcagagg | 480 |
| ctgttggagg ccaagcggaa agaagagcag gagcaacgtg aaatcctgca tgagattcag | 540 |
| agaaggaaag aagagataaa gaagagaaa aaaggaaag aaatggctaa gcaggaacgt | 600 |
| ttggaaattg ctagtttgtc aaaccaagat catacctcta gaaggaccc aggaggacac | 660 |
| agaacggctg ccattctaca tggaggctct cctgactttg taggaaatgg taaacatcgg | 720 |
| gcaaactcct caggaaggtc taggcgagaa cgtcagtatt ctgtatgtaa tagtgaagat | 780 |
| tctcctggct cttgtgaaat tctgtatttc aatatgggga gtcctgatca gctcatggtg | 840 |
| cacaaaggga atgtattgg cagtgatgaa caacttggaa attagtcta caatgctttg | 900 |
| gaaacagcca ctggtggctt tgtcttgttg tatgagtggg tccttcagtg gcagaaaaaa | 960 |

```
atgggtccat tccttaccag tcaagaaaaa gagaagattg ataagtgcaa aaagcagatt    1020
caaggaacag aaacagaatt caactcactg gtaaaattga gccatccaaa tgtagtacgc    1080
taccttgcaa tgaatctcaa agagcaagac gactccatcg tggtggacat tttagtggag    1140
cacattagtg gggtctctct tgctgcacac ctgagccact caggccccat ccctgtgcat    1200
cagcttcgca ggtacacagc tcagctcctg tcaggccttg attatctgca cagcaattct    1260
gtggtgcata aggtcctgag tgcatctaat gtcttggtgg atgcagaagg caccgtcaag    1320
attacggact atagcatttc taagcgcctc gcagacattt gcaaggagga tgtgtttgag    1380
caaacccgag ttcgttttag tgacaatgct ctgccttata aaacggggaa gaaaggagat    1440
gtttggcgtc ttggccttct gctgctgtcc ctcagccaag gacaggaatg tggagagtac    1500
cctgtgacca tccctagtga cttaccagct gactttcaag attttctaaa gaaatgtgtg    1560
tgcttggatg acaaggaaag atggagtccc cagcagttgt tgaaacacag ctttataaat    1620
ccccagccaa aaatgcctct agtggaacaa agtcctgaag attctggagg acaagattat    1680
gttgagactt ttattcctag caaccggcta cccagtgctg ccttctttag tgagacacag    1740
agacagtttt cccgatactt cattgagttt gaagaattac aacttcttgg taaaggagct    1800 tttgagctg tcatcaaggt gcagaacaag ttggacggct gctgctacgc agtgaagcgc    1860
atccccatca acccggccag ccggcagttc cgcaggatca agggcgaagt gacactgctg    1920
tcacggctgc accatgagaa cattgtgcgc tactacaacg cctggatcga gcggcacgag    1980
cggccggcgg gaccggggac gccgcccccg gactccgggc ccctggccaa ggatgaccga    2040
gctgcacgcg ggcagccggc gagcgacaca gacggcctgg acagcgtaga ggccgccgcg    2100
ccgccaccca tcctcagcag ctcggtggag tggagcactt cgggcgagcg ctcggccagt    2160
gcccgtttcc ccgccaccgg cccgggctcc agcgatgacg aggacgacga cgaggacgag    2220
cacggtggcg tcttctccca gtccttcctg cctgcttcag attctgaaag tgatattatc    2280
tttgacaatg aagatgagaa cagtaaaagt cagaatcagg atgaagattg caatgaaaag    2340
aatggctgcc atgaaagtga gccatcagtg acgactgagc tgtgcacta cctatacatc    2400 cagatggagt actgtgagaa gagcacttta cgagacacca ttgaccaggg actgtatcga    2460
gacaccgtca gactctggag gcttttttcga gagattctgg atggattagc ttatatccat    2520
gagaaaggaa tgattcaccg ggatttgaag cctgtcaaca ttttttttgga ttctgatgac    2580 catgtgaaaa taggtgattt tggtttggcg acagaccatc tagccttttc tgctgacagc    2640
aaacaagacg atcagacagg agacttgatt aagtcagacc cttcaggtca cttaactggg    2700
atggttggca ctgctctcta tgtaagccca gaggtccaag gaagcaccaa atctgcatac    2760
aaccagaaag tggatctctt cagcctggga attatcttct ttgagatgtc ctatcacccc    2820
atggtcacgg cttcagaaag gatctttgtt ctcaaccaac tcagagatcc cacttcgcct    2880
aagtttccag aagactttga cgatggagag catgcaaagc agaaatcagt catctcctgg    2940
ctgttgaacc acgatccagc aaaacggccc acagccacag aactgctcaa gagtgagctg    3000
ctgcccccac cccagatgga ggagtcagag ctgcatgaag tgctgcacca cacgctgacc    3060
aacgtggatg ggaaggccta ccgcaccatg atggcccaga tcttctcgca gcgcatctcc    3120
cctgccatcg attacaccta tgacagcgac atactgaagg gcaacttctc aatccgtaca    3180
gccaagatgc agcagcatgt gtgtgaaacc atcatccgca tctttaaaag acatggagct    3240
gttcagttgt gtactccact actgcttccc cgaaacagac aaatatatga gcacaacgaa    3300
```

-continued

```
gctgccctat tcatggacca cagcgggatg ctggtgatgc ttccttttga cctgcggatc      3360
ccttttgcaa gatatgtggc aagaaataat atattgaatt taaaacgata ctgcatagaa      3420
cgtgtgttca ggccgcgcaa gttagatcga tttcatccca aagaacttct ggagtgtgca      3480
tttgatattg tcacttctac caccaacagc tttctgccca ctgctgaaat tatctacact      3540
atctatgaaa tcatccaaga gtttccagca cttcaggaaa gaattacag tatttatttg       3600 aaccatacca tgttattgaa agcaatactc ttacactgtg ggatcccaga agataaactc      3660
agtcaagtct acattattct gtatgatgct gtgacagaga agctgacgag gagagaagtg      3720
gaagctaaat tttgtaatct gtctttgtct tctaatagtc tgtgtcgact ctacaagttt      3780
attgaacaga agggagattt gcaagatctt atgccaacaa taaattcatt aataaaacag      3840
aaaacaggta ttgcacagtt ggtgaagtat ggcttaaaag acctagagga ggttgttgga      3900
ctgttgaaga aactcggcat caagttacag gtcttgatca atttgggctt ggtttacaag      3960
gtgcagcagc acaatggaat catcttccag tttgtggctt tcatcaaacg aaggcaaagg      4020
gctgtacctg aaatcctcgc agctggaggc agatatgacc tgctgattcc ccagtttaga      4080
gggccacaag ctctggggcc agttcccact gccattgggg tcagcatagc tatagacaag      4140
atatctgctg ctgtcctcaa catggaggaa tctgttacaa taagctcttg tgacctcctg      4200
gttgtaagtg ttggtcagat gtctatgtcc agggccatca acctaaccca gaaactctgg      4260
acagcaggca tcacagcaga aatcatgtac gactggtcac agtcccaaga ggaattacaa      4320
gagtactgca gacatcatga aatcacctat gtggcccttg tctcggataa agaaggaagc      4380
catgtcaagg ttaagtcttt cgagaaggaa aggcagacag agaagcgtgt gctggagact      4440
gaacttgtgg accatgtact gcagaaactg aggactaaag tcactgatga aggaatggc       4500 agagaagctt ccgataatct tgcagtgcaa aatctgaagg ggtcattttc taatgcttca      4560
ggtttgtttg aaatccatgg agcaacagtg gttcccattg tgagtgtgct agccccggag      4620
aagctgtcag ccagcactag gaggcgctat gaaactcagg tacaaactcg acttcagacc      4680
tcccttgcca acttacatca gaaaagcagt gaaattgaaa ttctggctgt ggatctaccc      4740
aaagaaacaa tattacagtt tttatcatta gagtgggatg ctgatgaaca ggcatttaac      4800
acaactgtga agcagctgct gtcacgcctg ccaaagcaaa gatacctcaa attagtctgt      4860
gatgaaattt ataacatcaa agtagaaaaa aaggtgtctg tgctatttct gtacagctat      4920
agagatgact actacagaat cttatttaa                                        4950
```

<210> SEQ ID NO 4
<211> LENGTH: 1648
<212> TYPE: PRT
<213> ORGANISM: Homo sapiens

<400> SEQUENCE: 4

```
Met Ala Gly Gly Arg Gly Ala Pro Gly Arg Gly Arg Asp Glu Pro Pro
 1               5                  10                  15

Glu Ser Tyr Pro Gln Arg Gln Asp His Glu Leu Gln Ala Leu Glu Ala
             20                  25                  30

Ile Tyr Gly Ala Asp Phe Gln Asp Leu Arg Pro Asp Ala Cys Gly Pro
         35                  40                  45

Val Lys Glu Pro Pro Glu Ile Asn Leu Val Leu Tyr Pro Gln Gly Leu
     50                  55                  60

Thr Gly Glu Glu Val Tyr Val Lys Val Asp Leu Arg Val Lys Cys Pro
 65                  70                  75                  80
```

```
Pro Thr Tyr Pro Asp Val Val Pro Glu Ile Glu Leu Lys Asn Ala Lys
                85                  90                  95
Gly Leu Ser Asn Glu Ser Val Asn Leu Leu Lys Ser Arg Leu Glu Glu
                100                 105                 110
Leu Ala Lys Lys His Cys Gly Glu Val Met Ile Phe Glu Leu Ala Tyr
                115                 120                 125
His Val Gln Ser Phe Leu Ser Glu His Asn Lys Pro Pro Lys Ser
    130                 135                 140
Phe His Glu Glu Met Leu Glu Arg Arg Ala Gln Glu Glu Gln Arg
145                 150                 155                 160
Leu Leu Glu Ala Arg Arg Lys Glu Glu Gln Glu Arg Glu Ile Leu
                165                 170                 175
His Glu Ile Gln Arg Arg Lys Glu Glu Ile Lys Glu Glu Lys Lys Arg
                180                 185                 190
Lys Glu Met Ala Lys Gln Glu Arg Leu Glu Ile Thr Ser Leu Ser Asn
                195                 200                 205
Gln Asp His Thr Ser Lys Lys Asp Pro Gly Gly His Arg Thr Ala Ala
                210                 215                 220
Ile Leu His Gly Gly Ser Pro Asp Phe Val Gly Asn Gly Lys His Arg
225                 230                 235                 240
Ala Asn Ser Ser Gly Arg Ser Arg Arg Glu Arg Gln Tyr Ser Val Cys
                245                 250                 255
Asn Ser Glu Asp Ser Pro Gly Ser Cys Glu Ile Leu Tyr Phe Asn Met
                260                 265                 270
Gly Ser Pro Asp Gln Leu Met Val His Lys Gly Arg Cys Ile Gly Ser
                275                 280                 285
Asp Glu Gln Leu Gly Lys Leu Val Tyr Asn Ala Leu Glu Thr Ala Thr
                290                 295                 300
Gly Gly Phe Val Leu Leu Tyr Glu Trp Val Leu Gln Trp Lys Met
305                 310                 315                 320
Gly Pro Phe Leu Thr Ser Gln Glu Lys Glu Lys Ile Asp Lys Cys Lys
                325                 330                 335
Lys Gln Ile Gln Gly Tyr Glu Thr Glu Phe Asn Ser Leu Val Lys Leu
                340                 345                 350
Ser His Pro Asn Val Val Arg Tyr Leu Ala Met Asn Leu Lys Glu Gln
                355                 360                 365
Asp Asp Ser Ile Val Val Asp Ile Leu Val Glu His Ile Ser Gly Val
                370                 375                 380
Ser Leu Ala Ala His Leu Ser His Ser Gly Pro Ile Pro Val His Gln
385                 390                 395                 400
Leu Arg Arg Tyr Thr Ala Gln Leu Leu Ser Gly Leu Asp Tyr Leu His
                405                 410                 415
Ser Asn Ser Val Val His Lys Val Leu Ser Ala Ser Asn Val Leu Val
                420                 425                 430
Asp Ala Glu Gly Thr Val Lys Ile Thr Asp Tyr Ser Ile Ser Lys Arg
                435                 440                 445
Leu Ala Asp Ile Cys Lys Glu Asp Val Phe Glu Gln Thr Arg Val Arg
                450                 455                 460
Phe Ser Asp Asn Ala Leu Pro Tyr Lys Thr Gly Lys Lys Gly Asp Val
465                 470                 475                 480
Trp Arg Leu Gly Leu Leu Leu Ser Leu Ser Gln Gly Gln Glu Cys
                485                 490                 495
Gly Glu Tyr Pro Val Thr Ile Pro Ser Asp Leu Pro Ala Asp Phe Gln
```

-continued

```
                500             505             510
Asp Phe Leu Lys Lys Cys Val Cys Leu Asp Asp Lys Glu Arg Trp Ser
            515                 520                 525
Pro Gln Gln Leu Leu Lys His Ser Phe Ile Asn Pro Gln Pro Lys Met
        530                 535                 540
Pro Leu Val Glu Gln Ser Pro Glu Asp Ser Gly Gly Gln Asp Tyr Val
545                 550                 555                 560
Glu Thr Val Ile Pro Ser Asn Arg Leu Pro Ser Ala Ala Phe Phe Ser
                565                 570                 575
Glu Thr Gln Arg Gln Phe Ser Arg Tyr Phe Ile Glu Phe Glu Glu Leu
            580                 585                 590
Gln Leu Leu Gly Lys Gly Ala Phe Gly Ala Val Ile Lys Val Gln Asn
        595                 600                 605
Lys Leu Asp Gly Cys Cys Tyr Ala Val Lys Arg Ile Pro Ile Asn Pro
    610                 615                 620
Ala Ser Arg Gln Phe Arg Arg Ile Lys Gly Glu Val Thr Leu Leu Ser
625                 630                 635                 640
Arg Leu His His Glu Asn Ile Val Arg Tyr Tyr Asn Ala Trp Ile Glu
                645                 650                 655
Arg His Glu Arg Pro Ala Gly Pro Gly Thr Pro Pro Asp Ser Gly
            660                 665                 670
Pro Leu Ala Lys Asp Asp Arg Ala Ala Arg Gly Gln Pro Ala Ser Asp
        675                 680                 685
Thr Asp Gly Leu Asp Ser Val Glu Ala Ala Pro Pro Ile Leu
    690                 695                 700
Ser Ser Ser Val Glu Trp Ser Thr Ser Gly Glu Arg Ser Ala Ser Ala
705                 710                 715                 720
Arg Phe Pro Ala Thr Gly Pro Gly Ser Ser Asp Asp Glu Asp Asp Glu
                725                 730                 735
Asp Glu His Gly Gly Val Phe Ser Gln Ser Phe Leu Pro Ala Ser Asp
            740                 745                 750
Ser Glu Ser Asp Ile Ile Phe Asp Asn Glu Asp Glu Asn Ser Lys Ser
        755                 760                 765
Gln Asn Gln Asp Glu Asp Cys Asn Glu Lys Asn Gly Cys His Glu Ser
    770                 775                 780
Glu Pro Ser Val Thr Thr Glu Ala Val His Tyr Leu Tyr Ile Gln Met
785                 790                 795                 800
Glu Tyr Cys Glu Lys Ser Thr Leu Arg Asp Thr Ile Asp Gln Gly Leu
                805                 810                 815
Tyr Arg Asp Thr Val Arg Leu Trp Arg Leu Phe Arg Glu Ile Leu Asp
            820                 825                 830
Gly Leu Ala Tyr Ile His Glu Lys Gly Met Ile His Arg Asp Leu Lys
        835                 840                 845
Pro Val Asn Ile Phe Leu Asp Ser Asp His Val Lys Ile Gly Asp
    850                 855                 860
Phe Gly Leu Ala Thr Asp His Leu Ala Phe Ser Ala Asp Ser Lys Gln
865                 870                 875                 880
Asp Asp Gln Thr Gly Asp Gly Leu Ile Lys Ser Asp Pro Ser Gly His
                885                 890                 895
Leu Thr Gly Met Val Gly Thr Ala Leu Tyr Val Ser Pro Glu Val Gln
            900                 905                 910
Gly Ser Thr Lys Ser Ala Tyr Asn Gln Lys Val Asp Leu Phe Ser Leu
        915                 920                 925
```

-continued

```
Gly Ile Ile Phe Phe Glu Met Ser Tyr His Pro Met Val Thr Ala Ser
    930                 935                 940
Glu Arg Ile Phe Val Leu Asn Gln Leu Arg Asp Pro Thr Ser Pro Lys
945                 950                 955                 960
Phe Pro Glu Asp Phe Asp Gly Glu His Ala Lys Gln Lys Ser Val
                965                 970                 975
Ile Ser Trp Leu Leu Asn His Asp Pro Ala Lys Arg Pro Thr Ala Thr
                980                 985                 990
Glu Leu Leu Lys Ser Glu Leu Leu Pro Pro Gln Met Glu Glu Ser
                995                 1000                1005
Glu Leu His Glu Val Leu His His Thr Leu Thr Asn Val Asp Gly Lys
    1010                1015                1020
Ala Tyr Arg Thr Met Met Ala Gln Ile Phe Ser Gln Arg Ile Ser Pro
1025                1030                1035                1040
Ala Ile Asp Tyr Thr Tyr Asp Ser Asp Ile Leu Lys Gly Asn Phe Ser
                1045                1050                1055
Ile Arg Thr Ala Lys Met Gln Gln His Val Cys Glu Thr Ile Ile Arg
                1060                1065                1070
Ile Phe Lys Arg His Gly Ala Val Gln Leu Cys Thr Pro Leu Leu Leu
                1075                1080                1085
Pro Arg Asn Arg Gln Ile Tyr Glu His Asn Glu Ala Ala Leu Phe Met
    1090                1095                1100
Asp His Ser Gly Met Leu Val Met Leu Pro Phe Asp Leu Arg Ile Pro
1105                1110                1115                1120
Phe Ala Arg Tyr Val Ala Arg Asn Asn Ile Leu Asn Leu Lys Arg Tyr
                1125                1130                1135
Cys Ile Glu Arg Val Phe Arg Pro Arg Lys Leu Asp Arg Phe His Pro
                1140                1145                1150
Lys Glu Leu Leu Glu Cys Ala Phe Asp Ile Val Thr Ser Thr Thr Asn
    1155                1160                1165
Ser Phe Leu Pro Thr Ala Glu Ile Ile Tyr Thr Ile Tyr Glu Ile Ile
    1170                1175                1180
Gln Glu Phe Pro Ala Leu Gln Glu Arg Asn Tyr Ser Ile Tyr Leu Asn
1185                1190                1195                1200
His Thr Met Leu Leu Lys Ala Ile Leu Leu His Cys Gly Ile Pro Glu
                1205                1210                1215
Asp Lys Leu Ser Gln Val Tyr Ile Ile Leu Tyr Asp Ala Val Thr Glu
                1220                1225                1230
Lys Leu Thr Arg Arg Glu Val Glu Ala Lys Phe Cys Asn Leu Ser Leu
                1235                1240                1245
Ser Ser Asn Ser Leu Cys Arg Leu Tyr Lys Phe Ile Glu Gln Lys Gly
    1250                1255                1260
Asp Leu Gln Asp Leu Met Pro Thr Ile Asn Ser Leu Ile Lys Gln Lys
1265                1270                1275                1280
Thr Gly Ile Ala Gln Leu Val Lys Tyr Ser Leu Lys Asp Leu Glu Asp
                1285                1290                1295
Val Val Gly Leu Leu Lys Lys Leu Gly Ile Lys Leu Gln Val Leu Ile
                1300                1305                1310
Asn Leu Gly Leu Val Tyr Lys Val Gln Gln His Asn Gly Ile Ile Phe
    1315                1320                1325
Gln Phe Val Ala Phe Ile Lys Arg Arg Gln Arg Ala Val Pro Glu Ile
    1330                1335                1340
```

```
Leu Ala Ala Gly Gly Arg Tyr Asp Leu Leu Ile Pro Gln Phe Arg Gly
1345                1350                1355                1360

Pro Gln Ala Leu Gly Pro Val Pro Thr Ala Ile Gly Val Ser Ile Ala
                1365                1370                1375

Ile Asp Lys Ile Ser Ala Ala Val Leu Asn Met Glu Glu Ser Val Thr
            1380                1385                1390

Ile Ser Ser Cys Asp Leu Leu Val Ser Val Gly Gln Met Ser Met
        1395                1400                1405

Ser Arg Ala Ile Asn Leu Thr Gln Lys Leu Trp Thr Ala Gly Ile Thr
    1410                1415                1420

Ala Glu Ile Met Tyr Asp Trp Ser Gln Ser Gln Glu Leu Gln Glu
1425                1430                1435                1440

Tyr Cys Arg His His Glu Ile Thr Tyr Val Ala Leu Val Ser Asp Lys
                1445                1450                1455

Glu Gly Ser His Val Lys Val Lys Ser Phe Glu Lys Glu Arg Gln Thr
                1460                1465                1470

Glu Lys Arg Val Leu Glu Thr Glu Leu Val Asp His Val Leu Gln Lys
        1475                1480                1485

Leu Arg Thr Lys Val Thr Asp Glu Arg Asn Gly Arg Glu Ala Ser Asp
    1490                1495                1500

Asn Leu Ala Val Gln Asn Leu Lys Gly Ser Phe Ser Asn Ala Ser Gly
1505                1510                1515                1520

Leu Phe Glu Ile His Gly Ala Thr Val Val Pro Ile Ser Val Leu
            1525                1530                1535

Ala Pro Glu Lys Leu Ser Ala Ser Thr Arg Arg Tyr Glu Ile Gln
            1540                1545                1550

Val Gln Thr Arg Leu Gln Thr Ser Leu Ala Asn Leu His Gln Lys Ser
        1555                1560                1565

Ser Glu Ile Glu Ile Leu Ala Val Asp Leu Pro Lys Glu Thr Ile Leu
    1570                1575                1580

Gln Phe Leu Ser Leu Glu Trp Asp Ala Asp Glu Gln Ala Phe Asn Thr
1585                1590                1595                1600

Thr Val Lys Gln Leu Leu Ser Arg Leu Pro Lys Gln Arg Tyr Leu Lys
                1605                1610                1615

Leu Val Cys Asp Glu Ile Tyr Asn Ile Lys Val Glu Lys Lys Val Ser
            1620                1625                1630

Val Leu Phe Leu Tyr Ser Tyr Arg Asp Asp Tyr Tyr Arg Ile Leu Phe
        1635                1640                1645

<210> SEQ ID NO 5
<211> LENGTH: 1648
<212> TYPE: PRT
<213> ORGANISM: Mouse

<400> SEQUENCE: 5

Met Ala Gly Gly Gly Ala Ser Gly Gly Arg Ala Glu Pro Gln
1               5                   10                  15

Glu Ser Tyr Ser Gln Arg Gln Asp His Glu Leu Gln Ala Leu Glu Ala
            20                  25                  30

Ile Tyr Gly Ser Asp Phe Gln Asp Leu Arg Pro Asp Ala Arg Gly Arg
        35                  40                  45

Val Arg Glu Pro Pro Glu Ile Asn Leu Val Leu Tyr Pro Gln Gly Leu
    50                  55                  60

Ala Gly Glu Glu Val Tyr Val Gln Val Glu Leu Gln Val Lys Cys Pro
65                  70                  75                  80
```

-continued

```
Pro Thr Tyr Pro Asp Val Val Pro Glu Ile Glu Leu Lys Asn Ala Lys
            85                  90                  95
Gly Leu Ser Asn Glu Ser Val Asn Leu Leu Lys Ser His Leu Glu Glu
            100                 105                 110
Leu Ala Lys Lys Gln Cys Gly Glu Val Met Ile Phe Glu Leu Ala His
            115                 120                 125
His Val Gln Ser Phe Leu Ser Glu His Asn Lys Pro Pro Pro Lys Ser
            130                 135                 140
Phe His Glu Glu Met Leu Glu Arg Gln Ala Gln Glu Lys Gln Gln Arg
145                 150                 155                 160
Leu Leu Glu Ala Arg Arg Lys Glu Glu Gln Glu Gln Arg Glu Ile Leu
                    165                 170                 175
His Glu Ile Gln Arg Arg Lys Glu Glu Ile Lys Glu Glu Lys Lys Arg
                    180                 185                 190
Lys Glu Met Ala Lys Gln Glu Arg Leu Glu Ile Thr Ser Leu Thr Asn
                195                 200                 205
Gln Asp Tyr Ala Ser Lys Arg Asp Pro Ala Gly His Arg Ala Ala Ala
            210                 215                 220
Ile Leu His Gly Gly Ser Pro Asp Phe Val Gly Asn Gly Lys Ala Arg
225                 230                 235                 240
Thr Tyr Ser Ser Gly Arg Ser Arg Arg Glu Arg Gln Tyr Ser Val Cys
                    245                 250                 255
Ser Gly Glu Pro Ser Pro Gly Ser Cys Asp Ile Leu His Phe Ser Val
                260                 265                 270
Gly Ser Pro Asp Gln Leu Met Val His Lys Gly Arg Cys Val Gly Ser
            275                 280                 285
Asp Glu Gln Leu Gly Lys Val Val Tyr Asn Ala Leu Glu Thr Ala Thr
            290                 295                 300
Gly Ser Phe Val Leu Leu His Glu Trp Val Leu Gln Trp Gln Lys Met
305                 310                 315                 320
Gly Pro Cys Leu Thr Ser Gln Glu Lys Glu Lys Ile Asp Lys Cys Lys
                    325                 330                 335
Arg Gln Ile Gln Gly Ala Glu Thr Glu Phe Ser Ser Leu Val Lys Leu
                    340                 345                 350
Ser His Pro Asn Ile Val Arg Tyr Phe Ala Met Asn Ser Arg Glu Glu
                355                 360                 365
Glu Asp Ser Ile Val Ile Asp Ile Leu Ala Glu His Val Ser Gly Ile
            370                 375                 380
Ser Leu Ala Thr His Leu Ser His Ser Gly Pro Val Pro Ala His Gln
385                 390                 395                 400
Leu Arg Lys Tyr Thr Ala Gln Leu Leu Ala Gly Leu Asp Tyr Leu His
                    405                 410                 415
Ser Asn Ser Val Val His Lys Val Leu Ser Ala Ser Ser Val Leu Val
                420                 425                 430
Asp Ala Glu Gly Thr Val Lys Ile Thr Asp Tyr Ser Ile Ser Lys Arg
            435                 440                 445
Leu Ala Asp Ile Cys Lys Glu Asp Val Phe Glu Gln Ala Arg Val Arg
450                 455                 460
Phe Ser Asp Ser Ala Leu Pro Tyr Lys Thr Gly Lys Lys Gly Asp Val
465                 470                 475                 480
Trp Arg Leu Gly Leu Leu Leu Leu Ser Leu Ser Gln Gly Gln Glu Cys
                    485                 490                 495
```

-continued

```
Gly Glu Tyr Pro Val Thr Ile Pro Ser Asp Leu Pro Ala Asp Phe Gln
            500                 505                 510

Asp Phe Leu Lys Lys Cys Val Cys Leu Asp Asp Lys Glu Arg Trp Ser
            515                 520                 525

Pro Gln Gln Leu Leu Lys His Ser Phe Ile Asn Pro Gln Pro Lys Leu
            530                 535                 540

Pro Leu Val Glu Gln Ser Pro Glu Asp Ser Gly Gly Gln Asp Tyr Ile
545                 550                 555                 560

Glu Thr Val Ile Pro Ser Asn Gln Leu Pro Ser Ala Ala Phe Phe Ser
                565                 570                 575

Glu Thr Gln Lys Gln Phe Ser Arg Tyr Phe Ile Glu Phe Glu Glu Leu
            580                 585                 590

Gln Leu Leu Gly Lys Gly Ala Phe Gly Ala Val Ile Lys Val Gln Asn
            595                 600                 605

Lys Leu Asp Gly Cys Cys Tyr Ala Val Lys Arg Ile Pro Ile Asn Pro
            610                 615                 620

Ala Ser Arg His Phe Arg Arg Ile Lys Gly Glu Val Thr Leu Leu Ser
625                 630                 635                 640

Arg Leu His His Glu Asn Ile Val Arg Tyr Tyr Asn Ala Trp Ile Glu
                645                 650                 655

Arg His Glu Arg Pro Ala Val Pro Gly Thr Pro Pro Asp Cys Thr
            660                 665                 670

Pro Gln Ala Gln Asp Ser Pro Ala Thr Cys Gly Lys Thr Ser Gly Asp
            675                 680                 685

Thr Glu Glu Leu Gly Ser Val Glu Ala Ala Pro Pro Ile Leu
            690                 695                 700

Ser Ser Ser Val Glu Trp Ser Thr Ser Ala Glu Arg Ser Thr Ser Thr
705                 710                 715                 720

Arg Phe Pro Val Thr Gly Gln Asp Ser Ser Asp Glu Glu Asp Glu
                725                 730                 735

Asp Glu Arg Asp Gly Val Phe Ser Gln Ser Phe Leu Pro Ala Ser Asp
            740                 745                 750

Ser Asp Ser Asp Ile Ile Phe Asp Asn Glu Asp Glu Asn Ser Lys Ser
            755                 760                 765

Gln Asn Gln Asp Glu Asp Cys Asn Gln Lys Asp Gly Ser His Glu Ile
            770                 775                 780

Glu Pro Ser Val Thr Ala Glu Ala Val His Tyr Leu Tyr Ile Gln Met
785                 790                 795                 800

Glu Tyr Cys Glu Lys Ser Thr Leu Arg Asp Thr Ile Asp Gln Gly Leu
            805                 810                 815

Phe Arg Asp Thr Ser Arg Leu Trp Arg Leu Phe Arg Glu Ile Leu Asp
            820                 825                 830

Gly Leu Ala Tyr Ile His Glu Lys Gly Met Ile His Arg Asp Leu Lys
            835                 840                 845

Pro Val Asn Ile Phe Leu Asp Ser Asp His Val Lys Ile Gly Asp
            850                 855                 860

Phe Gly Leu Ala Thr Asp His Leu Ala Phe Thr Ala Glu Gly Lys Gln
865                 870                 875                 880

Asp Asp Gln Ala Gly Asp Gly Val Ile Lys Ser Asp Pro Ser Gly His
                885                 890                 895

Leu Thr Gly Met Val Gly Thr Ala Leu Tyr Val Ser Pro Glu Val Gln
            900                 905                 910

Gly Ser Thr Lys Ser Ala Tyr Asn Gln Lys Val Asp Leu Phe Ser Leu
```

-continued

```
            915                 920                 925
Gly Ile Ile Phe Phe Glu Met Ser Tyr His Pro Met Val Thr Ala Ser
        930                 935                 940
Glu Arg Ile Phe Val Leu Asn Gln Leu Arg Asp Pro Thr Ser Pro Lys
945                 950                 955                 960
Phe Pro Asp Asp Phe Asp Asp Gly Glu His Thr Lys Gln Lys Ser Val
                965                 970                 975
Ile Ser Trp Leu Leu Asn His Asp Pro Ala Lys Arg Pro Thr Ala Met
            980                 985                 990
Glu Leu Leu Lys Ser Glu Leu Leu Pro Pro Gln Met Glu Glu Ser
        995                 1000                1005
Glu Leu His Glu Val Leu His His Thr Leu Ala Asn Ile Asp Gly Lys
        1010                1015                1020
Ala Tyr Arg Thr Met Met Ser Gln Ile Phe Cys Gln His Ile Ser Pro
1025                1030                1035                1040
Ala Ile Asp Tyr Thr Tyr Asp Ser Asp Ile Leu Lys Gly Asn Phe Leu
                1045                1050                1055
Ile Arg Thr Ala Lys Ile Gln Gln Leu Val Cys Glu Thr Ile Val Arg
            1060                1065                1070
Val Phe Lys Arg His Gly Ala Val Gln Leu Cys Thr Pro Leu Leu Leu
        1075                1080                1085
Pro Arg Asn Arg Gln Ile Tyr Glu His Asn Glu Ala Ala Leu Phe Met
        1090                1095                1100
Asp His Ser Gly Met Leu Val Met Leu Pro Phe Asp Leu Arg Val Pro
1105                1110                1115                1120
Phe Ala Arg Tyr Val Ala Arg Asn Asn Ile Leu Asn Leu Lys Arg Tyr
                1125                1130                1135
Cys Ile Glu Arg Val Phe Arg Pro Arg Lys Leu Asp Arg Phe His Pro
            1140                1145                1150
Lys Glu Leu Leu Glu Cys Ala Phe Asp Ile Val Thr Ser Thr Thr Asn
        1155                1160                1165
Ser Ser Leu Pro Thr Ala Glu Thr Ile Tyr Thr Ile Tyr Glu Ile Ile
        1170                1175                1180
Gln Glu Phe Pro Ala Leu Gln Glu Arg Asn Tyr Ser Ile Tyr Leu Asn
1185                1190                1195                1200
His Thr Met Leu Leu Lys Ala Ile Leu Leu His Cys Gly Ile Pro Glu
                1205                1210                1215
Asp Lys Leu Ser Gln Val Tyr Val Ile Leu Tyr Asp Ala Val Thr Glu
            1220                1225                1230
Lys Leu Thr Arg Arg Glu Val Glu Ala Lys Phe Cys Asn Leu Ser Leu
        1235                1240                1245
Ser Ser Asn Ser Leu Cys Arg Leu Tyr Lys Phe Ile Glu Gln Lys Gly
        1250                1255                1260
Asp Leu Gln Asp Leu Thr Pro Thr Ile Asn Ser Leu Ile Lys Gln Lys
1265                1270                1275                1280
Thr Gly Val Ala Gln Leu Val Lys Tyr Ser Leu Lys Asp Leu Glu Asp
                1285                1290                1295
Val Val Gly Leu Leu Lys Lys Leu Gly Val Lys Leu Gln Val Ser Ile
            1300                1305                1310
Asn Leu Gly Leu Val Tyr Lys Val Gln Gln His Thr Gly Ile Ile Phe
        1315                1320                1325
Gln Phe Leu Ala Phe Ser Lys Arg Arg Gln Arg Val Val Pro Glu Ile
        1330                1335                1340
```

-continued

```
Leu Ala Ala Gly Gly Arg Tyr Asp Leu Leu Ile Pro Lys Phe Arg Gly
1345                1350                1355                1360

Pro Gln Thr Val Gly Pro Val Pro Thr Ala Val Gly Val Ser Ile Ala
            1365                1370                1375

Ile Asp Lys Ile Phe Ala Val Val Leu Asn Met Glu Pro Val Thr
        1380                1385                1390

Val Ser Ser Cys Asp Leu Leu Val Ser Val Gly Gln Met Ser Met
    1395                1400                1405

Ser Arg Ala Ile Asn Leu Thr Gln Lys Leu Trp Thr Ala Gly Ile Thr
1410                1415                1420

Ala Glu Ile Met Tyr Asp Trp Ser Gln Ser Gln Glu Leu Gln Glu
1425                1430                1435                1440

Tyr Cys Arg His His Glu Ile Thr Tyr Val Ala Leu Val Ser Asp Lys
                1445                1450                1455

Glu Gly Ser His Val Lys Val Lys Ser Phe Glu Lys Glu Arg Gln Thr
            1460                1465                1470

Glu Lys Arg Val Leu Glu Ser Asp Leu Val Asp His Val Met Gln Lys
    1475                1480                1485

Leu Arg Thr Lys Val Gly Asp Glu Arg Asn Phe Arg Asp Ala Ser Asp
    1490                1495                1500

Asn Leu Ala Val Gln Thr Leu Lys Gly Ser Phe Ser Asn Ala Ser Gly
1505                1510                1515                1520

Leu Phe Glu Ile His Gly Thr Thr Val Val Pro Asn Val Ile Val Leu
                1525                1530                1535

Ala Pro Glu Lys Leu Ser Ala Ser Thr Arg Arg His Glu Ile Gln
            1540                1545                1550

Val Gln Thr Arg Leu Gln Thr Thr Leu Ala Asn Leu His Gln Lys Ser
    1555                1560                1565

Ser Glu Ile Glu Ile Leu Ala Val Asp Leu Pro Lys Glu Thr Ile Leu
    1570                1575                1580

Gln Phe Leu Ser Leu Glu Trp Asp Ala Asp Glu Gln Ala Phe Asn Thr
1585                1590                1595                1600

Thr Val Lys Gln Leu Leu Ser Arg Leu Pro Lys Gln Arg Tyr Leu Lys
                1605                1610                1615

Leu Val Cys Asp Glu Ile Tyr Asn Ile Lys Val Glu Lys Lys Val Ser
            1620                1625                1630

Val Leu Phe Leu Tyr Ser Tyr Arg Asp Asp Tyr Tyr Arg Ile Leu Phe
            1635                1640                1645
```

<210> SEQ ID NO 6
<211> LENGTH: 270
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (1)...(270)
<223> OTHER INFORMATION: Xaa = Any Amino Acid

<400> SEQUENCE: 6

```
Xaa Xaa Xaa Xaa Xaa Xaa Xaa Xaa Xaa Gly Xaa Gly Xaa Xaa Xaa Xaa
 1               5                   10                  15

Val Xaa Xaa Xaa Xaa Xaa Xaa Xaa Xaa Xaa Xaa Xaa Lys Xaa Xaa
            20                  25                  30

Xaa Xaa Xaa Xaa Xaa Xaa Xaa Xaa Xaa Xaa Xaa Xaa Xaa Xaa Xaa
```

-continued

```
            35                  40                  45
Xaa Glu Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa His Xaa Xaa Xaa Xaa Xaa Xaa Xaa His Arg Asp
        115                 120                 125

Xaa Lys Xaa Xaa Asn Xaa Xaa Xaa Xaa Xaa Xaa Xaa Xaa Xaa Xaa
    130                 135                 140

Xaa Xaa Xaa Xaa Xaa Xaa Lys Xaa Xaa Asp Phe Gly Xaa Xaa Xaa
145                 150                 155                 160

Xaa Xaa Xaa Xaa Xaa Xaa Xaa Xaa Xaa Xaa Xaa Xaa Xaa Xaa Xaa
                165                 170                 175

Xaa Pro Xaa Xaa Xaa Xaa Xaa Xaa Xaa Xaa Xaa Xaa Xaa Xaa Trp
            180                 185                 190

Xaa Xaa Xaa Gly Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Arg Xaa Xaa Xaa Xaa
                245                 250                 255

Xaa Xaa Xaa Xaa Xaa Xaa Xaa Xaa Xaa His Xaa Xaa Xaa
            260                 265                 270

<210> SEQ ID NO 7
<211> LENGTH: 30
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (1)...(30)
<223> OTHER INFORMATION: Xaa = Any Amino Acid

<400> SEQUENCE: 7

Gly Xaa Gly Xaa Xaa Gly Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Lys
            20                  25                  30

<210> SEQ ID NO 8
<211> LENGTH: 105
<212> TYPE: PRT
<213> ORGANISM: Artificial Sequence
<220> FEATURE:
<223> OTHER INFORMATION: Consensus kinase sequence

<400> SEQUENCE: 8

Ile Leu Lys Lys Glu Ser Leu Ser Leu Arg Glu Ile Gln Ile Leu Lys
1               5                   10                  15

Arg Leu Ser His Pro Asn Ile Val Arg Leu Leu Gly Val Phe Glu Asp
            20                  25                  30
```

Thr Asp Asp His Leu Tyr Leu Val Met Glu Tyr Met Glu Gly Gly Asp
            35                  40                  45

Leu Phe Asp Tyr Leu Arg Arg Asn Gly Pro Leu Ser Glu Lys Glu Ala
     50                  55                  60

Lys Lys Ile Ala Leu Gln Ile Leu Arg Gly Leu Glu Tyr Leu His Ser
 65                  70                  75                  80

Asn Gly Ile Val His Arg Asp Leu Lys Pro Glu Asn Ile Leu Leu Asp
                 85                  90                  95

Glu Asn Gly Thr Val Lys Ile Ala Asp
            100                 105

<210> SEQ ID NO 9
<211> LENGTH: 42
<212> TYPE: PRT
<213> ORGANISM: Artificial Sequence
<220> FEATURE:
<223> OTHER INFORMATION: Consensus kinase sequence

<400> SEQUENCE: 9

Arg Leu Pro Leu Pro Ser Asn Cys Ser Glu Glu Leu Lys Asp Leu Leu
 1               5                  10                  15

Lys Lys Cys Leu Asn Lys Asp Pro Ser Lys Arg Pro Gly Ser Ala Thr
            20                  25                  30

Ala Lys Glu Ile Leu Asn His Pro Gln Phe
            35                  40

<210> SEQ ID NO 10
<211> LENGTH: 66
<212> TYPE: PRT
<213> ORGANISM: Artificial Sequence
<220> FEATURE:
<223> OTHER INFORMATION: Consensus kinase sequence

<400> SEQUENCE: 10

Tyr Glu Leu Leu Glu Lys Leu Gly Glu Gly Ser Phe Gly Lys Val Tyr
 1               5                  10                  15

Lys Ala Lys His Lys Thr Gly Lys Ile Val Ala Val Lys Ile Leu Lys
            20                  25                  30

Lys Glu Ser Leu Ser Leu Arg Glu Ile Gln Ile Leu Lys Arg Leu Ser
            35                  40                  45

His Pro Asn Ile Val Arg Leu Leu Gly Val Phe Glu Asp Thr Asp Asp
     50                  55                  60

His Leu
 65

<210> SEQ ID NO 11
<211> LENGTH: 214
<212> TYPE: PRT
<213> ORGANISM: Artificial Sequence
<220> FEATURE:
<223> OTHER INFORMATION: Consensus kinase sequence

<400> SEQUENCE: 11

His Leu Tyr Leu Val Met Glu Tyr Met Glu Gly Gly Asp Leu Phe Asp
 1               5                  10                  15

Tyr Leu Arg Arg Asn Gly Pro Leu Ser Glu Lys Glu Ala Lys Lys Ile
            20                  25                  30

Ala Leu Gln Ile Leu Arg Gly Leu Glu Tyr Leu His Ser Asn Gly Ile
            35                  40                  45

-continued

```
Val His Arg Asp Leu Lys Pro Glu Asn Ile Leu Leu Asp Glu Asn Gly
 50                  55                  60

Thr Val Lys Ile Ala Asp Phe Gly Leu Ala Arg Leu Leu Glu Lys Leu
 65                  70                  75                  80

Thr Thr Phe Val Gly Thr Pro Trp Tyr Met Met Ala Pro Glu Val Ile
                 85                  90                  95

Leu Glu Gly Arg Gly Tyr Ser Ser Lys Val Asp Val Trp Ser Leu Gly
                100                 105                 110

Val Ile Leu Tyr Glu Leu Leu Thr Gly Gly Pro Leu Phe Pro Gly Ala
                115                 120                 125

Asp Leu Pro Ala Phe Thr Gly Gly Asp Glu Val Asp Gln Leu Ile Ile
        130                 135                 140

Phe Val Leu Lys Leu Pro Phe Ser Asp Glu Leu Pro Lys Thr Arg Ile
145                 150                 155                 160

Asp Pro Leu Glu Glu Leu Phe Arg Ile Lys Lys Arg Leu Pro Leu
                165                 170                 175

Pro Ser Asn Cys Ser Glu Glu Leu Lys Asp Leu Leu Lys Lys Cys Leu
                180                 185                 190

Asn Lys Asp Pro Ser Lys Arg Pro Gly Ser Ala Thr Ala Lys Glu Ile
                195                 200                 205

Leu Asn His Pro Gln Phe
        210
```

<210> SEQ ID NO 12
<211> LENGTH: 23
<212> TYPE: PRT
<213> ORGANISM: Artificial Sequence
<220> FEATURE:
<223> OTHER INFORMATION: Consensus kinase sequence

<400> SEQUENCE: 12

```
Thr Asp Ile Ile Lys Tyr Pro Val Ile Thr Glu Lys Leu Ala Met Asn
 1               5                  10                  15

Leu Leu Glu Glu Pro Asn Lys
                20
```

<210> SEQ ID NO 13
<211> LENGTH: 504
<212> TYPE: PRT
<213> ORGANISM: Artificial Sequence
<220> FEATURE:
<223> OTHER INFORMATION: Consensus kinase sequence

<400> SEQUENCE: 13

```
Asn Gln Thr Thr Glu Arg Val Tyr Glu Leu His Lys Ile Glu Leu Phe
 1               5                  10                  15

Ser Val Pro Glu Leu Asn Gly Lys Lys Ile Gly Leu Gly Ile Lys Leu
                20                  25                  30

Pro Lys Thr Asp Thr Glu Ser Leu Arg Thr Met Val Ala Lys Leu Leu
                35                  40                  45

Gly Leu Ala Met Lys Thr Lys Thr Phe Pro Asp Asp Glu Gly Ser Gln
 50                  55                  60

Pro Val Ser Phe Glu Arg Lys Asp Leu Glu Glu Ser Leu Lys Glu Lys
 65                  70                  75                  80

Asp Tyr Phe Val Cys Glu Lys Thr Asp Gly Ile Arg Cys Ser His Gly
                85                  90                  95

Phe Asn Arg Thr Gly Phe Leu Ile Ala Ala Leu Leu Phe Leu Val Glu
                100                 105                 110
```

```
His Pro Gly Leu Glu Glu Ala Ile Ser His Ile Leu Ser Gly Glu Phe
        115                 120                 125

Leu Ile Asp Arg Glu Lys Asn Tyr Tyr Lys Gln Asp Tyr Ile Asp Leu
        130                 135                 140

Leu Pro Lys Arg Leu Phe Pro Arg Glu Lys Asp Lys Thr Lys Ala Lys
145                 150                 155                 160

Glu Leu Pro Thr Tyr His Arg Gly Thr Leu Leu Asp Gly Glu Leu Val
                165                 170                 175

Ile Asp Ile Asn Arg Ile Ala Val Glu Gln Lys Thr Leu Arg Tyr Val
            180                 185                 190

Val Phe Asp Ala Leu Ala Ile Ser Gly Gln Thr Val Ile Gln Arg Asp
            195                 200                 205

Leu Ser Lys Arg Leu Gly Asp Glu Phe Ile Lys Ala Val Lys Lys Pro
        210                 215                 220

Phe Asp Glu Phe Lys Lys Val Met Pro Asp Ala Lys Ile Leu Asn Gln
225                 230                 235                 240

Gln Lys Tyr Asn Phe Pro Phe Lys Ile Gly Leu Lys His Met Ser Leu
                245                 250                 255

Ser Tyr Gly Gln Leu Lys Leu Leu Lys Ala Glu Ser Lys Met Val Ile
            260                 265                 270

Ser Lys Ala Asp Ala Met Pro Lys Leu Leu His Ile Asn Asp Gly Leu
        275                 280                 285

Ile Phe Thr Cys Val Arg Asp Thr Pro Tyr Ile Glu Gly Glu Ile Leu
        290                 295                 300

Val Glu Pro Gly Asn Ser Tyr Leu Asp Phe Asn Leu Leu Lys Trp Lys
305                 310                 315                 320

Pro Lys Glu Glu Asn Thr Val Asp Phe Glu Leu Ile Leu Glu Phe Glu
                325                 330                 335

Glu Val Asn Asp Pro Glu Leu Asp Glu Lys Asp Gly Phe Ser Leu Tyr
            340                 345                 350

Leu Asp Tyr Asp Ala Met Pro Gly Glu Leu Phe Lys Phe Ser Leu Gly
        355                 360                 365

Val Trp Gln Gly Gly Phe Asn Lys Arg Phe Glu Val Ile His Thr Asp
        370                 375                 380

Gln Ile Phe Phe Arg Val Ala Phe Gln Lys Leu Gly Arg Leu Lys His
385                 390                 395                 400

Glu Phe Ala Glu Leu Ser Val Ser Asp Lys Asp Trp Tyr Lys Leu Lys
                405                 410                 415

Ala Leu Glu Gln Pro Leu Asp Gly Arg Ile Val Glu Cys Arg Leu Ala
            420                 425                 430

Asp Ile Glu Ile Leu Ile Phe Gln Glu Gly Arg Trp Glu Tyr Leu Arg
        435                 440                 445

Phe Arg Asp Asp Lys Gln Gln Ala Leu Lys Thr Gly Gly Tyr Ser Gly
        450                 455                 460

Asn His Ile Ser Thr Val Glu Lys Val Leu Leu Ser Ile Lys Asp Gly
465                 470                 475                 480

Val Ser Ile Glu Glu Leu Leu Lys Leu Phe Pro Gly Met Tyr Phe Ala
                485                 490                 495

Gly Ala Lys Thr Leu Ile Lys Arg
                500

<210> SEQ ID NO 14
<211> LENGTH: 231
```

<212> TYPE: PRT
<213> ORGANISM: Artificial Sequence
<220> FEATURE:
<223> OTHER INFORMATION: Consensus kinase sequence

<400> SEQUENCE: 14

```
Tyr Glu Leu Leu Lys Lys Leu Gly Lys Gly Ala Phe Gly Lys Val Tyr
1               5                   10                  15

Leu Ala Arg Asp Lys Lys Thr Gly Arg Leu Val Ala Ile Lys Val Ile
            20                  25                  30

Lys Glu Arg Ile Leu Arg Glu Ile Lys Ile Leu Lys Lys Asp His Pro
        35                  40                  45

Asn Ile Val Lys Leu Tyr Asp Val Phe Glu Asp Lys Leu Tyr Leu
    50                  55                  60

Val Met Glu Tyr Cys Glu Gly Asp Leu Gly Asp Leu Phe Asp Leu Leu
65                  70                  75                  80

Lys Lys Arg Gly Arg Arg Gly Leu Arg Lys Val Leu Ser Glu Glu Ala
            85                  90                  95

Arg Phe Tyr Phe Arg Gln Ile Leu Ser Ala Leu Glu Tyr Leu His Ser
            100                 105                 110

Gln Gly Ile Ile His Arg Asp Leu Lys Pro Glu Asn Ile Leu Leu Asp
            115                 120                 125

Ser His Val Lys Leu Ala Asp Phe Gly Leu Ala Arg Gln Leu Thr Thr
    130                 135                 140

Phe Val Gly Thr Pro Glu Tyr Met Ala Pro Glu Val Leu Gly Tyr Gly
145                 150                 155                 160

Lys Pro Ala Val Asp Ile Trp Ser Leu Gly Cys Ile Leu Tyr Glu Leu
                165                 170                 175

Leu Thr Gly Lys Pro Pro Phe Pro Gln Leu Asp Leu Ile Phe Lys Lys
            180                 185                 190

Ile Gly Ser Pro Glu Ala Lys Asp Leu Ile Lys Lys Leu Leu Val Lys
        195                 200                 205

Asp Pro Glu Lys Arg Leu Thr Ala Glu Ala Leu Glu Asp Glu Leu Asp
    210                 215                 220

Ile Lys Ala His Pro Phe Phe
225                 230
```

<210> SEQ ID NO 15
<211> LENGTH: 231
<212> TYPE: PRT
<213> ORGANISM: Artificial Sequence
<220> FEATURE:
<223> OTHER INFORMATION: Consensus kinase sequence

<400> SEQUENCE: 15

```
Tyr Glu Leu Leu Lys Lys Leu Gly Lys Gly Ala Phe Gly Lys Val Tyr
1               5                   10                  15

Leu Ala Arg Asp Lys Lys Thr Gly Arg Leu Val Ala Ile Lys Val Ile
            20                  25                  30

Lys Glu Arg Ile Leu Arg Glu Ile Lys Ile Leu Lys Lys Asp His Pro
        35                  40                  45

Asn Ile Val Lys Leu Tyr Asp Val Phe Glu Asp Lys Leu Tyr Leu
    50                  55                  60

Val Met Glu Tyr Cys Glu Gly Asp Leu Gly Asp Leu Phe Asp Leu Leu
65                  70                  75                  80

Lys Lys Arg Gly Arg Arg Gly Leu Arg Lys Val Leu Ser Glu Glu Ala
            85                  90                  95
```

```
Arg Phe Tyr Phe Arg Gln Ile Leu Ser Ala Leu Glu Tyr Leu His Ser
            100                 105                 110
Gln Gly Ile Ile His Arg Asp Leu Lys Pro Glu Asn Ile Leu Leu Asp
        115                 120                 125
Ser His Val Lys Leu Ala Asp Phe Gly Leu Ala Arg Gln Leu Thr Thr
    130                 135                 140
Phe Val Gly Thr Pro Glu Tyr Met Ala Pro Glu Val Leu Gly Tyr Gly
145                 150                 155                 160
Lys Pro Ala Val Asp Ile Trp Ser Leu Gly Cys Ile Leu Tyr Glu Leu
                165                 170                 175
Leu Thr Gly Lys Pro Pro Phe Pro Gln Leu Asp Leu Ile Phe Lys Lys
            180                 185                 190
Ile Gly Ser Pro Glu Ala Lys Asp Leu Ile Lys Lys Leu Leu Val Lys
        195                 200                 205
Asp Pro Glu Lys Arg Leu Thr Ala Glu Ala Leu Glu Asp Glu Leu Asp
    210                 215                 220
Ile Lys Ala His Pro Phe Phe
225                 230

<210> SEQ ID NO 16
<211> LENGTH: 280
<212> TYPE: PRT
<213> ORGANISM: Artificial Sequence
<220> FEATURE:
<223> OTHER INFORMATION: Consensus kinase sequence

<400> SEQUENCE: 16

Leu Thr Leu Gly Lys Lys Leu Gly Glu Gly Ala Phe Gly Glu Val Tyr
1               5                   10                  15
Lys Gly Thr Leu Lys Ile Glu Val Ala Val Lys Thr Leu Lys Glu Asp
            20                  25                  30
Ala Lys Glu Glu Phe Leu Arg Glu Ala Lys Ile Met Lys Lys Leu Gly
        35                  40                  45
Gly Lys His Pro Asn Ile Val Lys Leu Leu Gly Val Cys Thr Glu Glu
    50                  55                  60
Gly Arg Arg Phe Met Glu Val Glu Pro Leu Met Ile Val Met Glu Tyr
65                  70                  75                  80
Met Glu Gly Gly Asp Leu Leu Asp Tyr Leu Arg Lys Asn Arg Pro Lys
                85                  90                  95
Leu Ser Leu Ser Asp Leu Leu Ser Phe Ala Leu Gln Ile Ala Lys Gly
            100                 105                 110
Met Glu Tyr Leu Glu Ser Lys Asn Phe Val His Arg Asp Leu Ala Ala
        115                 120                 125
Arg Asn Cys Leu Val Gly Glu Asn Lys Val Val Lys Ile Ser Asp Phe
    130                 135                 140
Gly Leu Ser Arg Asp Leu Tyr Asp Asp Lys Lys Gly Glu Ser Lys
145                 150                 155                 160
Asp Tyr Tyr Arg Lys Lys Gly Lys Gly Lys Thr Leu Leu Pro
                165                 170                 175
Ile Arg Trp Met Ala Pro Glu Ser Leu Lys Asp Gly Lys Phe Thr Ser
            180                 185                 190
Lys Ser Asp Val Trp Ser Phe Gly Val Leu Leu Trp Glu Ile Phe Thr
        195                 200                 205
Leu Gly Glu Gln Pro Tyr Pro Gly Glu Ile Gln Gln Phe Met Ser Asn
    210                 215                 220
```

```
Glu Glu Val Leu Glu Tyr Leu Lys Lys Gly Tyr Arg Leu Pro Lys Pro
225                 230                 235                 240

Glu Asn Asp Leu Pro Ile Ser Ser Val Thr Cys Pro Asp Glu Leu Tyr
                245                 250                 255

Asp Leu Met Leu Gln Cys Trp Ala Glu Asp Pro Glu Asp Arg Pro Thr
            260                 265                 270

Phe Ser Glu Leu Val Glu Arg Leu
        275                 280

<210> SEQ ID NO 17
<211> LENGTH: 144
<212> TYPE: PRT
<213> ORGANISM: Artificial Sequence
<220> FEATURE:
<223> OTHER INFORMATION: Consensus kinase sequence

<400> SEQUENCE: 17

Ser Phe Arg Glu Arg Gln Ala Gln Glu Leu Glu Val Ile Lys Ser Ile
1               5                   10                  15

Phe Gly Cys Asp Val Glu Asp Leu Arg Pro Gln Ala Asn Pro Ser Leu
            20                  25                  30

Trp Lys Pro Thr Asp Ile Arg Ile Gln Leu Thr Pro Leu Arg Asp Ser
        35                  40                  45

Ser Asn Gly Leu Glu Thr Tyr Val Cys Thr Lys Leu His Val Thr Cys
    50                  55                  60

Pro Ser Lys Tyr Pro Lys Leu Pro Pro Lys Ile Ser Leu Glu Glu Ser
65                  70                  75                  80

Lys Gly Met Ser Asp Gln Leu Leu Glu Ala Leu Arg Asn Gln Leu Gln
                85                  90                  95

Ala Gln Ser Gln Glu Leu Arg Gly Glu Val Met Ile Tyr Glu Leu Ala
            100                 105                 110

Gln Thr Val Gln Ala Phe Leu Leu Glu His Asn Lys Pro Pro Lys Gly
        115                 120                 125

Ser Phe Tyr Asp Gln Met Leu Gln Asp Lys Gln Lys Arg Asp Gln Glu
    130                 135                 140

<210> SEQ ID NO 18
<211> LENGTH: 54
<212> TYPE: PRT
<213> ORGANISM: Artificial Sequence
<220> FEATURE:
<223> OTHER INFORMATION: Consensus kinase sequence

<400> SEQUENCE: 18

Glu Thr Leu Tyr Phe His Lys Met Gly Arg Gln Ile Gln Arg Gly Cys
1               5                   10                  15

Cys Val Gly His Ser Gln Arg Gly Cys Ile Ala Tyr Thr Gly Ile Asp
            20                  25                  30

Met His Cys Gly Gln Leu Leu Tyr Ile Thr Glu Trp Asn Ile Lys Tyr
        35                  40                  45

Ser Gln Leu Glu Gln Pro
    50

<210> SEQ ID NO 19
<211> LENGTH: 332
<212> TYPE: PRT
<213> ORGANISM: Artificial Sequence
<220> FEATURE:
<223> OTHER INFORMATION: Consensus kinase sequence
```

```
<400> SEQUENCE: 19

Leu Lys Ser Leu Met Arg Gly Lys Gly Glu Ala Ala Ser Leu Ala Arg
1               5                   10                  15

Gly Ala Leu Arg Glu Leu Glu Thr Val Val Gly Leu Ala Tyr Ser Leu
            20                  25                  30

Gly Val Lys Cys Pro Ile His Ile Trp Ala Gly Leu Pro Ile Ser Phe
        35                  40                  45

Asp Arg Ala Ser Asn Gly Gly Ile Val Trp Gln Met Thr Ala Asp Leu
    50                  55                  60

Lys Pro Asn Arg Ser Gly His Pro Ser Val Leu Ala Ile Gly Glu Arg
65                  70                  75                  80

Tyr Asp Ser Met Leu His Glu Phe Gln Lys Gln Ala Gln Lys Phe Asn
                85                  90                  95

Pro Ala Met Pro Ala Arg Gly Val Leu Ser Gly Ala Gly Leu Thr Phe
            100                 105                 110

Ser Leu Asp Lys Leu Val Ala Ala Val Gly Val Glu Tyr Ala Lys Asp
            115                 120                 125

Cys Arg Ala Ile Asp Val Gly Ile Cys Val Cys Gly Thr Arg Pro Pro
    130                 135                 140

Leu Lys Asp Val Thr Tyr Ile Met Arg Leu Leu Trp Ser Val Gly Ile
145                 150                 155                 160

Arg Cys Gly Ile Val Glu Ala Ala Ser Glu Leu Gly Asp Glu Ala Gln
                165                 170                 175

Asp Leu Ala Arg Leu Gly Ala Leu His Val Ile Leu Val Ala Glu Asn
            180                 185                 190

Gly Ser Leu Arg Val Arg Ser Phe Glu Arg Glu Arg Phe Gln Glu Arg
        195                 200                 205

His Leu Thr Arg Thr Glu Leu Val Glu Phe Ile Gln Lys Met Leu Arg
    210                 215                 220

Ser Asp Gly Leu Asn Gly Thr Thr Val Asp Asn Phe Ser His Leu Ser
225                 230                 235                 240

Ala Leu Gly Ser Gly Asp Asn Arg Ser Ser Gly Gly Lys Glu Arg Glu
                245                 250                 255

Arg Gly Glu Asn Gly Leu Ser Thr Ser Ala Ser Asn Ala Thr Ile Lys
            260                 265                 270

Asn Asn Tyr Ser Gln Leu Pro Asn Leu Gln Val Thr Phe Leu Thr His
        275                 280                 285

Asp Lys Pro Thr Ala Asn Tyr Lys Arg Arg Leu Glu Asn Gln Val Ala
    290                 295                 300

Gln Gln Met Ser Ser Thr Leu Ser Gln Phe Leu Lys Lys Glu Thr Phe
305                 310                 315                 320

Val Val Leu Val Val Glu Leu Pro Pro Ala Val Val
                325                 330

<210> SEQ ID NO 20
<211> LENGTH: 296
<212> TYPE: PRT
<213> ORGANISM: Artificial Sequence
<220> FEATURE:
<223> OTHER INFORMATION: Consensus kinase sequence

<400> SEQUENCE: 20

Val Leu Ser Gly Ala Gly Leu Thr Phe Ser Leu Asp Lys Leu Val Ala
1               5                   10                  15
```

```
Ala Val Gly Val Glu Tyr Ala Lys Asp Cys Arg Ala Ile Asp Val Gly
             20                  25                  30

Ile Cys Val Cys Gly Thr Arg Pro Pro Leu Lys Asp Val Thr Tyr Ile
             35                  40                  45

Met Arg Leu Leu Trp Ser Val Gly Ile Arg Cys Gly Ile Val Glu Ala
 50                  55                  60

Ala Ser Glu Leu Gly Asp Glu Ala Gln Asp Leu Ala Arg Leu Gly Ala
 65                      70                  75                  80

Leu His Val Ile Leu Val Ala Glu Asn Gly Ser Leu Arg Val Arg Ser
                 85                  90                  95

Phe Glu Arg Glu Arg Phe Gln Glu Arg His Leu Thr Arg Thr Glu Leu
             100                 105                 110

Val Glu Phe Ile Gln Lys Met Leu Arg Ser Asp Gly Leu Asn Gly Thr
             115                 120                 125

Thr Val Asp Asn Phe Ser His Leu Ser Ala Leu Gly Ser Gly Asp Asn
130                 135                 140

Arg Ser Ser Gly Gly Lys Glu Arg Glu Arg Gly Glu Asn Gly Leu Ser
145                 150                 155                 160

Thr Ser Ala Ser Asn Ala Thr Ile Lys Asn Asn Tyr Ser Gln Leu Pro
                 165                 170                 175

Asn Leu Gln Val Thr Phe Leu Thr His Asp Lys Pro Thr Ala Asn Tyr
             180                 185                 190

Lys Arg Arg Leu Glu Asn Gln Val Ala Gln Met Ser Ser Thr Leu
             195                 200                 205

Ser Gln Phe Leu Lys Lys Glu Thr Phe Val Val Leu Val Glu Leu
 210                 215                 220

Pro Pro Ala Val Val Asn Ala Ile Val Gly Ala Ile Asn Pro Arg Glu
225                 230                 235                 240

Ile Arg Lys Arg Glu Thr Glu Pro Glu Ile Asn Tyr Val Ile Glu Arg
                 245                 250                 255

Phe Ser Lys Tyr Lys Arg Tyr Ile Ser Glu Ile Asn Glu Glu Val Val
             260                 265                 270

Asp Tyr Leu Ser Asp Ala Lys Thr Pro Ile Val Ala Leu Tyr Ser Ile
             275                 280                 285

Ser Asp Ser Tyr Tyr Arg Val Ile
290                 295

<210> SEQ ID NO 21
<211> LENGTH: 126
<212> TYPE: PRT
<213> ORGANISM: Artificial Sequence
<220> FEATURE:
<223> OTHER INFORMATION: Consensus kinase sequence

<400> SEQUENCE: 21

Asp Gln Gly Gly Glu Leu Leu Ser Leu Arg Tyr Asp Leu Thr Val Pro
 1               5                  10                  15

Phe Ala Arg Tyr Val Ala Met Asn Leu Leu Lys Val Thr Asn Leu Pro
             20                  25                  30

Leu Lys Arg Tyr His Ile Ala Lys Val Tyr Arg Arg Asp Arg Pro Ala
             35                  40                  45

Met Thr Arg Gly Arg Tyr Arg Glu Phe Tyr Gln Cys Asp Phe Asp Ile
 50                  55                  60

Ile Gly Glu Tyr Asp Thr Met Ala Pro Asp Ala Glu Ile Leu Lys Ile
65                  70                  75                  80
```

```
Leu Thr Glu Ile Leu Ser Gln Leu Gly Ile Arg Glu Leu Gly Asn Phe
                85                  90                  95

Lys Ile Lys Ile Asn His Arg Gly Ile Leu Asp Ser Leu Leu Gln Pro
            100                 105                 110

Trp Pro Lys Thr Leu Gln Glu Tyr Leu Thr Gln Tyr Lys Ala
        115                 120                 125

<210> SEQ ID NO 22
<211> LENGTH: 104
<212> TYPE: PRT
<213> ORGANISM: Artificial Sequence
<220> FEATURE:
<223> OTHER INFORMATION: Consensus kinase sequence

<400> SEQUENCE: 22

Asp Leu Lys Pro Glu Asn Ile Leu Leu Asp Glu Glu Ser His Glu Asn
  1               5                  10                  15

Thr Pro Asn Met Ile Lys Leu Ile Ala Asp Phe Gly Leu Ala Lys Glu
             20                  25                  30

Ile Tyr Ser Ser Ser Ser Thr Tyr Glu Glu Met Ser Ser Ser Gln Ala
            35                  40                  45

Val Phe Gly Ser His Gln Thr Thr Ser Thr Met Cys Gly Thr Pro Tyr
   50                  55                  60

Tyr Val Ser Met Lys Ser Met Ala Pro Glu Tyr Met Ala Pro Glu Ser
65                  70                  75                  80

Ser Ala Thr Asn Tyr Gln Lys Tyr Ser Thr Lys Ser Asp Val Trp Ser
                85                  90                  95

Phe Gly Val Ile Leu Tyr Glu Met
            100

<210> SEQ ID NO 23
<211> LENGTH: 100
<212> TYPE: PRT
<213> ORGANISM: Artificial Sequence
<220> FEATURE:
<223> OTHER INFORMATION: Consensus kinase sequence

<400> SEQUENCE: 23

Gln Leu Met His Tyr Val His Gln Ile Ala Lys Gly Leu Glu Tyr Leu
  1               5                  10                  15

His Ser Lys Asn Gln Lys His Gln Gly Ile Ile His Arg Ala Lys Lys
             20                  25                  30

Val Asp Leu Lys Pro Glu Asn Ile Leu Leu Asp Glu Glu Ser His Glu
            35                  40                  45

Asn Thr Pro Asn Met Ile Lys Leu Ile Ala Asp Phe Gly Leu Ala Lys
   50                  55                  60

Glu Ile Tyr Ser Ser Ser Ser Thr Tyr Glu Glu Met Ser Ser Ser Gln
65                  70                  75                  80

Ala Val Phe Gly Ser His Gln Thr Thr Ser Thr Met Cys Gly Thr Pro
                85                  90                  95

Tyr Tyr Val Ser
            100

<210> SEQ ID NO 24
<211> LENGTH: 119
<212> TYPE: PRT
<213> ORGANISM: Artificial Sequence
<220> FEATURE:
<223> OTHER INFORMATION: Consensus kinase sequence
```

-continued

```
<400> SEQUENCE: 24

Glu Gly Ser Leu Val Glu Tyr Met Glu Tyr Met Ser Gly Gly Ser Glu
1               5                   10                  15

Asp Tyr Met Lys Lys Leu Ser Leu Glu Thr Val Met Lys Ile Ala Met
            20                  25                  30

Met Ile Leu Gln Phe Met Gln Ile Met His Met Ser Ser Glu Ser Glu
        35                  40                  45

Ser Leu Ser His Ser Gln Leu Met His Tyr Val His Gln Ile Ala Lys
    50                  55                  60

Gly Leu Glu Tyr Leu His Ser Lys Asn Gln Lys His Gln Gly Ile Ile
65                  70                  75                  80

His Arg Ala Lys Lys Val Asp Leu Lys Pro Glu Asn Ile Leu Leu Asp
                85                  90                  95

Glu Glu Ser His Glu Asn Thr Pro Asn Met Ile Lys Leu Ile Ala Asp
            100                 105                 110

Phe Gly Leu Ala Lys Glu Ile
        115

<210> SEQ ID NO 25
<211> LENGTH: 122
<212> TYPE: PRT
<213> ORGANISM: Artificial Sequence
<220> FEATURE:
<223> OTHER INFORMATION: Consensus kinase sequence

<400> SEQUENCE: 25

Tyr Met Ala Pro Glu Ser Ser Ala Thr Asn Tyr Gln Lys Tyr Ser Thr
1               5                   10                  15

Lys Ser Asp Val Trp Ser Phe Gly Val Ile Leu Tyr Glu Met Leu Thr
            20                  25                  30

Gly Lys Pro Pro Phe Phe Pro Gly Glu Ser Glu Val Ser Glu Glu Glu
        35                  40                  45

Pro Tyr Gln Ser Met Lys Asn Met Glu Val Leu Glu Met Gly Pro Glu
    50                  55                  60

Glu Thr Ile Gln Lys Val Met Ser Lys Ile Val Glu Lys Lys Gly Glu
65                  70                  75                  80

Arg Met Pro Gln Pro Ser Ser Ser Asn Cys Pro Glu Val Ser Gln Glu
                85                  90                  95

Ala Lys Asp Leu Leu Lys Lys Cys Leu Gln Lys Asp Pro Glu Lys Arg
            100                 105                 110

Arg Pro Thr Phe Glu Glu Ile Leu Gln His
        115                 120

<210> SEQ ID NO 26
<211> LENGTH: 23
<212> TYPE: PRT
<213> ORGANISM: Artificial Sequence
<220> FEATURE:
<223> OTHER INFORMATION: Consensus kinase sequence

<400> SEQUENCE: 26

Gln Tyr Glu Leu Leu Lys Lys Leu Leu Gly Lys Gly Ser Phe Gly Lys
1               5                   10                  15

Val Tyr Lys Ala Lys His Lys
            20

<210> SEQ ID NO 27
<211> LENGTH: 39
```

<212> TYPE: PRT
<213> ORGANISM: Artificial Sequence
<220> FEATURE:
<223> OTHER INFORMATION: Consensus kinase sequence

<400> SEQUENCE: 27

Glu Val Ser Gln Glu Ala Lys Asp Leu Leu Lys Lys Cys Leu Gln Lys
1               5                   10                  15

Asp Pro Glu Lys Arg Arg Pro Thr Phe Glu Glu Ile Leu Gln His Pro
            20                  25                  30

Trp Phe Leu Met Arg Asn Pro
        35

<210> SEQ ID NO 28
<211> LENGTH: 11
<212> TYPE: PRT
<213> ORGANISM: Artificial Sequence
<220> FEATURE:
<223> OTHER INFORMATION: Consensus kinase sequence

<400> SEQUENCE: 28

Leu Gly Thr Gly Ser Phe Gly Ala Val Tyr Lys
1               5                   10

<210> SEQ ID NO 29
<211> LENGTH: 104
<212> TYPE: PRT
<213> ORGANISM: Artificial Sequence
<220> FEATURE:
<223> OTHER INFORMATION: Consensus kinase sequence

<400> SEQUENCE: 29

Leu Asp Gln Asn Gly Thr Val Leu Gln Leu Pro Phe Asp Leu Met Met
1               5                   10                  15

Gly His Ala Arg Ser Leu Ala Arg Ile Thr Asn Ser Pro Val Val Gln
            20                  25                  30

Lys Ser Tyr Ser Phe Gly Asn Ile Phe Arg Asp Arg His Gly Gly Gly
        35                  40                  45

Gln Pro Asp Val Tyr Gly Glu Val Asp Phe Asp Ile Val Thr Ser Asp
    50                  55                  60

Ala Leu Asp Leu Ala Leu Lys Glu Ala Glu Val Ile Lys Val Leu Asp
65                  70                  75                  80

Glu Ile Ala Thr Ala Phe Pro Thr Val Ser Thr Pro Ile Cys Phe
                85                  90                  95

Gln Leu Gly His Ser Asp Leu Leu
            100

<210> SEQ ID NO 30
<211> LENGTH: 151
<212> TYPE: PRT
<213> ORGANISM: Artificial Sequence
<220> FEATURE:
<223> OTHER INFORMATION: Consensus kinase sequence

<400> SEQUENCE: 30

Tyr Gln Glu Val Gln Glu Ser Glu Val Met Val Leu Gln Ala Ile Tyr
1               5                   10                  15

Gly Glu Asp Phe Thr Gln His Glu Ala Ala His Gly Ala Trp Gln Lys
            20                  25                  30

Ser Glu Pro Arg Phe Asp Ile Lys Ile Lys Pro Ser Ser Asp Gln Glu
        35                  40                  45

```
Leu Ser Val Thr Leu Gly Val Met Val Ala Thr Tyr Pro Lys Thr
        50                  55                  60

Pro Pro Leu Leu Thr Ile Lys Asp Asp His Ser Leu Arg Glu Ser Thr
 65              70                  75                  80

Lys Phe Lys Ile Gln Lys Phe Val Glu Thr Gln Pro Lys Ile Tyr Ala
                 85                  90                  95

Gln Ala Glu Gln Glu Met Ile Asp Gln Ile Val Glu Gly Ile Arg Asp
                100                 105                 110

Ile Leu Glu Glu Ala Ala Gln Lys Lys Val Gln Gly Leu Glu Ile Pro
            115                 120                 125

Ser Leu Glu Glu Glu Arg Ala Ala His Glu Ala Glu Leu Ala Arg Leu
        130                 135                 140

Ala Gln Ser Glu Lys Glu Arg
145                 150

<210> SEQ ID NO 31
<211> LENGTH: 48
<212> TYPE: PRT
<213> ORGANISM: Artificial Sequence
<220> FEATURE:
<223> OTHER INFORMATION: Consensus kinase sequence

<400> SEQUENCE: 31

Glu Ala Glu Leu Ala Arg Leu Ala Gln Ser Glu Lys Glu Arg Glu Glu
 1               5                  10                  15

Arg Lys Lys Leu Glu Glu Ser Lys Glu Glu Arg Val Leu Glu Asp
                20                  25                  30

Met Leu Gln Glu Glu Leu Lys Arg Gln Arg Asn Lys Ala Lys Glu Ser
             35                  40                  45

<210> SEQ ID NO 32
<211> LENGTH: 59
<212> TYPE: PRT
<213> ORGANISM: Artificial Sequence
<220> FEATURE:
<223> OTHER INFORMATION: Consensus kinase sequence

<400> SEQUENCE: 32

Arg Asn Lys Ala Lys Glu Ser Arg Lys Lys Asn Arg Ser His Gln Leu
 1               5                  10                  15

Ser Pro Asp Arg Ala Pro Gln Asp Pro Gly Glu Thr Asp Glu Thr Leu
                20                  25                  30

Met Phe Asp Gln Pro Cys Lys Ile Thr Asp Gly Ser Gly Asn Ala Leu
             35                  40                  45

Phe Phe Gln Thr Val Ile Gly Lys Thr Val Phe
     50                  55

<210> SEQ ID NO 33
<211> LENGTH: 83
<212> TYPE: PRT
<213> ORGANISM: Artificial Sequence
<220> FEATURE:
<223> OTHER INFORMATION: Consensus kinase sequence

<400> SEQUENCE: 33

Leu Glu Glu Ser Lys Glu Glu Arg Val Leu Glu Asp Met Leu Gln
 1               5                  10                  15

Glu Glu Leu Lys Arg Gln Arg Asn Lys Ala Lys Glu Ser Arg Lys Lys
                20                  25                  30

Asn Arg Ser His Gln Leu Ser Pro Asp Arg Ala Pro Gln Asp Pro Gly
```

-continued

```
            35                  40                  45
Glu Thr Asp Glu Thr Leu Met Phe Asp Gln Pro Cys Lys Ile Thr Asp
        50                  55                  60

Gly Ser Gly Asn Ala Leu Phe Phe Gln Thr Val Ile Gly Lys Thr Val
65                  70                  75                  80

Phe Arg Glu
```

What is claimed is:

1. An isolated nucleic acid molecule selected from the group consisting of:
   (a) a nucleic acid molecule comprising the nucleotide sequence set forth in SEQ ID NO:1; and
   (b) a nucleic acid molecule comprising nucleotides 63 to 5012 of the nucleotide sequence set forth in SEQ ID NO:1.

2. An isolated nucleic acid molecule which encodes a polypeptide comprising the amino acid sequence set forth in SEQ ID NO:2.

3. An isolated nucleic acid molecule comprising the nucleotide sequence set forth in SEQ ID NO:1.

4. An isolated nucleic acid molecule which encodes a naturally occurring variant of a polypeptide comprising the amino acid sequence of SEQ ID NO:2, said variant having kinase activity, wherein
   the nucleic acid molecule hybridizes to a nucleic acid molecule comprising nucleotides 63 to 5012 of SEQ ID NO:1 in 0.5M sodium phosphate, 7% SDS at 65° C., followed by one or more washes in 0.2×SSC at 65° C. and
   the nucleic acid molecule is at least 95% homologous to SEQ ID NO:1 or nucleotides 63 to 5012 of SEQ ID NO:1.

5. An isolated nucleic acid molecule comprising a nucleotide sequence which is completely complementary to the nucleotide sequence of the nucleic acid molecule of any one of claims 1, 2, 3, or 4.

6. An isolated nucleic acid molecule comprising the nucleic acid molecule of any one of claims 1, 2, 3, or 4 and a nucleotide sequence encoding a heterologous polypeptide.

7. A vector comprising the nucleic acid molecule of any one of claims 1, 2, 3, or 4.

8. The vector of claim 7, which is an expression vector.

9. A host cell transfected with the vector of claim 7.

10. A method of producing a polypeptide comprising culturing a host cell transfected with the vector of claim 7 in an appropriate culture medium to produce the polypeptide expressed by the nucleic acid molecule.

11. A kit comprising the nucleic acid molecule of any one of claims 1, 2, 3, or 4 and instructions for use.

12. The method defined in claim 10, further comprising isolating the polypeptide.

13. The isolated nucleic acid molecule of claim 1 consisting of nucleotides 63 to 5012 of SEQ ID NO:1.

14. The isolated nucleic acid molecule of claim 1 consisting of SEQ ID NO:1.

15. The isolated nucleic acid molecule of claim 4 which is at least 97% homologous to SEQ ID NO:1 or nucleotides 63 to 5012 of SEQ ID NO:1.

16. The isolated nucleic acid molecule of claim 4 which is at least 99% homologous to SEQ ID NO:1 or nucleotides 63 to 5012 of SEQ ID NO:1.

17. The isolated nucleic acid molecule of claim 4 which encodes a polypeptide comprising an amino acid sequence which is at least about 98% homologous to the amino acid sequence of SEQ ID NO:2.

18. The isolated nucleic acid molecule of claim 4 which encodes a polypeptide comprising an amino acid sequence which is at least about 99% homologous to the amino acid sequence of SEQ ID NO:2.

* * * * *